(12) United States Patent
Foley et al.

(10) Patent No.: US 8,791,303 B2
(45) Date of Patent: Jul. 29, 2014

(54) HERBICIDES

(75) Inventors: Daniel Jason Foley, Blackthorn (GB); Stephane André Marie Jeanmart, Stein (CH); Adrian Longstaff, Centre Bracknell (GB); Robert William Parsons, Bracknell (GB); Claire Janet Russell, Bracknell (GB); John Benjamin Taylor, Bracknell (GB); Jeffrey Steven Wailes, Bracknell (GB)

(73) Assignee: Syngenta Limited, Guildford, Surrey (GB)

( * ) Notice: Subject to any disclaimer, the term of this patent is extended or adjusted under 35 U.S.C. 154(b) by 102 days.

(21) Appl. No.: 13/384,305

(22) PCT Filed: Jul. 15, 2010

(86) PCT No.: PCT/GB2010/001354
§ 371 (c)(1),
(2), (4) Date: Mar. 26, 2012

(87) PCT Pub. No.: WO2011/007146
PCT Pub. Date: Jan. 20, 2011

(65) Prior Publication Data
US 2012/0178623 A1  Jul. 12, 2012

(30) Foreign Application Priority Data

Jul. 16, 2009  (GB) .................................. 0912385.2

(51) Int. Cl.
*C07C 49/657* (2006.01)
*A01N 25/22* (2006.01)
*A01N 37/34* (2006.01)
*A01N 37/52* (2006.01)

(52) U.S. Cl.
USPC ............................ 568/327; 568/330; 504/105

(58) Field of Classification Search
USPC .................................. 568/327, 330; 504/105
See application file for complete search history.

(56) References Cited

U.S. PATENT DOCUMENTS

| | | | |
|---|---|---|---|
| 4,283,348 A | 8/1981 | Wheeler | |
| 4,338,122 A | 7/1982 | Wheeler | |
| 4,489,012 A | 12/1984 | Hodakowski | |
| 4,526,723 A | 7/1985 | Wheeler et al. | |
| 4,551,547 A | 11/1985 | Wheeler | |
| 5,684,205 A | 11/1997 | Norman et al. | |
| 5,840,661 A | 11/1998 | Fischer et al. | |
| 6,251,833 B1 | 6/2001 | Erdelen et al. | |
| 6,358,887 B1 | 3/2002 | Fischer et al. | |
| 6,458,965 B1 | 10/2002 | Fischer et al. | |
| 6,642,180 B1 | 11/2003 | Fischer et al. | |
| 6,894,005 B1 | 5/2005 | Maetzke et al. | |
| 2003/0216260 A1 | 11/2003 | Ruther et al. | |
| 2007/0015664 A1 | 1/2007 | Fischer et al. | |
| 2009/0137393 A1 | 5/2009 | Fischer et al. | |
| 2009/0227563 A1 | 9/2009 | Fischer et al. | |
| 2011/0263428 A1 | 10/2011 | Jeanmart et al. | |
| 2012/0028800 A1 | 2/2012 | Mathews et al. | |
| 2012/0065064 A1 | 3/2012 | Taylor et al. | |
| 2012/0094832 A1 | 4/2012 | Tyte et al. | |
| 2012/0142529 A1 | 6/2012 | Tyte et al. | |

FOREIGN PATENT DOCUMENTS

| | | |
|---|---|---|
| CA | 2322158 A1 | 8/2000 |
| CA | 2456776 A1 | 2/2004 |
| EP | 0701988 A1 | 3/1996 |
| WO | 9601798 A1 | 1/1996 |
| WO | 9625395 A1 | 8/1996 |
| WO | 9839281 A1 | 9/1998 |
| WO | 9943649 A1 | 9/1999 |
| WO | 9948869 A1 | 9/1999 |
| WO | 0109092 A1 | 2/2001 |
| WO | 0117972 A2 | 3/2001 |
| WO | 0174770 A1 | 10/2001 |
| WO | 03013249 A1 | 2/2003 |
| WO | 2004080962 A1 | 9/2004 |
| WO | 2007068427 A2 | 6/2007 |
| WO | 2007080066 A2 | 7/2007 |
| WO | 2008145336 A1 | 12/2008 |
| WO | 2009019015 A1 | 2/2009 |
| WO | 2010000773 A1 | 1/2010 |
| WO | 2010069834 A1 | 6/2010 |

OTHER PUBLICATIONS

J. Wenger and T. Nidermann, "Chapter 9: Acetyl-CoA Carboxylase Inhibitors", in Modern Crop Protection Compounds, ed. W. Kraemer et al., Wiley-VCH Verlag, Weinheim, 2007, pp. 335-357.

*Primary Examiner* — Sikarl Witherspoon
(74) *Attorney, Agent, or Firm* — R. Kody Jones

(57) ABSTRACT

Compounds of formula (I) are suitable for use as herbicides: wherein R is methyl, ethyl, vinyl, ethynyl or cyclopropyl, $R^1$ is hydrogen, $C_1$-$C_6$alkyl, $C_1$-$C_6$haloalkyl, $C_3$-$C_7$cycloalkyl, $C_1$-$C_6$alkoxy, $C_1$-$C_6$haloalkoxy, vinyl, propenyl, ethynyl, propynyl, halogen, or optionally substituted phenyl, $R^2$ is methyl, ethyl, vinyl, ethynyl or methoxy, $R^3$ and $R^4$ are hydrogen or together form a double bond, A is $C_3$-$C_7$cycloalkyl which is unsubstituted or substituted once or twice by $C_1$-$C_6$alkyl, $C_1$-$C_6$haloalkyl, $C_1$-$C_6$alkoxy, $C_1$-$C_6$alkylcarbonyloxy, $C_2$-$C_6$alkenyl, =O or =N—$R^{10}$, or A is cyclohexyl substituted once, at the 4-position, by one ($C_3$-$C_6$cycloalkyl)methoxy, $C_3$-$C_6$cycloalkyloxy, $C_2$-$C_5$alkenyl-$CH_2$-oxy, or benzyloxy substituent, or A is decahydro-1-naphthyl or decahydro-2-naphthyl, or A is optionally substituted phenyl, and G is hydrogen or an agriculturally acceptable metal, sulfonium, ammonium or a latentiating group.

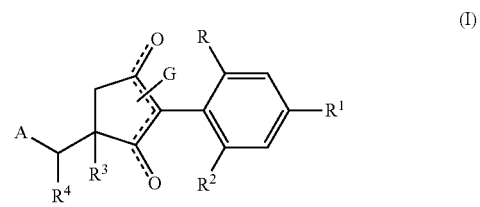

25 Claims, No Drawings

HERBICIDES

This application is a 371 of International Application No. PCT/GB2010/001354 filed Jul. 15, 2010, which claims priority to GB 0912385.2 filed Jul. 16, 2009, the contents of which are incorporated herein by reference.

The present invention relates to novel, herbicidally active cyclopentanedione compounds, and derivatives thereof, specifically herbicidally active 2-(substituted-phenyl)-cyclopentane-1,3-dione derivatives, to processes for their preparation, to compositions comprising those compounds, and to their use in controlling weeds, especially in crops of useful plants, or in inhibiting undesired plant growth.

U.S. Pat. No. 4,338,122 (Union Carbide Corp.) discloses 2-aryl-1,3-cyclopentanedione compounds exhibiting acaricidal and herbicidal activity. WO 96/01798 (Bayer AG) and its derived U.S. Pat. No. 5,840,661 disclose 2-aryl-cyclopentane-1,3-dione derivatives and their use as pesticides and herbicides. WO 96/03366 (Bayer AG) and its derived U.S. Pat. No. 5,808,135 disclose fused 2-(2,4,6-trimethylphenyl) cyclopentane-1,3-dione derivatives and their use as pesticides and herbicides. WO 01/74770 (Bayer AG), its equivalent US 2003/0216260 A1, and its derived AU patent 782557 (AU 200144215C) disclose $C_2$-phenyl-substituted cyclic ketoenols and their use as pesticides and herbicides.

Copending patent application PCT/EP2009/058250, filed on 1 Jul. 2009 and published on 7 Jan. 2010 as WO 2010/000773 A1 (Syngenta Limited), discloses 5-(heterocyclylalkyl)-3-hydroxy-2-phenyl-cyclopent-2-enones, and their 2-phenyl-4-(heterocyclylalkyl)-cyclopentane-1,3-dione tautomers, as herbicides. Copending patent application PCT/EP2009/066712, filed on 9 Dec. 2009 and published on 24 Jun. 2010 as WO 2010/069834 A1 (Syngenta Participations AG and Syngenta Limited), discloses 2-phenyl-4-(heteroarylmethyl)-cyclopentane-1,3-diones as herbicides.

U.S. Pat. No. 5,684,205 (Bayer AG) discloses the use of substituted cyclopentane-diones and cyclopentane-triones for the preparation of medicaments which as chloride channel blockers are suitable for controlling airway diseases, secretory diarrhea and inflammatory diseases.

Novel cyclopentanedione, and derivatives thereof, having herbicidal and/or plant-growth-inhibiting properties, specifically 2-(substituted-phenyl)-cyclopentane-1,3-dione derivatives, have now been found.

The present invention accordingly relates to compounds of formula I

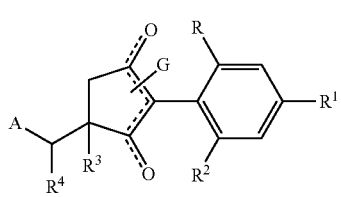

(I)

wherein:
R is methyl, ethyl, vinyl, ethynyl or cyclopropyl,
$R^1$ is hydrogen, $C_1$-$C_6$alkyl, $C_1$-$C_6$haloalkyl, $C_3$-$C_7$cycloalkyl, $C_1$-$C_6$alkoxy, $C_1$-$C_6$haloalkoxy, vinyl, propenyl, ethynyl, propynyl, halogen, phenyl, or phenyl substituted by alkyl (e.g. $C_1$-$C_4$alkyl), haloalkyl (e.g. $CF_3$, $CF_2Cl$, $CF_2H$, $CCl_2H$, $FCH_2$, $ClCH_2$, $BrCH_2$, $CH_3CHF$, $(CH_3)_2CF$, $CF_3CH_2$ or $CHF_2CH_2$), alkylsulfonyl (e.g. $C_1$-$C_4$alkylsulfonyl), halogen, nitro or cyano,
$R^2$ is methyl, ethyl, vinyl, ethynyl or methoxy,
$R^3$ and $R^4$ are hydrogen or together form a double bond,
A is $C_3$-$C_7$-cycloalkyl which is unsubstituted or substituted once or twice by $C_1$-$C_6$alkyl, $C_1$-$C_6$haloalkyl, $C_1$-$C_6$alkoxy, $C_1$-$C_6$alkylcarbonyloxy, $C_2$-$C_6$alkenyl, =O or =N—$R^{10}$, where $R^{10}$ is hydroxyl, $C_1$-$C_6$alkyl, $C_1$-$C_6$haloalkyl, $C_3$-$C_7$cycloalkyl, $C_1$-$C_6$alkoxy, $C_1$-$C_6$alkoxy$C_1$-$C_6$alkoxy or $C_1$-$C_6$haloalkoxy,
or A is cyclohexyl substituted once, at the 4-position (calculated with respect to the cyclohexyl connection point), by one ($C_3$-$C_6$cycloalkyl)methoxy, $C_3$-$C_6$cycloalkyloxy, $C_2$-$C_5$alkenyl-$CH_2$-oxy, benzyloxy, (monomethyl- or dimethyl-phenyl)methoxy, (monomethoxy- or dimethoxy-phenyl)methoxy or (monofluoro- or difluoro-phenyl)methoxy substituent,
or A is decahydro-1-naphthyl or decahydro-2-naphthyl,
or A is optionally substituted phenyl, and
G is hydrogen or an agriculturally acceptable metal, sulfonium, ammonium or latentiating group;
wherein, when G is a latentiating group, the latentiating group G is selected from the groups $C_1$-$C_8$alkyl, $C_2$-$C_8$haloalkyl, phenyl$C_1$-$C_8$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro), heteroaryl$C_1$-$C_8$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro) (for example, wherein the heteroaryl is pyridinyl or wherein the heteroaryl is a 5-membered monocyclic heteroaryl containing a N, O or S atom and optionally additionally 1, 2 or 3 N atoms), $C_3$-$C_8$alkenyl, $C_3$-$C_8$haloalkenyl, $C_3$-$C_8$alkynyl, $C(X^a)$—$R^a$, $C(X^b)$—$X^c$—$R^b$, $C(X^d)$—$N(R^c)$—$R^d$, —$SO_2$—$R^e$, —$P(X^e)(R^f)$—$R^g$ and $CH_2$—$X^f$—$R^h$;
wherein $X^a$, $X^b$, $X^c$, $X^d$, $X^e$ and $X^f$ are independently of each other oxygen or sulfur;
and wherein $R^a$ is H, $C_1$-$C_{18}$ alkyl (e.g. $C_1$-$C_6$alkyl or $C_1$-$C_4$alkyl such as tert-butyl or isopropyl), $C_2$-$C_{18}$ alkenyl, $C_2$-$C_{18}$ alkynyl, $C_1$-$C_{10}$haloalkyl (e.g. $C_1$-$C_{10}$fluoroalkyl), $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkyl-carbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl($C_1$-$C_5$)alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro) (e.g. wherein the heteroaryl is pyridinyl or wherein the heteroaryl is a 5-membered monocyclic heteroaryl containing a N, O or S atom and optionally additionally 1, 2 or 3 N atoms), $C_2$-$C_5$ haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, or heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or nitro (e.g. wherein the heteroaryl is pyridinyl or wherein the heteroaryl is a 5-membered monocyclic heteroaryl containing a N, O or S atom and optionally additionally 1, 2 or 3 N atoms);

$R^b$ is $C_1$-$C_{18}$alkyl (e.g. $C_1$-$C_6$alkyl or $C_1$-$C_4$alkyl such as $C_1$-$C_2$alkyl), $C_3$-$C_{18}$alkenyl, $C_3$-$C_{18}$alkynyl, $C_2$-$C_{10}$haloalkyl (e.g. $C_2$-$C_{10}$fluoroalkyl), $C_1$-$C_{10}$cyanoalkyl, $C_1$-$C_{10}$nitroalkyl, $C_2$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkyl-thio, $C_1$-$C_3$alkylsulfinyl, $C_1$-$C_3$alkylsulfonyl, halogen, cyano, or by nitro) (e.g. wherein the heteroaryl is pyridinyl or wherein the heteroaryl is a 5-membered monocyclic heteroaryl containing a N, O or S atom and optionally additionally 1, 2 or 3 N atoms), $C_3$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, or heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or nitro (e.g. wherein the heteroaryl is pyridinyl or wherein the heteroaryl is a 5-membered monocyclic heteroaryl containing a N, O or S atom and optionally additionally 1, 2 or 3 N atoms);

$R^c$ and $R^d$ are each independently of each other hydrogen, $C_1$-$C_{10}$alkyl (e.g. $C_1$-$C_6$alkyl or $C_1$-$C_4$alkyl such as $C_1$-$C_2$alkyl), $C_3$-$C_{10}$alkenyl, $C_3$-$C_{10}$alkynyl, $C_2$-$C_{10}$haloalkyl (e.g. $C_2$-$C_{10}$fluoroalkyl), $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_2$-$C_5$)alkylaminoalkyl, $C_3$-$C_6$trialkylsilyl($C_1$-$C_5$)alkyl, phenyl($C_1$-$C_5$)alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl($C_1$-$C_5$)alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro) (e.g. wherein the heteroaryl is pyridinyl or wherein the heteroaryl is a 5-membered monocyclic heteroaryl containing a N, O or S atom and optionally additionally 1, 2 or 3 N atoms), $C_2$-$C_5$ haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or nitro (e.g. wherein the heteroaryl is pyridinyl or wherein the heteroaryl is a 5-membered monocyclic heteroaryl containing a N, O or S atom and optionally additionally 1, 2 or 3 N atoms), heteroarylamino or heteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro (e.g. wherein the heteroaryl is pyridinyl or wherein the heteroaryl is a 5-membered monocyclic heteroaryl containing a N, O or S atom and optionally additionally 1, 2 or 3 N atoms), diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro (e.g. wherein the heteroaryl is pyridinyl or wherein the heteroaryl is a 5-membered monocyclic heteroaryl containing a N, O or S atom and optionally additionally 1, 2 or 3 N atoms), phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro or $C_3$-$C_7$cycloalkylamino, di-$C_3$-$C_7$cycloalkylamino or $C_3$-$C_7$cycloalkoxy;

or $R^c$ and $R^d$ may join together to form a 3-7 membered ring, optionally containing one heteroatom selected from O or S;

$R^e$ is $C_1$-$C_{10}$alkyl (e.g. $C_1$-$C_6$alkyl or $C_1$-$C_4$alkyl such as $C_1$-$C_2$alkyl), $C_2$-$C_{10}$alkenyl, $C_2$-$C_{10}$alkynyl, $C_1$-$C_{10}$haloalkyl (e.g. $C_1$-$C_{10}$fluoroalkyl), $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl($C_1$-$C_5$)alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro) (e.g. wherein the heteroaryl is pyridinyl or wherein the heteroaryl is a 5-membered monocyclic heteroaryl containing a N, O or S atom and optionally additionally 1, 2 or 3 N atoms), $C_2$-$C_5$ haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro (e.g. wherein the heteroaryl is pyridinyl or wherein the heteroaryl is a 5-membered monocyclic heteroaryl containing a N, O or S atom and optionally additionally 1, 2 or 3 N atoms), heteroarylamino or heteroarylamino substituted by $C_1$-$C_3$alkyl, $C_1$-$C_3$haloalkyl, $C_1$-$C_3$alkoxy, $C_1$-$C_3$haloalkoxy, halogen, cyano or by nitro (e.g. wherein the heteroaryl is pyridinyl or wherein the heteroaryl is a 5-membered monocyclic heteroaryl containing a N, O or S atom and optionally additionally 1, 2 or 3 N atoms), diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro (e.g. wherein the heteroaryl is pyridinyl or wherein the heteroaryl is a 5-membered monocyclic heteroaryl containing a N, O or S atom and optionally additionally 1, 2 or 3 N atoms), phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, diphenylamino, or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or $C_3$-$C_7$cycloalkylamino, di$C_3$-$C_7$cycloalkylamino or $C_3$-$C_7$cycloalkoxy, $C_1$-$C_{10}$alkoxy, $C_1$-$C_{10}$haloalkoxy, $C_1$-$C_5$alkylamino or $C_2$-$C_8$dialkylamino;

$R^f$ and $R^g$ are each independently of each other $C_1$-$C_{10}$alkyl (e.g. $C_1$-$C_6$alkyl or $C_1$-$C_4$alkyl such as $C_1$-$C_2$alkyl), $C_2$-$C_{10}$alkenyl, $C_2$-$C_{10}$alkynyl, $C_1$-$C_{10}$alkoxy, $C_1$-$C_{10}$haloalkyl (e.g. $C_1$-$C_{10}$fluoroalkyl), $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkyl-carbonyl-N—($C_2$-$C_5$)alkylaminoalkyl, $C_3$-$C_6$trialkylsilyl($C_1$-$C_5$)alkyl, phenyl($C_1$-$C_5$)alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl($C_1$-$C_5$)alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro) (e.g. wherein the heteroaryl is pyridinyl or wherein the heteroaryl is a 5-membered monocyclic heteroaryl containing a N, O or S atom and optionally additionally 1, 2 or 3 N atoms), $C_2$-$C_5$ haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro (e.g. wherein the heteroaryl is pyridinyl or wherein the heteroaryl is a 5-membered monocyclic heteroaryl containing a N, O or S atom and optionally additionally 1, 2 or 3 N atoms), heteroarylamino or heteroarylamino substituted by $C_1$-$C_3$alkyl, $C_1$-$C_3$haloalkyl, $C_1$-$C_3$alkoxy, $C_1$-$C_3$haloalkoxy, halogen, cyano or by nitro (e.g. wherein the heteroaryl is pyridinyl or wherein the heteroaryl is a 5-membered monocyclic heteroaryl containing a N, O or S atom and optionally additionally 1, 2 or 3 N atoms), diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro (e.g. wherein the heteroaryl is pyridinyl or wherein the heteroaryl is a 5-membered monocyclic heteroaryl containing a N, O or S atom and optionally additionally 1, 2 or 3 N atoms), phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, diphenylamino, or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or $C_3$-$C_7$cycloalkylamino, di$C_3$-$C_7$cycloalkylamino or $C_3$-$C_7$cycloalkoxy, $C_1$-$C_{10}$haloalkoxy, $C_1$-$C_5$alkylamino or $C_2$-$C_8$dialkylamino, benzyloxy or phenoxy, wherein the benzyl and phenyl groups may in turn be substituted by $C_1$-$C_3$alkyl, $C_1$-$C_3$haloalkyl, $C_1$-$C_3$alkoxy, $C_1$-$C_3$haloalkoxy, halogen, cyano or nitro; and $R^h$ is $C_1$-$C_{10}$alkyl (e.g. $C_1$-$C_6$alkyl or $C_1$-$C_4$alkyl such as $C_1$-$C_2$alkyl), $C_3$-$C_{10}$alkenyl, $C_3$-$C_{10}$alkynyl, $C_1$-$C_{10}$haloalkyl (e.g. $C_1$-$C_{10}$fluoroalkyl), $C_1$-$C_{10}$cyanoalkyl, $C_1$-$C_{10}$nitroalkyl, $C_2$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkyl-carbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro), heteroaryl($C_1$-$C_5$)alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro) (e.g. wherein the heteroaryl is pyridinyl or wherein the heteroaryl is a 5-membered monocyclic heteroaryl containing a N, O or S atom and optionally additionally 1, 2 or 3 N atoms), phenoxy($C_1$-$C_5$)alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro), heteroaryloxy($C_1$-$C_5$)alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro) (e.g. wherein the heteroaryl is pyridinyl or wherein the heteroaryl is a 5-membered monocyclic heteroaryl containing a N, O or S atom and optionally additionally 1, 2 or 3 N atoms), $C_3$-$C_5$ haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$ haloalkoxy, halogen or by nitro, or heteroaryl, or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro (e.g. wherein the heteroaryl is pyridinyl or wherein the heteroaryl is a 5-membered monocyclic heteroaryl containing a N, O or S atom and optionally additionally 1, 2 or 3 N atoms).

Preferably, in the compound of formula (I),

R is methyl, ethyl, vinyl, ethynyl or cyclopropyl, $R^1$ is hydrogen, $C_1$-$C_6$alkyl, $C_1$-$C_6$haloalkyl, $C_3$-$C_7$cycloalkyl, $C_1$-$C_6$alkoxy, $C_1$-$C_6$haloalkoxy, vinyl, propenyl, ethynyl, propynyl, halogen, phenyl, or phenyl substituted by alkyl (e.g. $C_1$-$C_4$alkyl), haloalkyl (e.g. $CF_3$, $CF_2Cl$, $CF_2H$, $CCl_2H$, $FCH_2$, $ClCH_2$, $BrCH_2$, $CH_3CHF$, $(CH_3)_2CF$, $CF_3CH_2$ or $CHF_2CH_2$), alkylsulfonyl (e.g. $C_1$-$C_4$alkylsulfonyl), halogen, nitro or cyano, $R^2$ is methyl, ethyl, vinyl, ethynyl or methoxy, $R^3$ and $R^4$ are hydrogen or together form a double bond, A is $C_3$-$C_7$-cycloalkyl which is unsubstituted or substituted once or twice by $C_1$-$C_6$alkyl, $C_1$-$C_6$haloalkyl, $C_1$-$C_6$alkoxy, $C_1$-$C_6$alkylcarbonyloxy, $C_2$-$C_6$alkenyl, =O or =N—$R^{10}$, where $R^{10}$ is hydroxyl, $C_1$-$C_6$alkyl, $C_1$-$C_6$haloalkyl, $C_3$-$C_7$cycloalkyl, $C_1$-$C_6$alkoxy, $C_1$-$C_6$alkoxy$C_1$-$C_6$alkoxy or $C_1$-$C_6$haloalkoxy, or A is optionally substituted phenyl, and G is hydrogen or an agriculturally acceptable metal, sulfonium, ammonium, or latentiating group,
wherein the latentiating group is as defined herein (e.g. hereinabove).

In the substituent definitions of the compounds of the formula I, each alkyl moiety either alone or as part of a larger group (such as alkoxy, alkylthio, alkoxycarbonyl, alkylcarbonyl, alkylsulfonyl, alkylaminocarbonyl, dialkylaminocarbonyl or cycloalkylalkyl) is a straight or branched chain and is, for example, independently methyl, ethyl, n-propyl, n-butyl, n-pentyl, n-hexyl, isopropyl, n-butyl, sec-butyl, isobutyl, tert-butyl or neopentyl. The alkyl groups are suitably $C_1$-$C_6$alkyl groups, but are preferably $C_1$-$C_4$alkyl or $C_1$-$C_3$alkyl groups, and, more preferably, $C_1$-$C_2$alkyl groups.

Alkenyl moieties can be in the form of straight or branched chains, and the alkenyl moieties, where appropriate, can be of either the (E)- or (Z)-configuration. Examples are vinyl and allyl. Alkenyl moieties can contain one or more double bonds in any combination.

Halogen is fluorine, chlorine, bromine or iodine, preferably fluorine, chlorine or bromine.

Haloalkyl groups are alkyl groups which are substituted with one or more of the same or different halogen atoms (e.g. fluorine atoms) and can independently be, for example, $CF_3$, $CF_2Cl$, $CF_2H$, $CCl_2H$, $FCH_2$, $ClCH_2$, $BrCH_2$, $CH_3CHF$, $(CH_3)_2CF$, $CF_3CH_2$ or $CHF_2CH_2$. In a more particular embodiment, the haloalkyl groups are $CF_3$, $CF_2H$, $FCH_2$, $CH_3CHF$, $(CH_3)_2CF$, $CF_3CH_2$ or $CHF_2CH_2$.

Cycloalkyl includes preferably and independently cyclopropyl, cyclobutyl, cyclopentyl, cyclohexyl and cycloheptyl.

The invention relates also to the agriculturally acceptable salts which the compounds of formula I are able to form with transition metal, alkali metal or alkaline earth metal bases, amines, quaternary ammonium bases or tertiary sulfonium bases.

Among the transition metal, alkali metal or alkaline earth metal bases capable of forming transition metal, alkali metal or alkaline earth metal salts (i.e. where G is a metal), special mention should be made of the hydroxides of copper, iron, lithium, sodium, potassium, magnesium or calcium; and preferably the hydroxides, bicarbonates or carbonates of sodium or potassium.

Examples of amines suitable for ammonium salt formation (i.e. where G is an ammonium) include ammonia, or primary, secondary or tertiary $C_1$-$C_{18}$alkylamines, $C_1$-$C_4$ hydroxyalkylamines or $C_2$-$C_4$alkoxyalkyl-amines, for example methylamine, ethylamine, n-propylamine, isopropylamine, the four butylamine isomers, n-amylamine, isoamylamine, hexylamine, heptylamine, octylamine, nonylamine, decylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, di-isopropylamine, di-n-butylamine, di-n-amylamine, di-isoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-but-2-enylamine, n-pent-2-enylamine, 2,3-dimethylbut-2-enylamine, dibut-2-enylamine, n-hex-2-enylamine, propylenediamine, trimethylamine, triethylamine, tri-n-propylamine, tri-isopropylamine, tri-n-butylamine, tri-isobutylamine, tri-sec-butylamine, tri-n-amylamine, methoxyethylamine or ethoxyethylamine; or heterocyclic amines, for example pyridine, quinoline, isoquinoline, morpholine, piperidine, pyrrolidine, indoline, quinuclidine or azepine; or primary arylamines, for example anilines, methoxyanilines, ethoxyanilines, o-, m- or p-toluidines, phenylenediamines, benzidines, naphthylamines, or o-, m- or p-chloroanilines; but especially triethylamine, isopropylamine or di-isopropylamine.

Preferred quaternary ammonium bases suitable for salt formation (i.e. where G is an ammonium) correspond, for example, to the formula $[N(R_aR_bR_cR_d)]OH$, wherein $R_a$, $R_b$, $R_c$ and $R_d$ are each independently of the others hydrogen or $C_1$-$C_4$alkyl. Further suitable tetraalkylammonium bases with other anions can be obtained, for example, by anion exchange reactions.

Preferred tertiary sulfonium bases suitable for salt formation (i.e. where G is a sulfonium) correspond, for example, to the formula $[SR_eR_fR_g]OH$, wherein $R_e$, $R_f$ and $R_g$ are each independently of the others $C_1$-$C_4$alkyl. Trimethylsulfonium hydroxide is especially preferred. Suitable sulfonium bases may be obtained from the reaction of thioethers, in particular dialkylsulfides, with alkylhalides, followed by conversion to a suitable base, for example a hydroxide, by anion exchange reactions.

It should be understood that in those compounds of formula I, where G is a metal, ammonium or sulfonium as mentioned above and as such represents a cation, the corresponding negative charge is largely delocalised across the O—C=C—C=O unit.

The compounds of formula I according to the invention also include hydrates, e.g. hydrates which may be formed during salt formation.

The latentiating group G is selected to allow its removal by one or a combination of biochemical, chemical or physical processes to afford compounds of formula I where G is H before, during or following (preferably during or following) application to the treated area or plants. Examples of these processes include enzymatic cleavage (e.g. enzymatic cleavage of esters), chemical hydrolysis and photoloysis. Compounds bearing such latentiating groups G may, in some cases, offer certain advantage(s), such as: improved penetration of the cuticula of the plants treated; increased tolerance of crops; improved compatibility or stability in formulated mixtures containing other herbicides, herbicide safeners, plant growth regulators, fungicides and/or insecticides; or reduced leaching in soils; in particular improved penetration of the cuticula of the plants treated.

In the latentiating group G, preferably, $X^a$, $X^b$, $X^c$, $X^d$, $X^e$ and/or $X^f$ are oxygen. More preferably, all of $X^a$, $X^b$, $X^c$, $X^d$, $X^e$ and $X^f$ are oxygen.

Preferably, the latentiating group G is a group —$C(X^a)$—$R^a$ or —$C(X^b)$—$X^c$—$R^b$.

More preferably, the latentiating group G is a group —$C(X^a)$—$R^a$ or —$C(X^b)$—$X^c$—$R^b$, wherein $R^a$ is hydrogen or $C_1$-$C_{18}$alkyl (more preferably, hydrogen or $C_1$-$C_6$alkyl, still more preferably $C_1$-$C_6$alkyl, most preferably $C_1$-$C_4$alkyl such as tert-butyl or isopropyl), $R^b$ is $C_1$-$C_{18}$alkyl (more preferably, $C_1$-$C_6$alkyl, still more preferably $C_1$-$C_4$alkyl such as $C_1$-$C_2$alkyl), and the meanings of $X^a$, $X^b$ and $X^c$ are as defined above (more preferably, $X^a$, $X^b$ and $X^c$ are oxygen).

Depending on the nature of the substituents, compounds of formula I may exist in different isomeric forms. When G is hydrogen, for example, compounds of formula I may exist in different tautomeric forms (one dione tautomer and two different keto-enol tautomers), as shown in the following scheme:

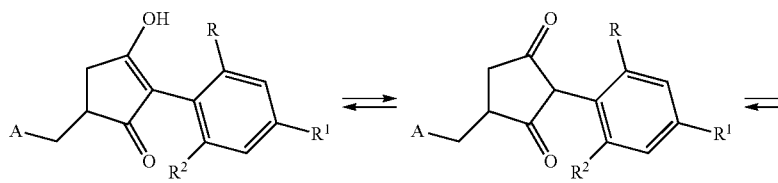 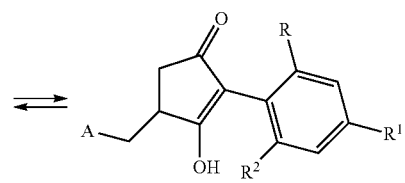

This invention covers all such isomers and tautomers and mixtures thereof in all proportions. Also, when substituents contain double bonds, cis- and trans-isomers can exist. These isomers, too, are within the scope of the claimed compounds of the formula I.

For the purpose of clarity, a compound of formula I, wherein G is H, is represented as a single tautomer, even if it is present in a different tautomeric form or as a mixture of tautomeric forms.

Preferably, in the compounds of formula I, substituent $R^1$ is hydrogen, $C_1$-$C_4$alkyl, halogen, $C_1$-$C_2$alkoxy, $C_1$-$C_2$haloalkoxy (e.g. difluoromethoxy), phenyl, or phenyl substituted by alkyl (e.g. $C_1$-$C_4$alkyl such as $C_1$-$C_2$alkyl), haloalkyl (e.g. $CF_3$, $CF_2Cl$, $CF_2H$, $CCl_2H$, $FCH_2$, $ClCH_2$, $BrCH_2$, $CH_3CHF$, $(CH_3)_2CF$, $CF_3CH_2$ or $CHF_2CH_2$; such as $CF_3$, $CF_2H$, $FCH_2$, $CH_3CHF$, $(CH_3)_2CF$, $CF_3CH_2$ or $CHF_2CH_2$; in particular trifluoromethyl), alkylsulfonyl (e.g. $C_1$-$C_4$alkylsulfonyl such as $C_1$-$C_2$alkylsulfonyl e.g. methanesulfonyl), halogen (e.g. fluorine, chlorine or bromine), nitro or cyano.

More preferably, $R^1$ is hydrogen, $C_1$-$C_4$alkyl (e.g. $C_1$-$C_2$alkyl) or halogen (e.g. fluorine, chlorine or bromine). Most preferably, $R^1$ is methyl.

Preferably, $R^2$ is methyl, ethyl or methoxy. More preferably, $R^2$ is methyl or ethyl, most preferably methyl.

Preferably, R is methyl or ethyl. Most preferably, R is methyl.

Preferably, $R^3$ and $R^4$ are hydrogen.

Preferably, A is $C_3$-$C_7$-cycloalkyl which is unsubstituted or substituted once or twice by $C_1$-$C_4$alkyl, $C_1$-$C_6$alkylcarbonyloxy, $C_4$-$C_6$alkenyl, =O or =N—$R^{10}$, where $R^{10}$ is hydroxyl or $C_1$-$C_4$alkoxy.

Preferably, $R^a$ is hydrogen or $C_1$-$C_{18}$alkyl. More preferably, $R^a$ is hydrogen or $C_1$-$C_6$alkyl, still more preferably $C_1$-$C_6$alkyl, most preferably $C_1$-$C_4$alkyl such as tert-butyl or isopropyl.

Preferably, $R^b$ is $C_1$-$C_{18}$alkyl. More preferably, $R^b$ is $C_1$-$C_6$alkyl, still more preferably $C_1$-$C_4$alkyl such as $C_1$-$C_2$alkyl.

Preferably, G is hydrogen or an agriculturally acceptable metal (in particular alkali metal or alkaline earth metal), sulfonium or ammonium group, or a latentiating group of the formula $C(X^a)$—$R^a$ or $C(X^b)$—$X^c$—$R^b$, wherein $X^a$ and $X^b$ are independently of each other oxygen or sulfur (more preferably oxygen), and $R^a$ and $R^b$ are as defined herein (e.g. hereinabove).

More preferably, G is hydrogen or an agriculturally acceptable metal (in particular alkali metal or alkaline earth metal), sulfonium or ammonium group, or a latentiating group of the formula $C(X^a)$—$R^a$ or $C(X^b)$—$X^c$—$R^b$, wherein $X^a$ and $X^b$ are independently of each other oxygen or sulfur (more preferably oxygen), and $R^a$ is hydrogen or $C_1$-$C_{18}$alkyl and $R^b$ is $C_1$-$C_{18}$alkyl. More preferably, $R^a$ is hydrogen or $C_1$-$C_6$alkyl (still more preferably $C_1$-$C_4$alkyl such as tert-butyl or isopropyl) and/or $R^b$ is $C_1$-$C_6$alkyl (still more preferably $C_1$-$C_4$alkyl such as $C_1$-$C_2$alkyl).

It is especially preferred for G to be hydrogen or pivaloyl (C(O)-tert-butyl).

In a preferred group of compounds of formula I, $R^1$ is hydrogen, $C_1$-$C_6$alkyl or halogen, $R^2$ is methyl, $R^3$ and $R^4$ are hydrogen or together form a double bond, A is $C_3$-$C_7$-cycloalkyl which is unsubstituted or substituted once or twice by $C_1$-$C_6$alkyl, $C_1$-$C_6$alkylcarbonyloxy, $C_2$-$C_6$alkenyl, =O or =N—$R^{10}$, where $R^{10}$ is hydroxyl or $C_1$-$C_6$alkoxy, and G is hydrogen or a latentiating group.

More preferably, in the compound of formula I, $R^1$ is hydrogen, methyl or bromo, $R^2$ is methyl, $R^3$ and $R^4$ are hydrogen, A is $C_5$- or $C_6$-cycloalkyl which is unsubstituted or substituted once or twice by methyl, propenyl, methylcarbonyloxy, =O or =N—$R^{10}$, where $R^{10}$ is hydroxyl or methoxy, and G is hydrogen or pivaloyl (C(O)-tert-butyl).

In one preferable embodiment of the invention (as disclosed in Tables 1, 2, 3, 4, 5, 6a, 7, 8, 9, 10, 11, 12, 13 and 14 hereinafter), the compound of formula (I) is a compound of formula (IA):

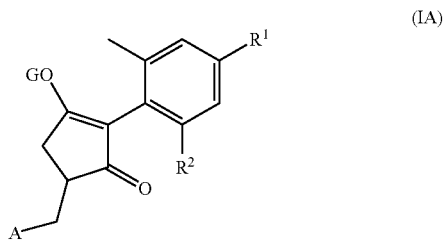

wherein G is hydrogen;
$R^2$ is $CH_3$ or $CH_3O$;
$R^1$ is H, $CH_3$, $CH_2CH_3$, F, Cl, Br, $CH_3O$, $CH_3CH_2O$, —CH=$CH_2$, —CCH, phenyl, 2-fluorophenyl, 2-chlorophenyl, 2-trifluoromethylphenyl, 2-nitrophenyl, 2-methylphenyl, 2-methanesulfonylphenyl, 2-cyanophenyl, 3-fluorophenyl, 3-chlorophenyl, 3-trifluoromethylphenyl, 3-nitrophenyl, 3-methylphenyl, 3-methanesulfonylphenyl, 3-cyanophenyl, 4-fluorophenyl, 4-chlorophenyl, 4-bromophenyl, 4-difluoromethoxyphenyl, 2-fluoro-4-chlorophenyl, 3-fluoro-4-chlorophenyl, 2-chloro-4-chlorophenyl, 2-chloro-4-fluorophenyl, 3-chloro-4-chlorophenyl, 3-chloro-4-fluorophenyl, 2-methyl-4-chlorophenyl, 4-trifluoromethylphenyl, 4-nitrophenyl, 4-methylphenyl, 4-methanesulfonylphenyl, or 4-cyanophenyl; and
A is of sub-formula (i), (ii), (iii), (iv), (v), (vi), (vii), (viii), (ix), (x), (xi), (xii), (xiii) or (xiv):

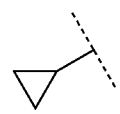

(i)

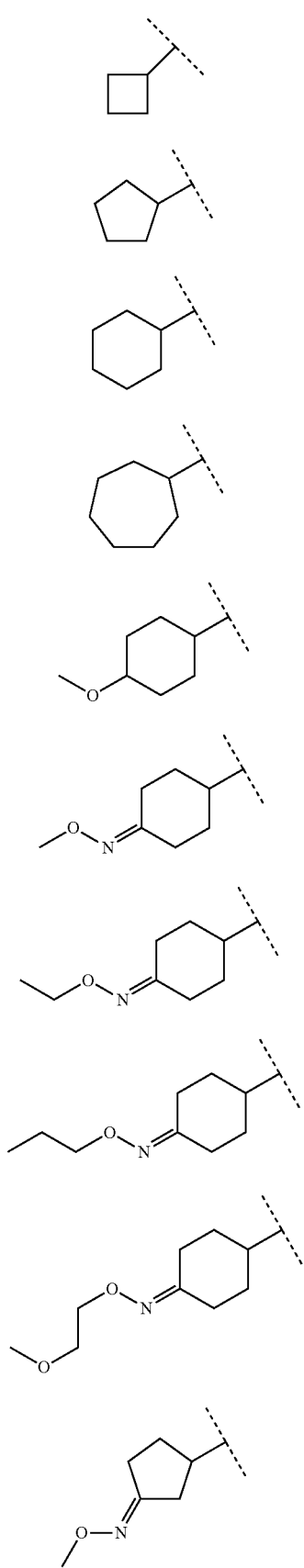

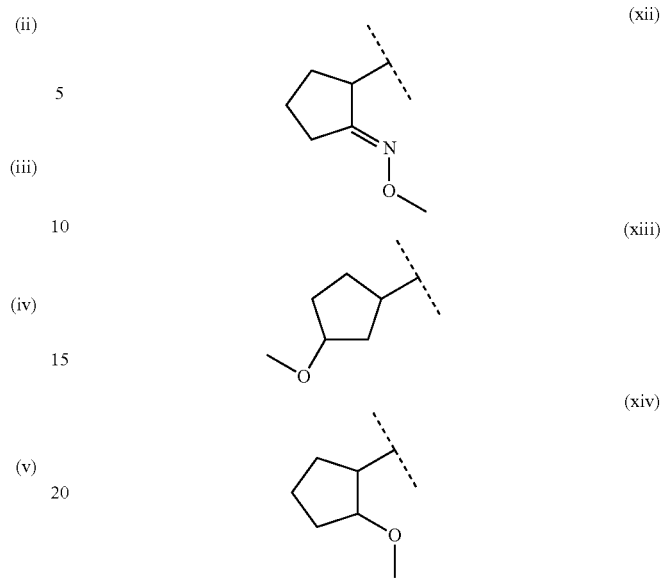

In the compound of formula (IA), preferably, A is of sub-formula (iii), (iv), (vi) or (vii); more preferably, A is of sub-formula (vi) or (vii).

The compound of formula (IA) is preferably one of compounds A2, A3, A9, A10, A11 or A38 as shown in Table A1 hereinafter.

In an alternative preferable embodiment of the invention (as disclosed in Tables 15, 16, 17, 18, 19, 20 and 21 hereinafter and/or Table A1 (Compounds A13 to A24) and/or Table B1 (Compounds B7 to B19) hereinafter), when A is optionally substituted phenyl, then, either:

(a) the compound of formula (I) is a compound of formula (IB):

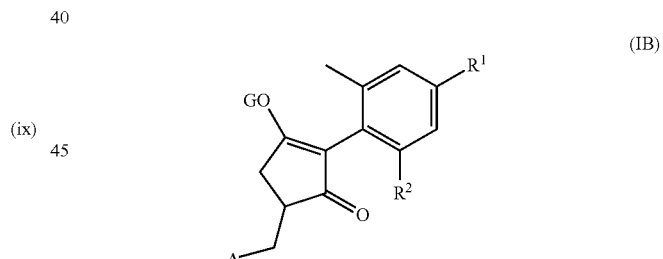

wherein:
G is hydrogen;
$R^2$ is $CH_3$ or $CH_3O$;
$R^1$ is H, $CH_3$, $CH_2CH_3$, F, Cl, Br, $CH_3O$, $CH_3CH_2O$, —CH=$CH_2$, —CCH, phenyl, 2-fluorophenyl, 2-chlorophenyl, 2-trifluoromethylphenyl, 2-nitrophenyl, 2-methylphenyl, 2-methanesulfonylphenyl, 2-cyanophenyl, 3-fluorophenyl, 3-chlorophenyl, 3-trifluoromethylphenyl, 3-nitrophenyl, 3-methylphenyl, 3-methanesulfonylphenyl, 3-cyanophenyl, 4-fluorophenyl, 4-chlorophenyl, 4-bromophenyl, 4-difluoromethoxyphenyl, 2-fluoro-4-chlorophenyl, 3-fluoro-4-chlorophenyl, 2-chloro-4-chlorophenyl, 2-chloro-4-fluorophenyl, 3-chloro-4-chlorophenyl, 3-chloro-4-fluorophenyl, 2-methyl-4-chlorophenyl, 4-trifluoromethylphenyl, 4-nitrophenyl, 4-methylphenyl, 4-methanesulfonylphenyl, or 4-cyanophenyl; and A is of sub-formula (xv), (xvi), (xvii), (xviii), (xix), (xx) or (xxi):
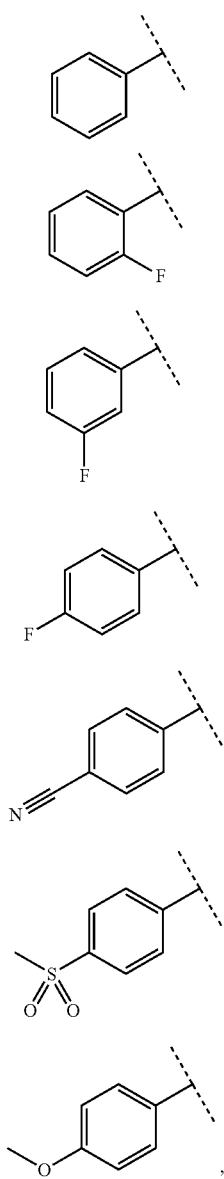
(xv)
(xvi)
(xvii)
(xviii)
(xix)
(xx)
(xxi)
or
(b) the compound is one of the following compounds A13, A15, A16, A18, A20, A21, A22, B7, B8, B9, B10, B11, B12, B13, B14, B15, B16, B17, B18 or B19:
(A13)
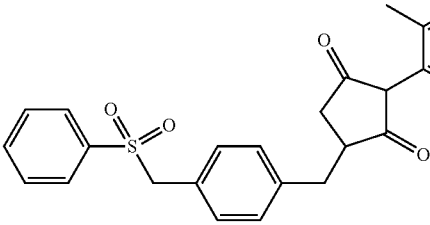
(A15)
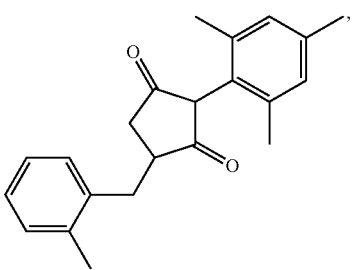
(A16)
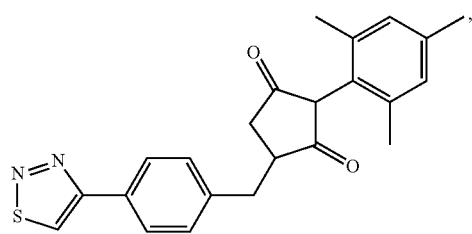
(A18)
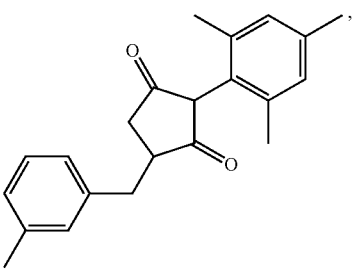
(A20)
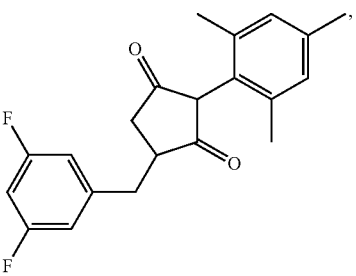
(A21)
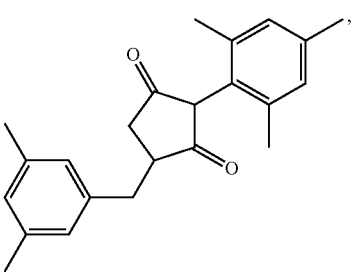
(A22)

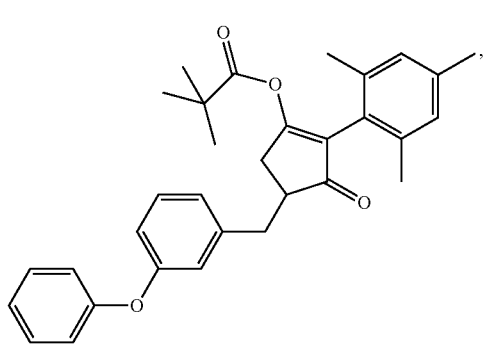
(B7)
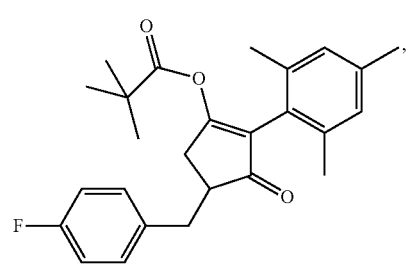
(B8)
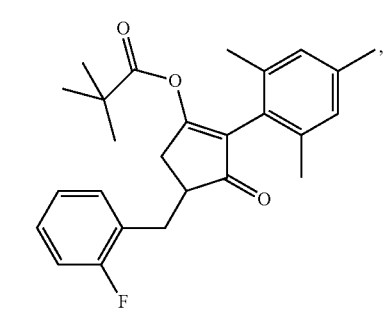
(B9)
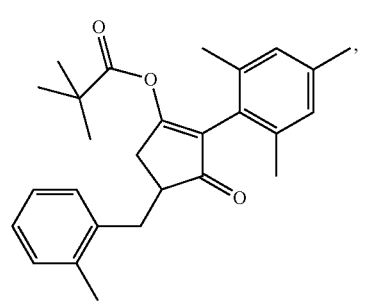
(B10)
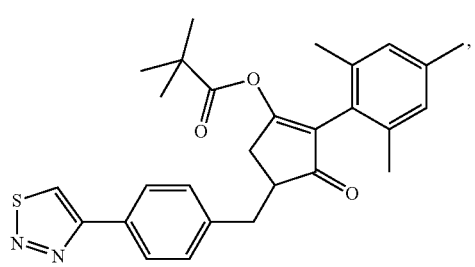
(B11)
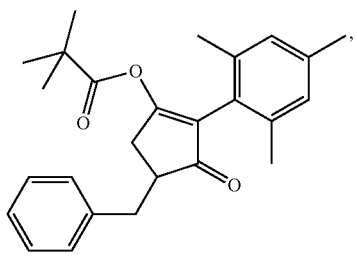
(B12)
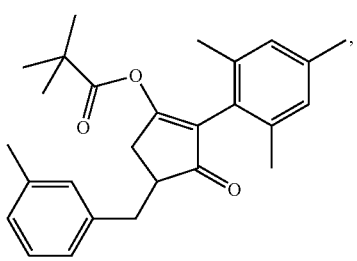
(B13)
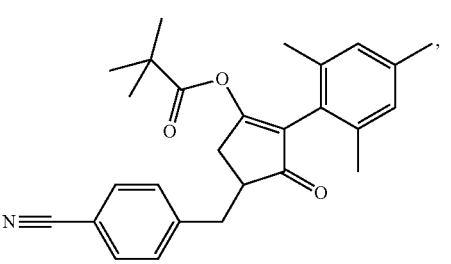
(B14)
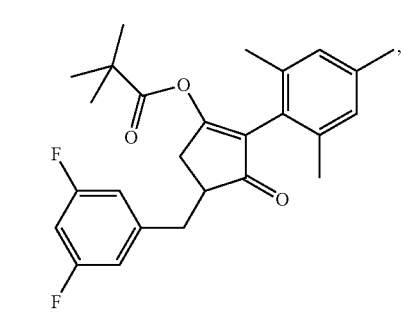
(B15)
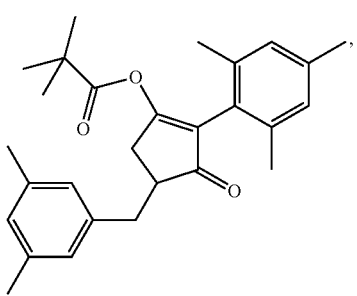
(B16)

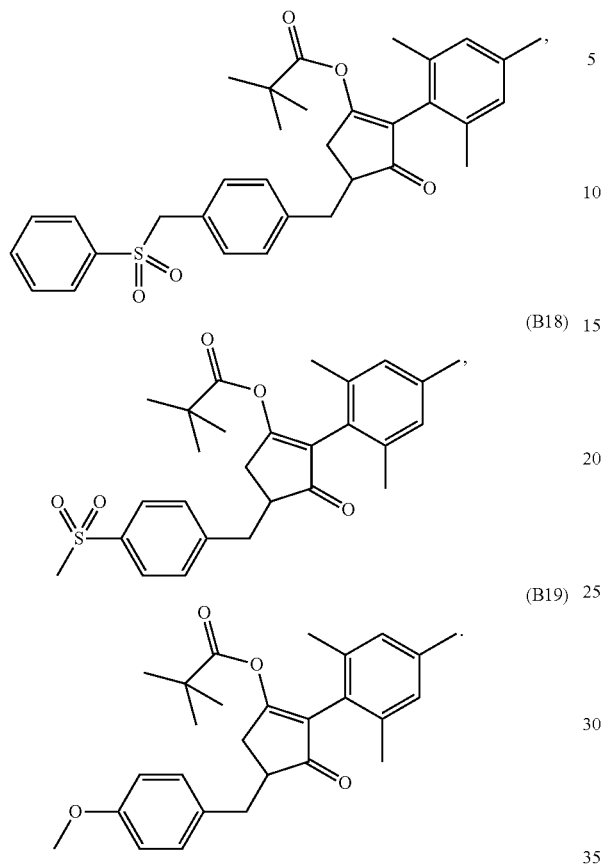

(B17)

(B18)

(B19)

Similarly, in the compound of formula (I), when A is optionally substituted phenyl, then, in a preferable embodiment, either (a):
G is hydrogen;
R is methyl;
$R^2$ is $CH_3$ or $CH_3O$;
$R^1$ is H, $CH_3$, $CH_2CH_3$, F, Cl, Br, $CH_3O$, $CH_3CH_2O$, —CH=$CH_2$, —CCH, phenyl, 2-fluorophenyl, 2-chlorophenyl, 2-trifluoromethylphenyl, 2-nitrophenyl, 2-methylphenyl, 2-methanesulfonylphenyl, 2-cyanophenyl, 3-fluorophenyl, 3-chlorophenyl, 3-trifluoromethylphenyl, 3-nitrophenyl, 3-methylphenyl, 3-methanesulfonylphenyl, 3-cyanophenyl, 4-fluorophenyl, 4-chlorophenyl, 4-bromophenyl, 4-difluoromethoxyphenyl, 2-fluoro-4-chlorophenyl, 3-fluoro-4-chlorophenyl, 2-chloro-4-chlorophenyl, 2-chloro-4-fluorophenyl, 3-chloro-4-chlorophenyl, 3-chloro-4-fluorophenyl, 2-methyl-4-chlorophenyl, 4-trifluoromethylphenyl, 4-nitrophenyl, 4-methylphenyl, 4-methanesulfonylphenyl, or 4-cyanophenyl;
$R^3$ and $R^4$ are both hydrogen; and
A is of sub-formula (xv), (xvi), (xvii), (xviii), (xix), (xx) or (xxi):

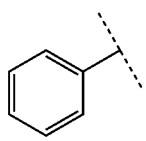

(xv)

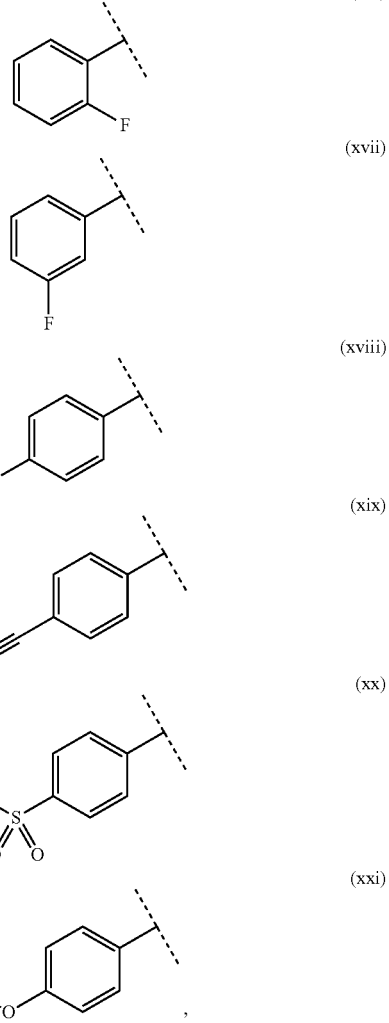

(xvi)

(xvii)

(xviii)

(xix)

(xx)

(xxi)

or
(b) the compound is one of the compounds A13, A15, A16, A18, A20, A21, A22, B7, B8, B9, B10, B11, B12, B13, B14, B15, B16, B17, B18 or B19 as defined herein (e.g. hereinabove).

In another alternative preferable embodiment of the invention (as disclosed in Tables 6b, 6c, 6d, 6e, 6f, 6g, 6h, and 6i hereinafter), the compound of formula (I) is a compound of formula (IC):

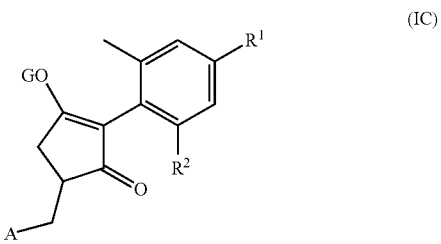

(IC)

wherein G is hydrogen;
$R^2$ is $CH_3$ or $CH_3O$;
$R^1$ is H, $CH_3$, $CH_2CH_3$, F, Cl, Br, $CH_3O$, $CH_3CH_2O$, —CH=$CH_2$, —CCH, phenyl, 2-fluorophenyl, 2-chlorophenyl, 2-trifluoromethylphenyl, 2-nitrophenyl, 2-methylphenyl, 2-methanesulfonylphenyl, 2-cyanophenyl, 3-fluorophenyl, 3-chlorophenyl, 3-trifluoromethylphenyl, 3-nitrophenyl, 3-methylphenyl, 3-methanesulfonylphenyl, 3-cyanophenyl, 4-fluorophenyl, 4-chlorophenyl, 4-bromophenyl, 4-difluoromethoxyphenyl, 2-fluoro-4-chlorophenyl, 3-fluoro-4-chlorophenyl, 2-chloro-4-chlorophenyl, 2-chloro-4-fluorophenyl, 3-chloro-4-chlorophenyl, 3-chloro-4-fluorophenyl, 2-methyl-4-chlorophenyl, 4-trifluoromethylphenyl, 4-nitrophenyl, 4-methylphenyl, 4-methanesulfonylphenyl, or 4-cyanophenyl; and A is of sub-formula (6b), (6c), (6d), (6e), (6f), (6g), (6h), or (6i):

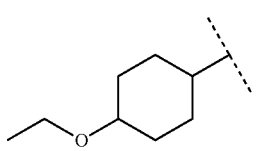
(6b)

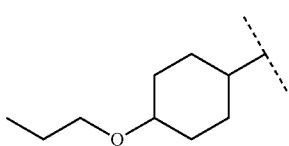
(6c)

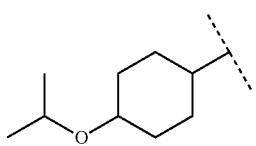
(6d)

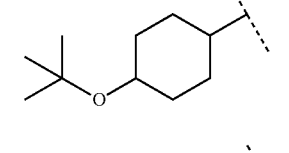
(6e)

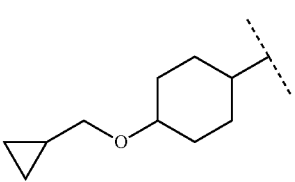
(6f)

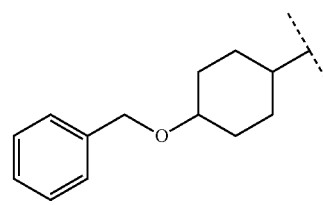
(6g)

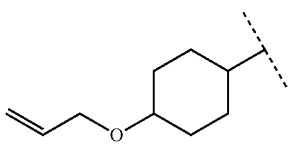
(6h)

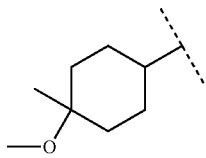
(6i)

The compound of formula (IC) is preferably one of Compounds A40 to A47 as shown in Table A1 hereinafter.

In the compounds of formulae (IA), (IB) and/or (IC), preferably, $R^1$ is H, $CH_3$, $CH_2CH_3$, F, Cl, or Br.

In the compounds of formulae (IA), (IB) and/or (IC), more preferably, $R^1$ is $CH_3$.

In the compounds of formulae (IA), (IB) and/or (IC), preferably, $R^2$ is $CH_3$ (methyl).

In a particularly preferable embodiment of the invention, the compound is one of Compounds A1 to A47, or B1 to B28, or C1 to C10, as defined by the structures shown in Table A1, Table B1 and Table C1 herein (hereinafter).

For example, the compound is preferably one of Compounds A1 to A24, A38, or B1 to B19, as defined by the structures shown in Table A1 and Table B1 herein (hereinafter).

Alternatively, the compound is preferably one of Compounds A25 to A37, A39 to A47, B20 to B28, or C1 to C10, as defined by the structures shown in Table A1, Table B1 and Table C1 herein (hereinafter).

Certain compounds of formula (I) are alkenes, and as such may undergo hydrogenation to give additional compounds of formula (I) according to known procedures.

Those skilled in the art will appreciate that compounds of formula (I) may contain a aromatic moiety bearing one or more substituents capable of being transformed into alternative substituents under known conditions, and that these compounds may themselves serve as intermediates in the preparation of additional compounds of formula (I).

For example, compounds of formula (I) wherein $R^1$ is alkenyl or alkynyl, may be reduced to compounds of formula (I) wherein $R^1$ is alkyl under known conditions and compounds of formula (I) wherein $R^1$ is halogen, preferably bromide or iodine, may undergo a cross-coupling reaction with a suitable coupling partner under conditions described in the literature for Suzuki-Miyaura, Sonogashira and related cross-coupling reactions to give additional compounds of formula (I) (see, for example, O'Brien, C. J. and Organ, M. G. Angew. Chem. Int. Ed. (2007), 46, 2768-2813; Suzuki, A. Journal of Organometallic Chemistry (2002), 653, 83; Miyaura N. and Suzuki, A. Chem. Rev. (1995), 95, 2457-2483).

In one embodiment, compounds of formula (I), wherein G is $C_1$-$C_8$alkyl, $C_2$-$C_8$haloalkyl, phenyl$C_1$-$C_8$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsufinyl, $C_1$-$C_3$alkylsulfonyl, halogen, cyano or by nitro), heteroaryl$C_1$-$C_8$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsufinyl, $C_1$-$C_3$alkylsulfonyl, halogen, cyano or by nitro), $C_3$-$C_8$alkenyl, $C_3$-$C_8$haloalkenyl, $C_3$-$C_8$alkynyl, $C(X^a)$—$R^a$, $C(X^b)$—$X^c$—$R^b$, $C(X^d)$—N($R^c$)—$R^d$, —$SO_2$—$R^e$, —P($X^e$)($R^f$)—$R^g$ or $CH_2$—$X^f$—$R^h$ where $X^a$, $X^b$, $X^c$, $X^d$, $X^e$, $X^f$, $R^a$, $R^b$, $R^c$, $R^d$, $R^e$, $R^f$, $R^g$ and $R^h$ are as defined above, are prepared by treating compounds of formula (A), which are compounds of formula (I) wherein G is H, with a reagent G-Z, wherein G-Z is an alkylating agent such as an alkyl halide (the definition of alkyl halides includes simple $C_1$-$C_8$ alkyl halides such as methyl iodide and ethyl iodide, substituted alkyl halides such as chloromethyl alkyl ethers, Cl—$CH_2$—$X^f$—$R^h$, wherein $X^f$ is oxygen, and chloromethyl alkyl sulfides Cl—$CH_2$—$X^f$—$R^h$, wherein $X^f$ is sulfur), a $C_1$-$C_8$alkyl sulfonate, or a di-$C_1$-$C_8$alkyl sulfate, or with a $C_3$-$C_8$alkenyl halide, or with a $C_3$-$C_8$alkynyl halide, or with an acylating agent such as a carboxylic acid, HO—C($X^a$)$R^a$, wherein $X^a$ is oxygen, an acid chloride, Cl—C($X^a$)$R^a$, wherein $X^a$ is oxygen, or acid anhydride, $[R^aC(X^a)]_2O$, wherein $X^a$ is oxygen, or an isocyanate, $R^cN$=C=O, or a carbamoyl chloride, Cl—C($X^d$)—N($R^c$)—$R^d$ (wherein $X^d$ is oxygen and with the proviso that neither $R^c$ nor $R^d$ is hydrogen), or a thiocarbamoyl chloride Cl—C($X^d$)—N($R^c$)—$R^d$ (wherein $X^d$ is sulfur and with the proviso that neither $R^c$ nor $R^d$ is hydrogen) or a chloroformate, Cl—C($X^b$)—$X^c$—$R^b$, (wherein $X^b$ and $X^c$ are oxygen), or a chlorothioformate Cl—C($X^b$)—$X^c$—$R^b$ (wherein $X^b$ is oxygen and $X^c$ is sulfur), or a chlorodithioformate Cl—C($X^b$)—$X^c$—$R^b$, (wherein $X^b$ and $X^c$ are sulfur), or an isothiocyanate, $R^cN$=C=S, or by sequential treatment with carbon disulfide and an alkylating agent, or with a phosphorylating agent such as a phosphoryl chloride, Cl—P($X^e$)($R^f$)—$R^g$ or with a sulfonylating agent such as a sulfonyl chloride Cl—$SO_2$—$R^e$, preferably in the presence of at least one equivalent of base.

Isomeric compounds of formula (I) may be formed. For example, compounds of formula (A) may give rise to two isomeric compounds of formula (I), or to isomeric mixtures of compounds of formula (I). This invention covers both isomeric compounds of formula (I), together with mixtures of these compounds in any ratio.

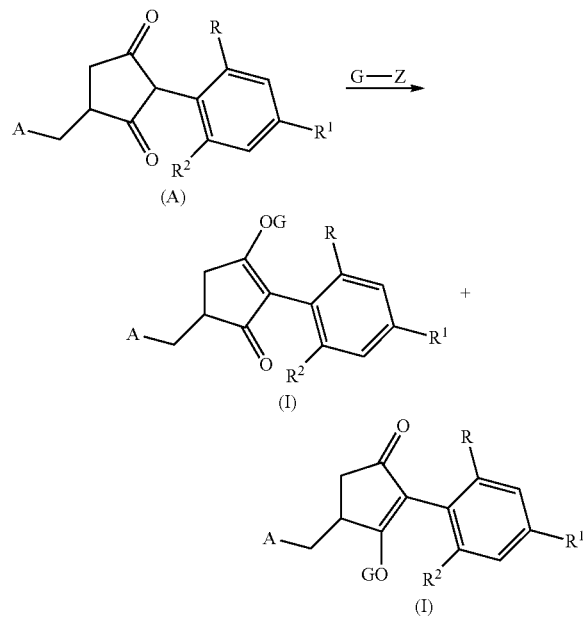

The O-alkylation of cyclic 1,3-diones is known; suitable methods are described, for example, in U.S. Pat. No. 4,436,666. Alternative procedures have been reported by Pizzorno, M. T. and Albonico, S. M. Chem. Ind. (London) (1972), 425; Born, H. et al. J. Chem. Soc. (1953), 1779; Constantino, M. G. et al. Synth. Commun. (1992), 22 (19), 2859; Tian, Y. et al. Synth. Commun. (1997), 27 (9), 1577; Chandra Roy, S. et al., Chem. Lett. (2006), 35 (1), 16; Zubaidha, P. K. et al. Tetrahedron Lett. (2004), 45, 7187 and by Zwanenburg, B. et al. Tetrahedron (2005), 45 (22), 7109.

The acylation of cyclic 1,3-diones may be effected by procedures similar to those described, for example, in U.S. Pat. No. 4,551,547, U.S. Pat. No. 4,175,135, U.S. Pat. No. 4,422,870, U.S. Pat. No. 4,659,372 and U.S. Pat. No. 4,436,666. Typically diones of formula (A) may be treated with the acylating agent in the presence of at least one equivalent of a suitable base, optionally in the presence of a suitable solvent. The base may be inorganic, such as an alkali metal carbonate or hydroxide, or a metal hydride, or an organic base such as a tertiary amine or metal alkoxide. Examples of suitable inorganic bases include sodium carbonate, sodium or potassium hydroxide, sodium hydride, and suitable organic bases include trialkylamines, such as trimethylamine and triethylamine, pyridines or other amine bases such as 1,4-diazobicyclo[2.2.2]octane and 1,8-diazabicyclo[5.4.0]undec-7-ene. Preferred bases include triethylamine and pyridine. Suitable solvents for this reaction are selected to be compatible with the reagents and include ethers such as tetrahydrofuran and 1,2-dimethoxyethane and halogenated solvents such as dichloromethane and chloroform. Certain bases, such as pyridine and triethylamine, may be employed successfully as both base and solvent. For cases where the acylating agent is a carboxylic acid, acylation is preferably effected in the presence of a coupling agent such as 2-chloro-1-methylpyridinium iodide, N,N'-dicyclohexylcarbodiimide, 1-(3-dimethylaminopropyl)-3-ethylcarbodiimide and N,N'-carbodiimidazole, and optionally a base such as triethylamine or pyridine in a suitable solvent such as tetrahydrofuran, dichloromethane or acetonitrile. Suitable procedures are described, for example, by Zhang, W. and Pugh, G. Tetrahedron Lett. (1999), 40 (43), 7595 and Isobe, T. and Ishikawa, T. J. Org. Chem. (1999), 64 (19) 6984.

Phosphorylation of cyclic-1,3-diones may be effected using a phosphoryl halide or thiophosphoryl halide and a base by procedures analogous to those described in U.S. Pat. No. 4,409,153.

Sulfonylation of compounds of formula (A) may be achieved using an alkyl or aryl sulfonyl halide, preferably in the presence of at least one equivalent of base, for example by the procedure of Kowalski, C. J. and Fields, K. W. J. Org. Chem. (1981), 46, 197.

Compounds of formula (A) may be prepared from compounds of formula (I) by hydrolysis, preferably in the presence of an acid catalyst such as hydrochloric acid and optionally in the presence of a suitable solvent such as tetrahydrofuran or acetone preferably between 25° C. and 150° C. under conventional heating or under microwave irradiation. Alternatively compounds of formula (A) may be prepared from compounds of formula (I) by dealkylation under heating in morpholine preferably between 25° C. and 200° C. under conventional heating or under microwave irradiation as described in WO0435588 and also by Stevens, K. L. et al, Bioorg. Med. Chem. Lett. (2008), 18, 5758.

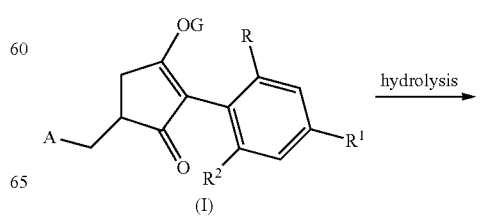

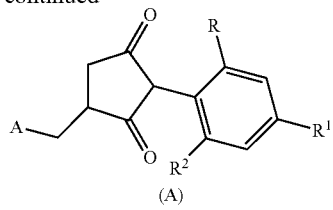

In a further approach, compounds of formula (A) may be prepared by the cyclisation of a compound of formula (B) or a compound of formula (C), wherein R' is hydrogen or an alkyl group, preferably in the presence of an acid or base, and optionally in the presence of a suitable solvent, by analogous methods to those described by T. N. Wheeler, U.S. Pat. No. 4,209,532. Compounds of formula (B) or compounds of formula (C) wherein R' is hydrogen may be cyclised under acidic conditions, preferably in the presence of a strong acid such as sulfuric acid, polyphosphoric acid or Eaton's reagent, optionally in the presence of a suitable solvent such as acetic acid, toluene or dichloromethane.

Compounds of formula (B) or compounds of formula (C) wherein R' is alkyl (preferably methyl or ethyl), may be cyclised under acidic or basic conditions, preferably in the presence of at least one equivalent of a strong base such as potassium tert-butoxide, lithium diisopropylamide or sodium hydride and in a solvent such as tetrahydrofuran, toluene, dimethylsulfoxide or N,N-dimethylformamide.

Compounds of formula (B) and compounds of formula (C), wherein R' is H, may be esterified to, respectively, compounds of formula (B) and compounds of formula (C), wherein R' is alkyl, under standard conditions, for example by heating with an alkyl alcohol, ROH, in the presence of an acid catalyst.

Compounds of formula (B) and compounds of formula (C), wherein R' is H, may be prepared, respectively, by saponification of a compounds of formula (D) and compounds of formula (E) wherein R' is alkyl (preferably methyl or ethyl), under standard conditions, followed by acidification of the reaction mixture to effect decarboxylation, by similar processes to those described, for example, by T. N. Wheeler, U.S. Pat. No. 4,209,532.

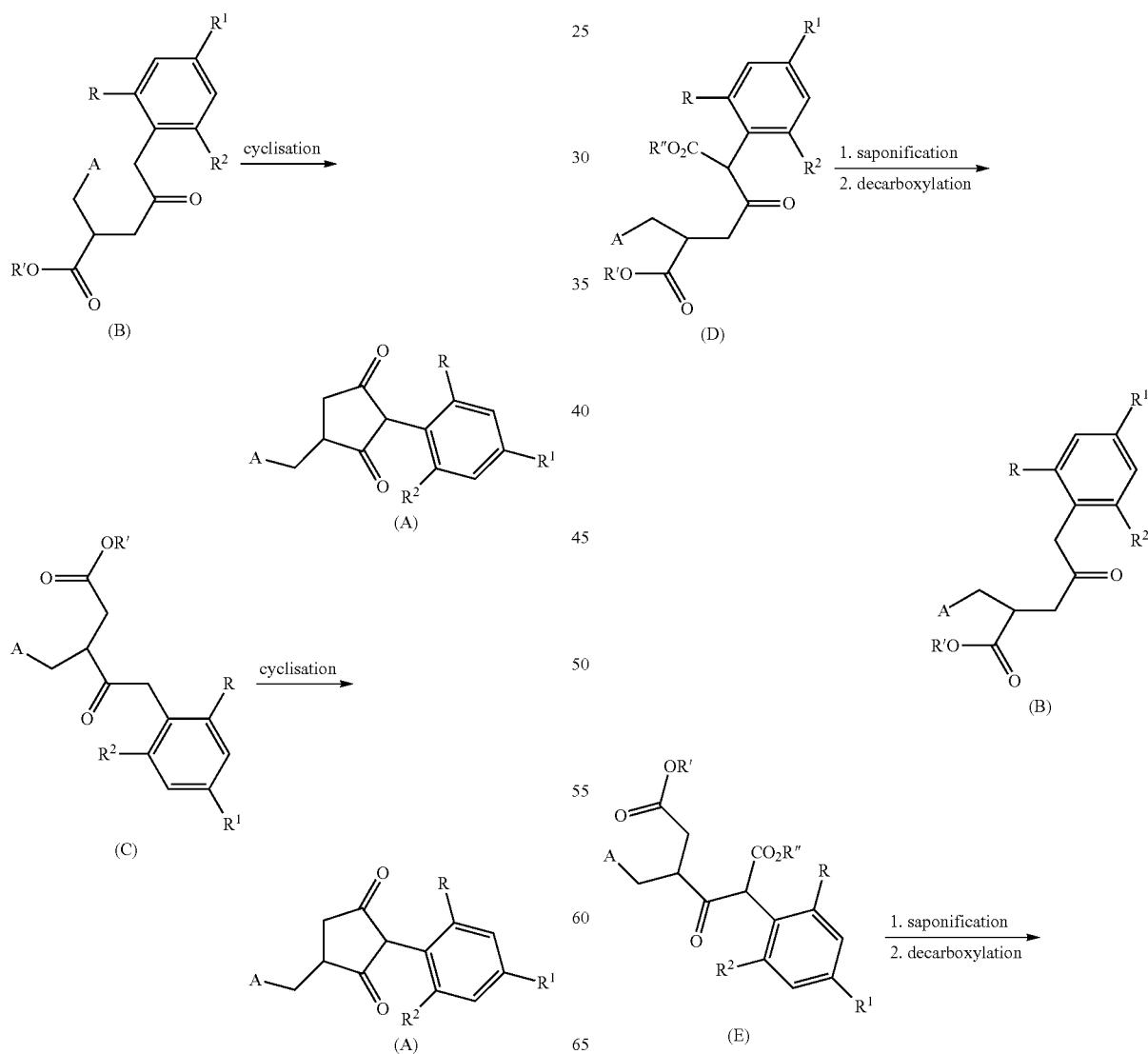

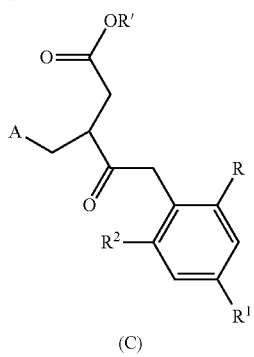

(C)

Compounds of formula (D) and compounds of formula (E), wherein R" is alkyl, may be prepared by treating, respectively, compounds of formula (F) with suitable carboxylic acid chlorides of formula (G) or suitable carboxylic acid chlorides of formula (H) under basic conditions. Suitable bases include potassium tert-butoxide, sodium bis(trimethylsilyl)amide and lithium diisopropylamide and the reaction is preferably conducted in a suitable solvent (such as tetrahydrofuran or toluene) at a temperature of between −80° C. and 30° C. Alternatively, compounds of formula (D) and compounds of formula (E), wherein R" is H, may be prepared by treating a compound of formula (F) with a suitable base (such as potassium tert-butoxide, sodium bis(trimethylsilyl)amide and lithium diisopropylamide) in a suitable solvent (such as tetrahydrofuran or toluene) at a suitable temperature (between −80° C. and 30° C.) and reacting the resulting anion with a suitable anhydride of formula (J):

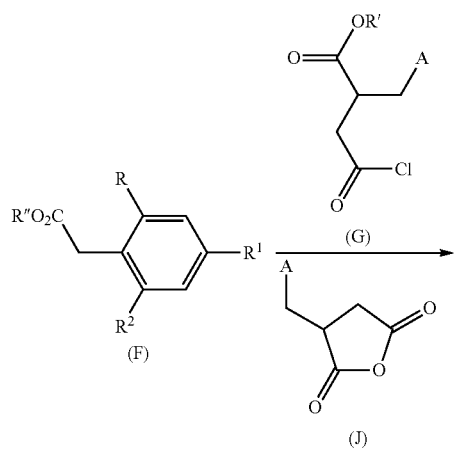

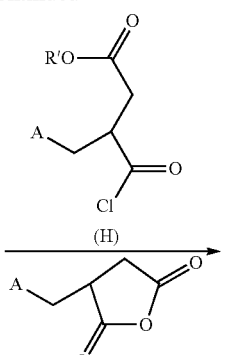

(F)

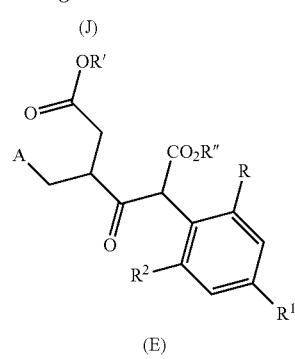

(E)

Compounds of formula (F) are known compounds, or may be prepared from known compounds by known methods.

Compounds of formula (J) are known see for example Arnold, R. T. and Showell J. S. J. Am. Chem. Soc. (1957), 79 (2), 419-422; Ballini, R. et al. Synthesis (2002), (5), 681-685 or may be prepared, for example, by analogous methods to those described by Bergmeier, S. C. and Ismail, K. A. Synthesis (2000), (10), 1369-1371; Groutas, W. C. et al. J. Med. Chem. (1989), 32 (7), 1607-11 and Bernhard, K. and Lincke, H. Helv. Chim. Acta (1946), 29, 1457-1466.

Compounds of formula (G) or compounds of formula (H) may be prepared from a compound of formula (J) by treatment with an alkyl alcohol, R'—OH, in the presence of a base, such as dimethylaminopyridine or an alkaline metal alkoxide (see, for example, Buser, S, and Vasella, A. Helv. Chim. Acta, (2005), 88, 3151 and M. Hart et al. Bioorg. Med. Chem. Letters, (2004), 14, 1969), followed by treatment of the resulting acid with a chlorinating reagent such as oxalyl chloride or thionyl chloride under known conditions (see, for example, Santelli-Rouvier. C. Tetrahedron Lett. (1984), 25 (39), 4371; Walba D. and Wand, M. Tetrahedron Lett. (1982), 23 (48), 4995; Cason, J. Org. Synth. Coll. Vol. III, (169), 1955).

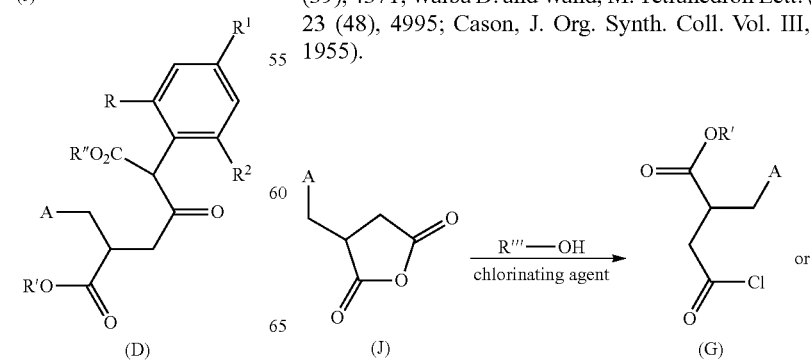

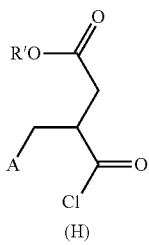

(H)

Compounds of formula (G) and compounds of formula (H) may be made from known compounds by known methods. For example, analogous methods to obtain compounds of formula (G) and compounds of formula (H) are described by Bergmeier, S. C. and Ismail, K. A. Synthesis (2000), (10), 1369-1371.

In an further approach, compounds of formula (I) may be prepared by treating compounds of formula (K) with compounds of formula (L) wherein LG is a leaving group such as halogen (preferably iodide or bromide) or an activated alcohol (preferably mesylate or tosylate) under basic conditions. Suitable bases include lithium diisopropylamide, sodium hexamethyldisilazide, potassium tert-butoxide and the reaction is preferably conducted in a suitable solvent (such as tetrahydrofuran) at a temperature between −80° C. and 30° C.

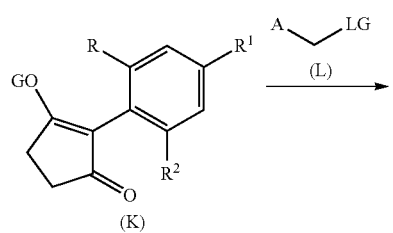

(K)

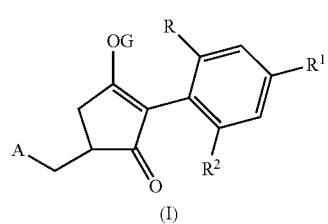

(I)

Compounds of formula (L) are known, or may be made known compounds by known methods.

Compounds of formula (K) are known compounds or may be made from known compounds by known methods (see, for example, Song, Y. S. S. et al. Tetrahedron Lett. (2005), 46 (46), 5987-5990; Kuethe, J. T. et al. J. Org. Chem. (2002), 67(17), 5993-6000).

Alternatively, compounds of formula (K) wherein G is $C_1$-$C_6$alkyl may be prepared by alkylation of compounds of formula (K), wherein G is hydrogen under known conditions or by known methods (see, for example, Eberhardt, U. et al. Chem. Ber. (1983), 116 (1), 119-135).

Compounds of formula (K), wherein G is hydrogen, are known, or may be prepared from known compounds by known methods (see, for example, Nguyen, H. N. et al. J. Am. Chem. Soc. (2003), 125 (39), 11818-11819; Bonjoch, J. et al. Tetrahedron (2001), 57(28), 6011-6017; Fox, J. M. et al. J. Am. Chem. Soc. (2000), 122(7), 1360-1370; U.S. Pat. No. 4,338,122; U.S. Pat. No. 4,283,348).

Alternatively, compounds of formula (I) having a double bond may be prepared from compounds of formula (M) by known methods (see, for example, Habib-Zahmani, H. et al. Synlett (2007), (7), 1037-1042; Nagaoka, H. et al. Tetrahedron Letters (1985), 26 (41), 5053-5056; Nagaoka, H. et al. J. Am. Chem. Soc. (1986), 108 (16), 5019-5021; Zuki, M. et al. Bull. Chem. Soc. Japan (1988), 61(4), 1299-1312; Enholm, E. J. et al. J. Org. Chem. (1996), 61 (16), 5384-5390; Clive, D. L. J. et al. Tetrahedron (2001), 57 (18), 3845-3858; Bartoli, G. et al. J. Org. Chem. (2002), 67 (25), 9111-9114. Jung, M. E. et al. Chem. Comm. (2003), (2), 196-197; EP1433772; JP2004203844; IN194295).

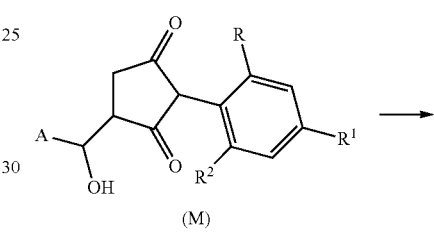

(M)

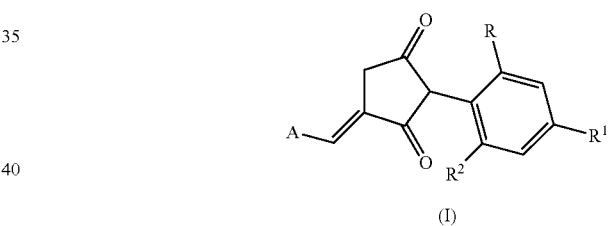

(I)

Compounds of formula (M) may be prepared by treating compounds of formula (K) (in which G is hydrogen) with compounds of formula (N) under basic conditions. Suitable bases include lithium diisopropylamide, sodium hexamethyldisilazide, potassium tert-butoxide and the reaction is preferably conducted in a suitable solvent (such as tetrahydrofuran) at a temperature between −80° C. and 30° C.

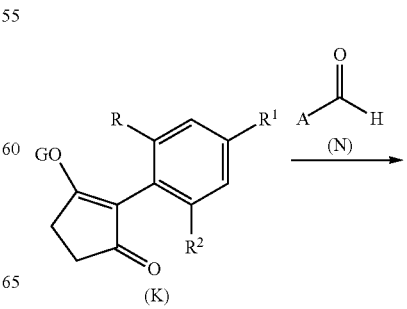

(K)

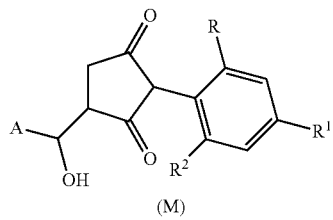

(M)

Compounds of formula (N) are known, or may be made from known compounds by known methods.

Compounds of formula (I) (wherein G is $C_1$-$C_4$alkyl) may be prepared by reacting compounds of formula (O) (wherein G is $C_1$-$C_4$alkyl, and Hal is a halogen, preferably bromine or iodine), with aryl boronic acids, Ar—B(OH)$_2$, of formula (P) in the presence of a suitable palladium catalyst (for example 0.001-50% palladium(II) acetate with respect to compound (O)) and a base (for example 1 to 10 equivalents potassium phosphate with respect to compound (O)) and preferably in the presence of a suitable ligand (for example 0.001-50% (2-dicyclohexylphosphino)-2',6'-dimethoxybiphenyl with respect to compound (O)), and in a suitable solvent (for example toluene or 1,2-dimethoxyethane), preferably between 25° C. and 200° C. under conventional heating or under microwave irradiation (see, for example, Song, Y. S. S. et al. Tetrahedron Lett. (2005), 46 (46), 5987-5990; Kuethe, J. T. et al. J. Org. Chem. (2002), 67(17), 5993-6000).

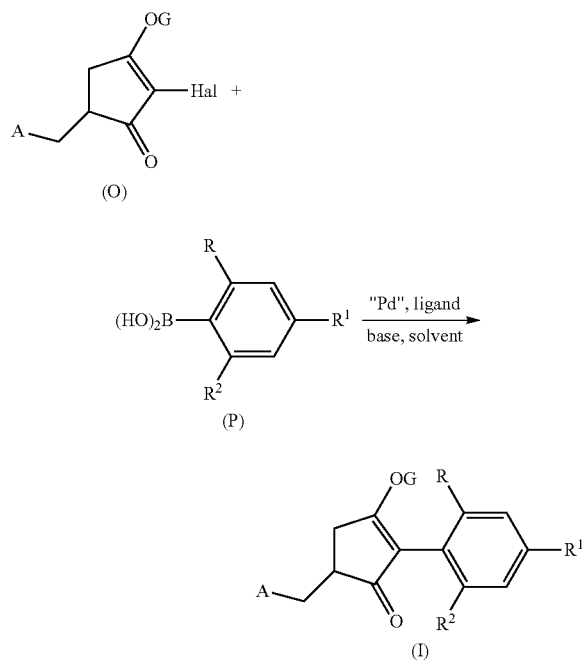

A compound of formula (O) may be prepared by halogenating a compound of formula (Q), followed by alkylation of the resulting halide of formula (R) with a $C_1$-$C_4$alkyl halide or tri-$C_1$-$C_4$alkylorthoformate under known conditions, for example by the procedures of Shepherd R. G. et al. J. Chem. Soc. Perkin Trans. 1 (1987), 2153-2155 and Lin Y.-L. et al. Bioorg. Med. Chem. (2002), 10, 685-690. Alternatively, compounds of formula (O) may be prepared by alkylating a compound of formula (Q) with a $C_{1-4}$ alkyl halide or a tri-$C_{1-4}$-alkylorthoformate, and halogenating the resulting enone of formula (S) under known conditions (see for example Song, Y. S. et al. Tetrahedron Lett. (2005), 46 (36), 5987-5990; Kuethe, J. T. et al. J. Org. Chem. (2002), 67(17), 5993-6000; Belmont, D. T. et al. J. Org. Chem. 1985, 50 (21), 4102-4107).

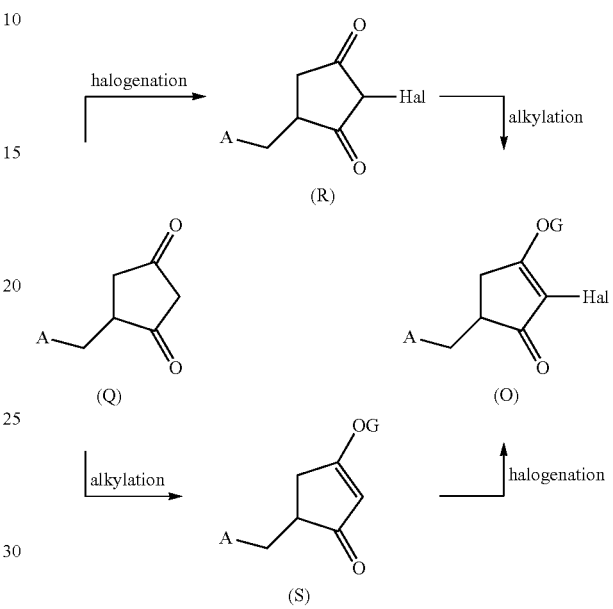

Compounds of formula (S) may be prepared by treating compounds of formula (T) with compounds of formula (L) wherein LG is a leaving group such as halogen (preferably iodide or bromide) or an activated alcohol (preferably mesylate or tosylate) under basic conditions. Suitable bases include lithium diisopropylamide, sodium hexamethyldisilazide, potassium tert-butoxide and the reaction is preferably conducted in a suitable solvent (such as tetrahydrofuran) at a temperature between −80° C. and 30° C. (see, for example, Gulias, M. et al. Org. Lett. (2003), 5(11), 1975-1977; Altenbach, R. J. et al. J. Med. Chem. (2006), 49 (23), 6869-6887; Snowden, R. L. Tetrahedron (1986), 42 (12), 3277-90; Oppolzer, W. et al. Helv. Chim. Acta (1980), 63 (4), 788-92; Mellor, M. et al. Synth. Commun. 1979, 9 (1), 1-4).

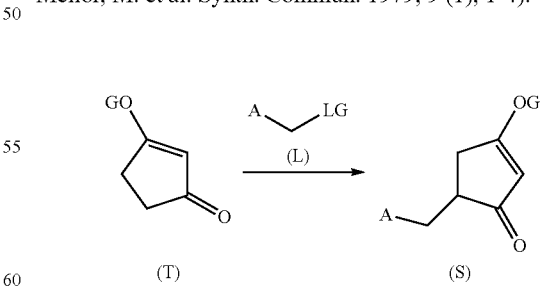

Compounds of formula (T) are known, or may be made from known compounds by known methods.

Alternatively compounds of formula (S) can be prepared by hydrogenation of compounds of formula (U) under known methods.

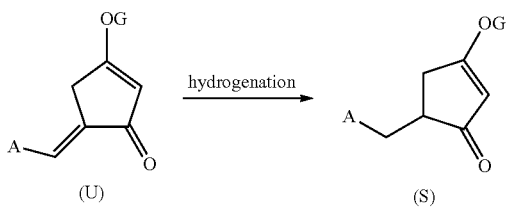

Compounds of formula (U) can be prepared hydrogenation of compounds of formula (U) under known methods from compounds of formula (V) by known methods (see, for example, Nagaoka, H. et al. Tetrahedron Letters (1985), 26 (41), 5053-5056; Nagaoka, H. et al. J. Am. Chem. Soc. (1986), 108 (16), 5019-5021; Zuki, M. et al. Bull. Chem. Soc. Japan (1988), 61(4), 1299-1312; Enholm, E. J. et al. J. Org. Chem. (1996), 61 (16), 5384-5390; Clive, D. L. J. et al. Tetrahedron (2001), 57 (18), 3845-3858; Bartoli, G. et al. J. Org. Chem. (2002), 67 (25), 9111-9114. Jung, M. E. et al. Chem. Comm. (2003), (2), 196-197; EP1433772; JP2004203844; IN194295).

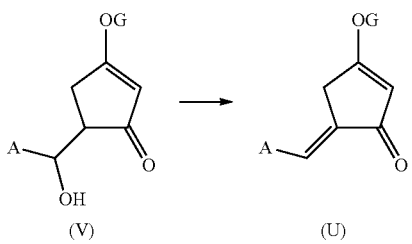

Compounds of formula (V) may be prepared by treating compounds of formula (T) with compounds of formula (N) under basic conditions. Suitable bases include lithium diisopropylamide, sodium hexamethyldisilazide, potassium tert-butoxide and the reaction is preferably conducted in a suitable solvent (such as tetrahydrofuran) at a temperature between −80° C. and 30° C. (see, for example, Aleman, J. et al. Chem. Comm. (2007), (38), 3921-3923).

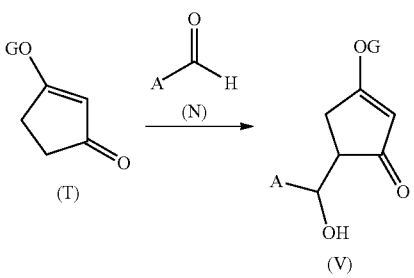

Compounds such as (N) are known and can be prepared by known methods. In particular, examples where A is a 4-alkoxycyclohexyl group (AH) can be prepared from ketones such as (AI) via methods such as that described by S. G. Pyne et al J. Am. Chem. Soc. (1982), 104, 5719. For example treatment of (methoxymethyl)triphenylphosphonium chloride with a strong base such as lithium diisopropylamide in a suitable solvent, preferably THF, at between −80° C. and 30° C. followed by addition of a ketone of formula (AI). The resultant solution may then be treated with a strong acid, preferably aqueous hydrochloric acid and heated at between 0° C. and 120° C.

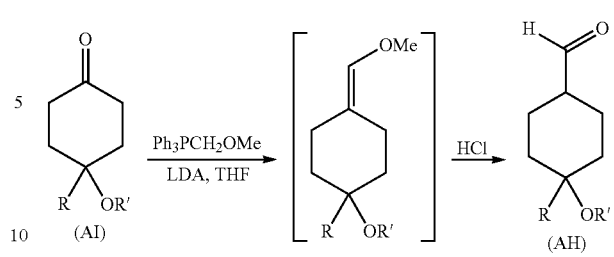

Ketones such as (AI) can be prepared via the methods described by D. Cooper et al in WO2007107566 and WO2008119716 from (AJ) by either reduction or addition of an alkylmetal species, followed by O-alkylation and deprotection.

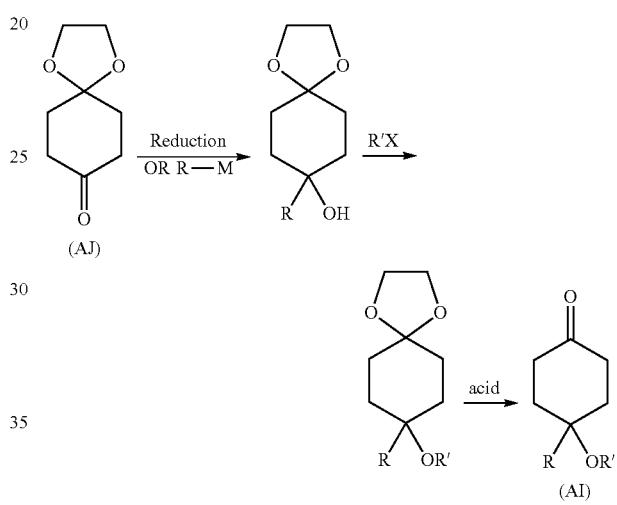

Compounds of formula (P) may be prepared from an aryl halide of formula (W), wherein Hal is bromine or iodine, by known methods (see, for example, Thompson W. et al. J. Org. Chem. (1984), 49, 5237 and R. Hawkins et al. J. Am. Chem. Soc. (1960), 82, 3053). For example, an aryl halide of formula (W) may be treated with an alkyl lithium or alkyl magnesium halide in a suitable solvent, preferably diethyl ether or tetrahydrofuran, at a temperature of between −80° C. and 30° C., and the aryl magnesium or aryl lithium reagent obtained may then be reacted with a trialkyl borate (preferably trimethylborate) to give an aryl dialkylboronate which may be hydrolysed to provide a boronic acid of formula (P) under acidic conditions.

Compounds of formula (P) may be prepared from an aryl halide of formula (W), wherein Hal is bromine or iodine, by known methods (see, for example, Thompson W. et al. J. Org. Chem. (1984), 49, 5237 and R. Hawkins et al. J. Am. Chem. Soc. (1960), 82, 3053). For example, an aryl halide of formula (W) may be treated with an alkyl lithium or alkyl magnesium halide in a suitable solvent, preferably diethyl ether or tetrahydrofuran, at a temperature of between −80° C. and 30° C., and the aryl magnesium or aryl lithium reagent obtained may then be reacted with a trialkyl borate (preferably trimethylborate) to give an aryl dialkylboronate which may be hydrolysed to provide a boronic acid of formula (P) under acidic conditions.

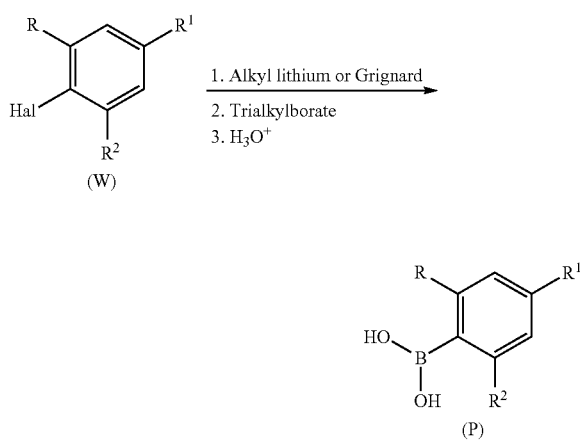

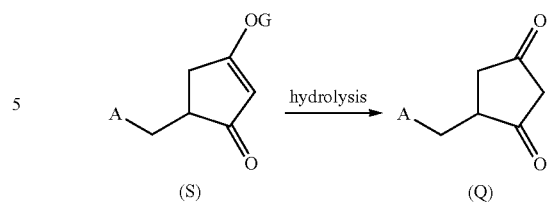

Alternatively a compound of formula (W) may be reacted with a cyclic boronate ester derived from a 1,2- or a 1,3-alkanediol such as pinacol, 2,2-dimethyl-1,3-propanediol and 2-methyl-2,4-pentanediol) under known conditions (see, for example, Miyaura N. et al. J. Org. Chem. (1995), 60, 7508, and Zhu W. et al. Org. Lett. (2006), 8 (2), 261), and the resulting boronate ester may be hydrolysed under acidic conditions to give a boronic acid of formula (P).

Aryl halides of formula (W) are known, or may be prepared from known compounds by known methods. For example, aryl halides of formula (W) may be prepared from anilines of formula (X) by known methods, for example: the Sandmeyer reaction, via the corresponding diazonium salts.

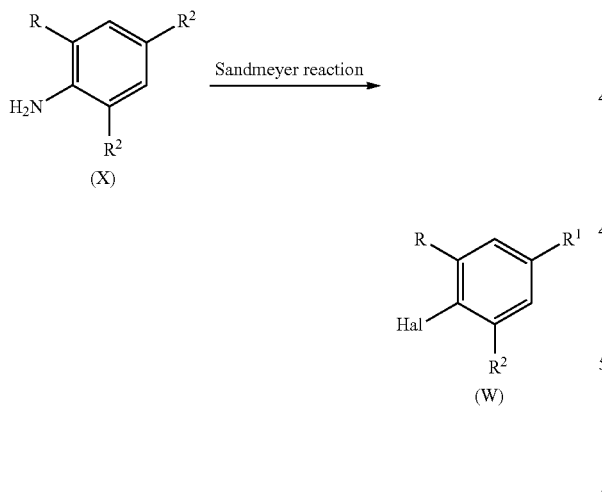

Anilines of formula (X) are known compounds, or may be made from known compounds, by known methods.

Alternatively compounds of formula (W) can be made by halogenations of the corresponding known compounds, by known methods.

Compounds of formula (Q) may be prepared from compounds of formula (S) by hydrolysis, preferably in the presence of an acid catalyst such as hydrochloric acid and optionally in the presence of a suitable solvent such as tetrahydrofuran or acetone preferably between 25° C. and 150° C. under conventional heating or under microwave irradiation.

Alternatively, compounds of formula (Q) can be made from known compounds by known methods (see for example Manukina, T. A. et al. Zhurnal Organicheskoi Khimii (1986), 22(4), 873-4; Mellor, M. et al. Synth. Commun. 1979, 9 (1), 1-4).

In a further approach, compounds of formula (A) may be prepared by reacting compounds of formula (Q) with suitable aryl halides (such as aryl-iodides, aryl-bromides or aryl-chlorides), Ar-Hal of formula (V), in the presence of a suitable palladium catalyst (for example 0.001-50% palladium(II) acetate with respect to compounds of formula (Q)) and a base (for example 1 to 10 equivalents potassium phosphate with respect to compounds of formula (Q)) and preferably in the presence of a suitable ligand (for example 0.001-50% (2-dicyclohexylphosphino)-2',4',6'-triisopropylbiphenyl with respect to compounds of formula (Q)), and in a suitable solvent (for example dioxane or 1,2-dimethoxyethane), preferably between 25° C. and 200° C. Similar couplings are known in the literature (see for example, Belmont, D. T. et al. J. Org. Chem. 1985, 50 (21), 4102-4107; Fox, J. M. et al. J. Am. Chem. Soc. (2000), 122 (7), 1360-1370; B. Hong et al. WO 2005/000233). Alternatively, compounds of formula (A) may be prepared by reacting compounds of formula (Q) with suitable aryl halides (such as an aryl-iodides), Ar-Hal of formula (V), in the presence of a suitable copper catalyst (for example 0.001-50% copper(I) iodide with respect to compounds of formula (Q)) and a base (for example 1 to 10 equivalents potassium carbonate with respect to compounds of formula (Q)) and preferably in the presence of a suitable ligand (for example 0.001-50% L-proline with respect to compounds of formula (Q)), and in a suitable solvent (for example dimethylsulfoxide), preferably between 25° C. and 200° C. Similar couplings are known in the literature for aryl halides (see, for example, Jiang, Y. et al. Synlett (2005), 18, 2731-2734).

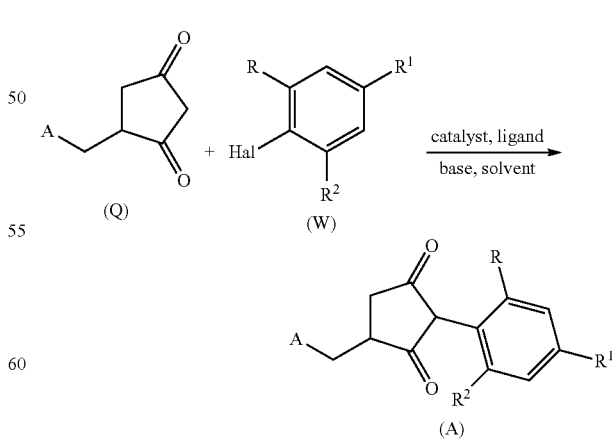

Additional compounds of formula (A) may be prepared by reacting compounds of formula (Q) with organolead reagents of formula (Y) under conditions described, for example, by Pinhey, J. Pure and Appl. Chem. (1996), 68 (4), 819 and by Moloney M. et al. Tetrahedron Lett. (2002), 43, 3407.

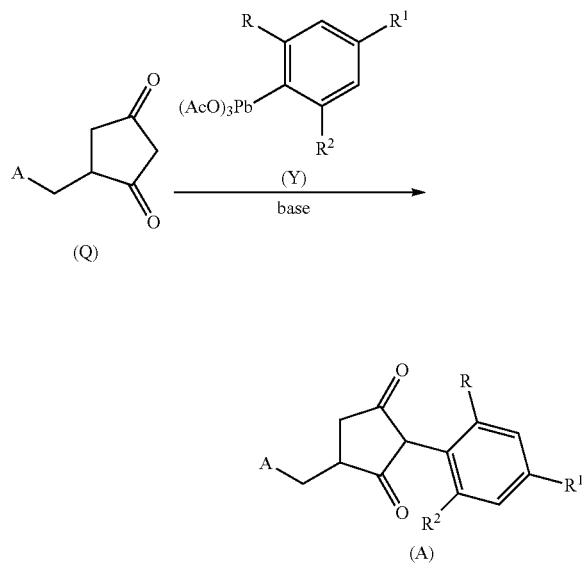

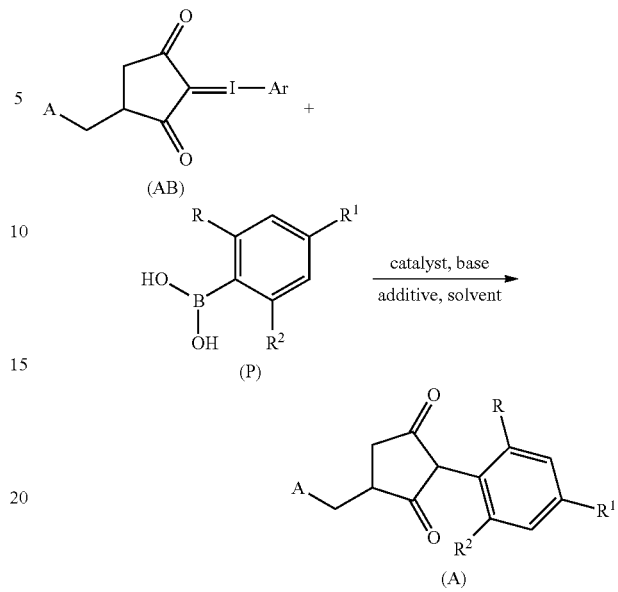

The organolead reagent of formula (X) may be prepared from a boronic acid of formula (P), a stannane of formula (Z), wherein R''' is $C_1$-$C_4$alkyl or by direct plumbation of a compound of formula (AA) with lead tetraacetate according to known procedures.

Suitable palladium catalysts are generally palladium(II) or palladium(0) complexes, for example palladium(II) dihalides, palladium(II) acetate, palladium(II) sulfate, bis(triphenylphosphine)palladium(II) dichloride, bis(tricyclopentylphosphine)palladium(II) dichloride, bis(tricyclohexylphosphine)palladium(II) dichloride, bis(dibenzylideneacetone)palladium(0) or tetrakis(triphenylphosphine)palladium(0). The palladium catalyst can also be prepared in situ from palladium(II) or palladium(0) compounds by complexing with the desired ligands, by,

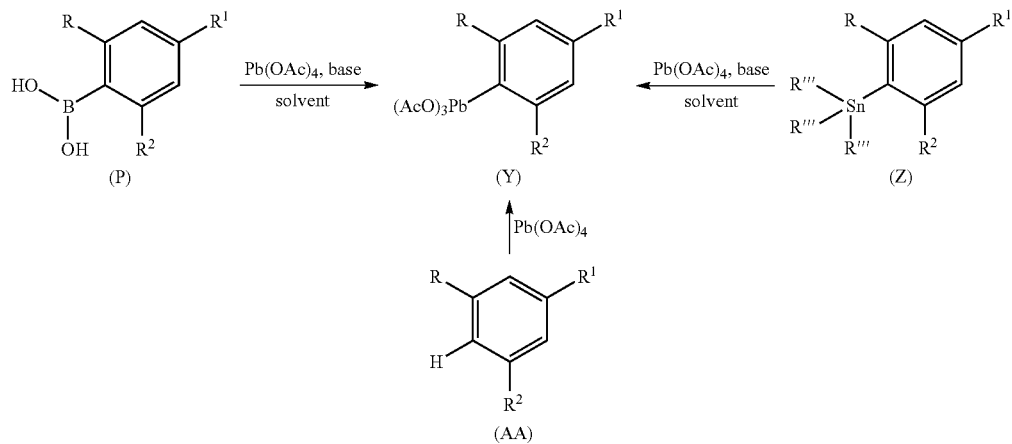

Further compounds of formula (A) may be prepared by reacting compounds of formula (Q) with suitable triarylbismuth compounds under conditions described, for example, by Fedorov, A. U. et al. Russ. Chem. Bull. Int. Ed. (2005), 54 (11), 2602 and by Koech P. et al. J. Am. Chem. Soc. (2004), 126 (17), 5350 and references therein.

Additional compounds of formula (A) may be prepared by reacting an iodonium ylide of formula (AB), wherein Ar is an optionally substituted phenyl group, and an aryl boronic acid of formula (P), in the presence of a suitable palladium catalyst, a base and in a suitable solvent.

for example, combining the palladium(II) salt to be complexed, for example palladium(II) dichloride ($PdCl_2$) or palladium(II) acetate ($Pd(OAc)_2$), together with the desired ligand, for example triphenylphosphine ($PPh_3$), tricyclopentylphosphine, tricyclohexylphosphine, 2-dicyclohexylphosphino-2',6'-dimethoxybiphenyl or 2-dicyclohexylphosphino-2',4',6'-triisopropylbiphenyl and the selected solvent, with a compound of formula (AB), the arylboronic acid of formula (P), and a base. Also suitable are bidendate ligands, for example 1,1'-bis(diphenylphosphino)ferrocene or 1,2-bis(diphenylphosphino)ethane. By heating the reaction medium, the palladium(II) complex or palladium(0) complex desired for the C—C coupling reaction is thus formed in situ, and then initiates the C—C coupling reaction.

The palladium catalysts are used in an amount of from 0.001 to 50 mol %, preferably in an amount of from 0.1 to 15 mol %, based on the compound of formula (AA). The reaction may also be carried out in the presence of other additives, such as tetralkylammonium salts, for example, tetrabutylammonium bromide. Preferably the palladium catalyst is palladium acetate, the base is lithium hydroxide and the solvent is aqueous 1,2-dimethoxyethane.

A compound of formula (AB) may be prepared from a compound of formula (Q) by treatment with a hypervalent iodine reagent such as a (diacetoxy)iodobenzene or an iodosylbenzene and a base such as aqueous sodium carbonate, lithium hydroxide or sodium hydroxide in a solvent such as water or an aqueous alcohol such as aqueous ethanol according to the procedures of Schank K. et al. Synthesis (1983), 392, Moriarty R. M. et al. J. Am. Chem. Soc. (1985), 107, 1375 or of Yang Z. et al. Org. Lett. (2002), 4 (19), 3333.

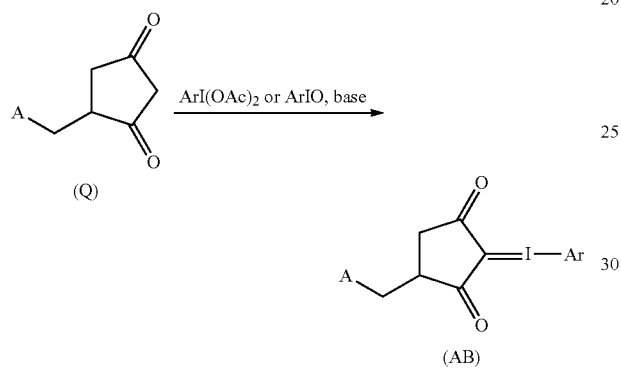

Additional compounds of formula (A) may be prepared by the pinacol rearrangement of compounds of formula (AC) or compounds of formula (AD) wherein R'''' is $C_1$-$C_4$alkyl (preferably methyl) under acidic conditions (see, for example, Eberhardt, U. et. al. Chem. Ber. (1983), 116(1), 119-35 and Wheeler, T. N. U.S. Pat. No. 4,283,348)

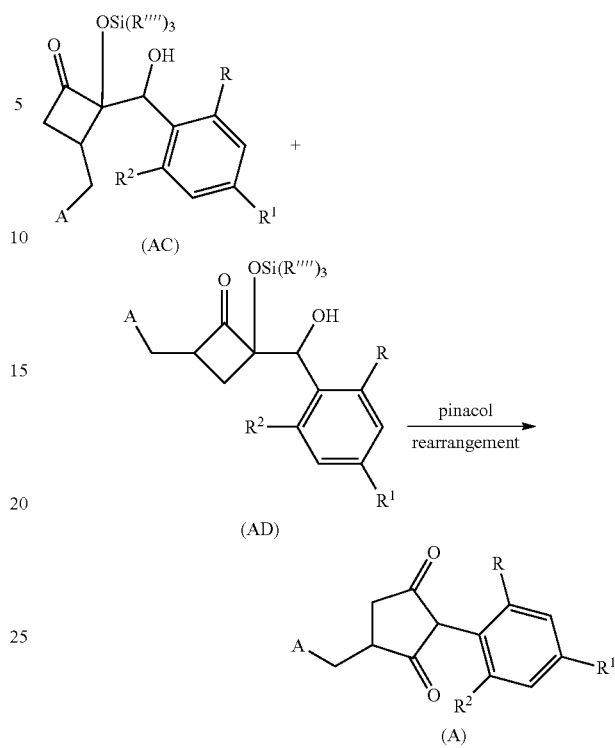

Compounds of formula (AC) and compounds of formula (AD) may be prepared by treating compounds of formula (AE) with compounds of formula (AF) in the presence of an acid (such as titanium tetrachloride or magnesium iodide) optionally in a suitable solvent (such as dichloromethane) at a temperature between −80° C. and 30° C. (see, for example, Li, W.-D. Z. and Zhang, X.-X. Org. Lett. (2002), 4(20), 3485-3488; Shimada, J. et al., J. Am. Chem. Soc. (1984), 106(6), 1759-73; Eberhardt, U. et. al. Chem. Ber. (1983), 116(1), 119-35 and Wheeler, T. N. U.S. Pat. No. 4,283,348).

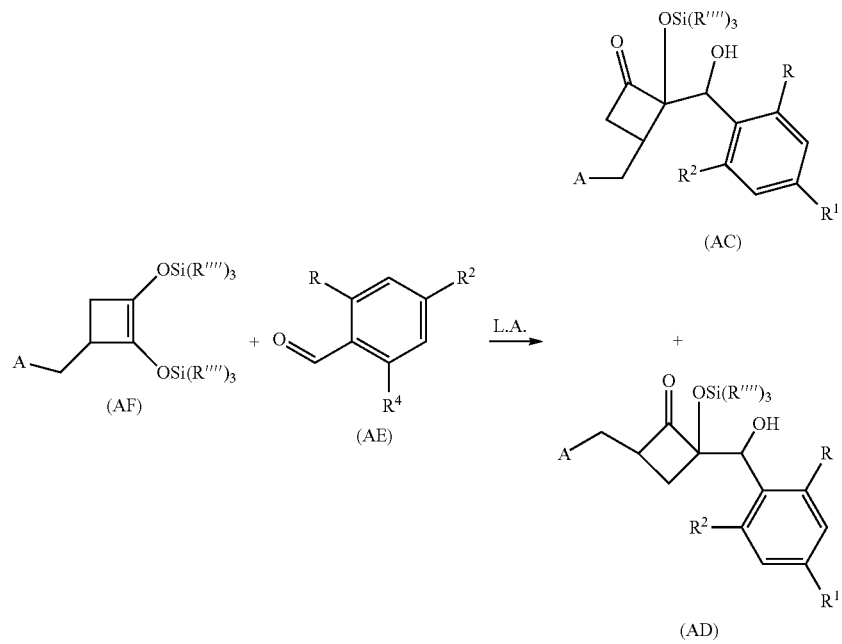

Compounds of formula (AE) are known or may be made by known methods from compounds of formula (W) or compounds of formula (AA).

Compounds of formula (AF) may be prepared from compounds of formula (AG) where in R' is an alkyl group (preferably methyl) in the presence of chloro tri-$C_1$-$C_4$alkyl silyl and a metal (preferably sodium) in a suitable solvent (such as toluene or diethyl ether) at a temperature between 20° C. and 150° C. (see, for example, Blanchard, A. N. and Burnell, D. J. Tetrahedron Lett. (2001), 42(29), 4779-4781 and Salaun, J. et al. Tetrahedron (1989), 45(10), 3151-62).

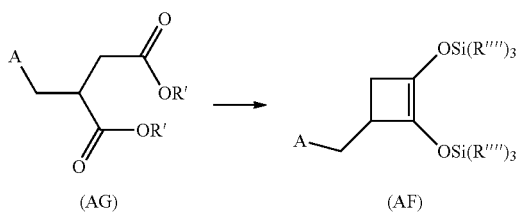

Compounds of formula (AG) are analogous to compounds of formula (H) and compounds of formula (G) and may be prepared by knows methods analogous to those describe for compounds of formula (H) and compounds of formula (G). Compounds of formula (AG) are also known in the literature, see for example, Arnold, R. T. and Showell, J. S. J. Am. Chem. Soc. 1957, 79 (2), 419-422.

The compounds of formula I according to the invention can be used as crop protection agents in unmodified form, as obtained in the synthesis, but they are generally formulated into crop protection compositions in a variety of ways using formulation adjuvants, such as carriers, solvents and surface-active substances.

Hence, the invention also provides a herbicidal composition, which comprises a herbicidally effective amount of a compound of formula I as defined herein.

The formulations (compositions) can be in various physical forms, for example in the form of dusting powders, gels, wettable powders, coated or impregnated granules for manual or mechanical distribution on target sites, water-dispersible granules, water-soluble granules, emulsifiable granules, water-dispersible tablets, effervescent compressed tablets, water-soluble tapes, emulsifiable concentrates, microemulsifiable concentrates, oil-in-water (EW) or water-in-oil (WO) emulsions, other multiphase systems such as oil/water/oil and water/oil/water products, oil flowables, aqueous dispersions, oily dispersions, suspoemulsions, capsule suspensions, soluble liquids, water-soluble concentrates (with water or a water-miscible organic solvent as carrier), impregnated polymer films or in other forms known, for example, from the Manual on Development and Use of FAO Specifications for Plant Protection Products, 5th Edition, 1999. The active ingredient may be incorporated into microfibers or microrods formed of polymers or polymerizable monomers and having diameter of about 0.1 to about 50 microns and aspect ratio of between about 10 and about 1000.

Such formulations can either be used directly or are diluted prior to use. They can then be applied through suitable ground or aerial application spray equipment or other ground application equipment such as central pivot irrigation systems or drip/trickle irrigation means.

Diluted formulations can be prepared, for example, with water, liquid fertilisers, micronutrients, biological organisms, oil or solvents.

The formulations can be prepared, for example, by mixing the active ingredient with formulation adjuvants in order to obtain compositions in the form of finely divided solids, granules, solutions, dispersions or emulsions. The active ingredients can also be contained in fine microcapsules consisting of a core and a polymeric shell. Microcapsules usually have a diameter of from 0.1 to 500 microns. They contain active ingredients in an amount of about from 25 to 95% by weight of the capsule weight. The active ingredients can be present in the form of liquid technical material, in the form of a suitable solution, in the form of fine particles in solid or liquid dispersion or as a monolithic solid. The encapsulating membranes comprise, for example, natural and synthetic gums, cellulose, styrene-butadiene copolymers or other similar suitable membrane forming material, polyacrylonitrile, polyacrylate, polyester, polyamides, polyureas, polyurethane, aminoplast resins or chemically modified starch or other polymers that are known to the person skilled in the art in this connection.

Alternatively it is possible for fine so called "microcapsules" to be formed wherein the active ingredient is present in the form of finely divided particles in a solid matrix of a base substance, but in that case the microcapsule is not encapsulated with a diffusion limiting membrane as outlined in the preceding paragraph.

The active ingredients may be adsorbed on a porous carrier. This may enable the active ingredients to be released into their surroundings in controlled amounts (e.g. slow release). Other forms of controlled release formulations are granules or powders in which the active ingredient is dispersed or dissolved in a solid matrix consisting of a polymer, a wax or a suitable solid substance of lower molecular weight. Suitable polymers are polyvinyl acetates, polystyrenes, polyolefins, polyvinyl alcohols, polyvinyl pyrrolidones, alkylated polyvinyl pyrrolidones, copolymers of polyvinyl pyrrolidones and maleic anhydride and esters and half-esters thereof, or chemically modified cellulose esters like carboxymethyl cellulose, methyl cellulose, or hydroxyethyl cellulose. Examples of suitable waxes are polyethylene wax, oxidized polyethylene wax, ester waxes like montan waxes, waxes of natural origin like carnauba wax, candelilla wax, or beeswax, etc. Other suitable matrix materials for slow release formulations are starch, stearin, or lignin.

The formulation adjuvants suitable for the preparation of the compositions according to the invention are generally known per se.

As liquid carriers there may be used: water, aromatic solvents such as toluene, m-xylene, o-xylene, p-xylene and mixtures thereof, cumene, aromatic hydrocarbon blends with boiling ranges between 140 and 320° C. known under various trademarks like Solvesso®, Shellsol A®, Caromax®, Hydrosol®, paraffinic and isoparaffinic carriers such as paraffin oils, mineral oils, de-aromatized hydrocarbon solvents with boiling ranges between 50 and 320° C. known for instance under the trademark Exxsol®, non-dearomatized hydrocarbon solvents with boiling ranges between 100 and 320° C. known under the tradename Varsol®, isoparaffinic solvents with boiling ranges between 100 and 320° C. known under tradenames like Isopar® or Shellsol T®, hydrocarbons such as cyclohexane, tetrahydronaphthalene (tetralin), decahydronaphthalene, alpha-pinene, d-limonene, hexadecane, isooctane, ester solvents such as ethyl acetate, n/i-butyl acetate, amyl acetate, i-bornyl acetate, 2-ethylhexyl acetate, $C_6$-$C_{18}$alkyl esters of acetic acid known under the tradename Exxate®, lactic acid ethylester, lactic acid propylester, lactic acid butylester, benzyl benzoate, benzyl lactate, dipropyleneglycol dibenzoate, dialkyl esters of succinic, maleic and fumaric acid and polar solvents like N-methylpyrrolidone, N-ethyl pyrrolidone, $C_3$-$C_{18}$-alkyl pyrrolidones, gamma-butyrolactone, dimethylsulfoxide, N,N-dimethylformamide, N,N-dimethylacetamide, N,N-dimethyllactamide, $C_4$-$C_{18}$ fatty acid dimethylamides, benzoic acid dimethylamide, acetonitrile, acetone, methyl ethyl ketone, methyl-isobutyl ketone, isoamyl ketone, 2-heptanone, cyclohexanone, isophorone, methyl isobutenyl ketone (mesityl oxide), acetophenone, ethylene carbonate, propylene carbonate, butylene carbonate, alcoholic solvents and diluents such as methanol, ethanol, propanol, n/iso-butanol, n/iso-pentanol, 2-ethyl hexanol, n-octanol, tetrahydrofurfuryl alkohol, 2-methyl-2,4-pentanediol, 4-hydroxy-4-methyl-2-pentanon, cyclohexanol, benzyl alcohol, ethylene glycol, ethylene glycol butyl ether, ethylene glycol methyl ether, diethylene glycol, diethylene glycol butyl ether, diethylene glycol ethyl ether, diethylene glycol methyl ether, propylene glycol, dipropylene glycol, dipropylene glycol methyl ether and other similar glycol ether solvents based on ethylene glycol, propylene glycol and butylene glycol feedstocks, triethylene glycol, polyethylene glycol (PEG 400), polypropylenglycols with molecular masses of 400-4000, glycerol, glycerol acetate, glycerol diacetate, glycerol triacetate, 1,4-dioxane, diethylene glycol abietate, chlorobenzene, chlorotoluene, fatty acid esters such as methyl octanoate, isopropyl myristate, methyl laurate, methyl oleate, mixture of $C_8$-$C_{10}$ fatty acid methyl esters, rape seed oil methyl and ethyl esters, soy bean oil methyl and ethyl esters, vegetable oils, fatty acids such as oleic acid, linoleic acid, linolenic acid, esters of phosphoric and phosphonic acid such as triethyl phosphate, $C_3$-$C_{18}$-tris-alkyl phosphates, alkylaryl phosphates, bis-octyl-octyl phosphonates.

Water is generally the carrier of choice for the dilution of the concentrates.

Suitable solid carriers are, for example, talc, titanium dioxide, pyrophyllite clay, silica (fumed or precipated silica and optionally functionalised or treated, for instance silanised), attapulgite clay, kieselguhr, limestone, calcium carbonate, bentonite, calcium montomorillonite, cottonseed husks, wheatmeal, soybean flour, pumice, wood flour, ground walnut shells, lignin and similar materials, as described, for example, in the EPA CFR 180.1001. (c) & (d). Powdered or granulated fertilisers can also be used as solid carriers.

A large number of surface-active substances can advantageously be used both in solid and in liquid formulations, especially in those formulations which can be diluted with a carrier prior to use. Surface-active substances may be anionic, cationic, amphoteric, non-ionic or polymeric and they may be used as emulsifiying, wetting, dispersing or suspending agents or for other purposes. Typical surface-active substances include, for example, salts of alkyl sulfates, such as diethanolammonium lauryl sulphate; Sodium lauryl sulphate, salts of alkylarylsulfonates, such as calcium or sodium dodecylbenzenesulfonate; alkylphenol-alkylene oxide addition products, such as nonylphenol ethoxylates; alcohol-alkylene oxide addition products, such as tridecyl alcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryl trimethylammonium chloride, polyethylene glycol esters of fatty acids, such as polyethylene glycol stearate; block copolymers of ethylene oxide and propylene oxide; and salts of mono- and di-alkyl phosphate esters; and also further substances described e.g. in "McCutcheon's Detergents and Emulsifiers Annual", MC Publishing Corp., Ridgewood, N.J., 1981.

Further adjuvants which can usually be used in pesticidal formulations include crystallisation inhibitors, viscosity-modifying substances, suspending agents, dyes, anti-oxidants, foaming agents, light absorbers, mixing aids, anti-foams, complexing agents, neutralising or pH-modifying substances and buffers, corrosion-inhibitors, fragrances, wetting agents, absorption improvers, micronutrients, plasticisers, glidants, lubricants, dispersants, thickeners, anti-freezes, microbiocides, compatibility agents and solubilisers and also liquid and solid fertilisers.

The formulations may also comprise additional active substances, for example further herbicides, herbicide safeners, plant growth regulators, fungicides or insecticides.

Therefore, the invention also provides a herbicidal composition, which comprises a herbicidally effective amount of a compound of formula I as defined herein, and optionally (or preferably) a further herbicide as mixture partner for the compound of formula I, or optionally (or preferably) a safener, or both.

The invention also provides a herbicidal composition, which comprises a herbicidally effective amount of a compound of formula I as defined herein, a safener, and optionally (or preferably) a further herbicide as mixture partner for the compound of formula I, wherein the safener is benoxacor, cloquintocet-mexyl, cyprosulfamide, mefenpyr-diethyl or N-(2-methoxybenzoyl)-4-[(methylaminocarbonyl)amino]benzenesulfonamide.

The compositions according to the invention can additionally include an additive (commonly referred to as an adjuvant), comprising a mineral oil, an oil of vegetable or animal origin, alkyl esters of such oils or mixtures of such oils and oil derivatives. The amount of oil additive used in the composition according to the invention is generally from 0.01 to 10%, based on the spray mixture. For example, the oil additive can be added to the spray tank in the desired concentration after the spray mixture has been prepared. Preferred oil additives comprise mineral oils or an oil of vegetable origin, for example rapeseed oil, olive oil or sunflower oil, emulsifiable vegetable oil, such as AMIGO® (Loveland Products Inc.), alkyl esters of oils of vegetable origin, for example the methyl derivatives, or an oil of animal origin, such as fish oil or beef tallow. A preferred additive contains, for example, as active components essentially 80% by weight alkyl esters of fish oils and 15% by weight methylated rapeseed oil, and also 5% by weight of customary emulsifiers and pH modifiers. Especially preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid, being important. Those esters are known as methyl laurate (CAS-111-82-0), methyl palmitate (CAS-112-39-0) and methyl oleate (CAS-112-62-9). A preferred fatty acid methyl ester derivative is AGNIQUE ME 18 RD-F® (Cognis). Those and other oil derivatives are also known from the Compendium of Herbicide Adjuvants, 5th Edition, Southern Illinois University, 2000.

The application and action of the oil additives can be further improved by combining them with surface-active substances, such as non-ionic, anionic, cationic or amphoteric surfactants. Examples of suitable anionic, non-ionic, cationic or amphoteric surfactants are listed on pages 7 and 8 of WO97/34485. Preferred surface-active substances are anionic surfactants of the dodecylbenzylsulfonate type, especially the calcium salts thereof, and also non-ionic surfactants of the fatty alcohol ethoxylate type. Special preference is given to ethoxylated $C_{12}$-$C_{22}$ fatty alcohols having a degree of ethoxylation of from 5 to 40. Examples of commercially available surfactants are the Genapol types (Clariant). Also preferred are silicone surfactants, especially polyalkyl-oxide-modified heptamethyltrisiloxanes, which are commercially available e.g. as SILWET L-77®, and also perfluorinated surfactants. The concentration of surface-active substances in relation to the total additive is generally from 1 to 50% by weight. Examples of oil additives that consist of mixtures of oils or mineral oils or derivatives thereof with surfactants are TURBOCHARGE®, ADIGOR® (both (Syngenta Crop Protection AG), ACTIPRON® (BP Oil UK Limited), AGRI-DEX® (Helena Chemical Company).

The said surface-active substances may also be used in the formulations alone, that is to say without oil additives.

Furthermore, the addition of an organic solvent to the oil additive/surfactant mixture can contribute to a further enhancement of action. Suitable solvents are, for example, SOLVESSO® and AROMATIC® solvents (Exxon Corporation). The concentration of such solvents can be from 10 to 80% by weight of the total weight. Such oil additives, which may be in admixture with solvents, are described, for example, in U.S. Pat. No. 4,834,908. A commercially available oil additive disclosed therein is known by the name MERGE® (BASF). Further oil additives that are preferred according to the invention are SCORE® and ADIGOR® (both Syngenta Crop Protection AG).

In addition to the oil additives listed above, in order to enhance the activity of the compositions according to the invention it is also possible for formulations of alkylpyrrolidones, (e.g. AGRIMAX® from ISP) to be added to the spray mixture. Formulations of synthetic latices, such as, for example, polyacrylamide, polyvinyl compounds or poly-1-p-menthene (e.g. BOND®, COURIER® or EMERALD®) can also be used.

Such adjuvant oils as described in the preceding paragraphs may be employed as the carrier liquid in which an active compound is dissolved, emulsified or dispersed as appropriate to the physical form of the active compound.

The pesticidal (e.g. herbicidal) formulations generally contain from 0.1 to 99% by weight, especially from 0.1 to 95% by weight, of a compound of formula I, and preferably from 1 to 99.9% by weight of a formulation adjuvant, which preferably includes from 0 to 25% by weight of a surface-active substance. Whereas commercial products will preferably be formulated as concentrates, the end user will normally employ dilute formulations.

The rate of application of the compounds of formula I may vary within wide limits and depends upon the nature of the soil, the method of application (pre- or post-emergence; seed dressing; application to the seed furrow; no tillage application etc.), the crop plant, the weed or grass to be controlled, the prevailing climatic conditions, and other factors governed by the method of application, the time of application and the target crop. The compounds of formula I according to the invention are generally applied at a rate of 1 to 2000 g/ha, preferably 1 to 1000 g/ha, more preferably 1 to 500 g/ha, and most preferably at 10 to 250 g/ha (in particular at 10, 15, 16, 20, 30, 50, 60, 62.5, 100, 125 or 250 g/ha).

Preferred formulations have especially the following representative compositions:
(%=percent by weight):
Emulsifiable Concentrates:
active ingredient: 1 to 95%, preferably 60 to 90%
surface-active agents: 1 to 30%, preferably 5 to 20%
solvents as liquid carrier: 1 to 80%, preferably 1 to 35%
Dusts:
active ingredient: 0.1 to 10%, preferably 0.1 to 5%
solid carriers: 99.9 to 90%, preferably 99.9 to 99%
Suspension Concentrates:
active ingredient: 5 to 75%, preferably 10 to 50%
water: 94 to 24%, preferably 88 to 30%
surface-active agents: 1 to 40%, preferably 2 to 30%
Wettable Powders:
active ingredient: 0.5 to 90%, preferably 1 to 80%
surface-active agents: 0.5 to 20%, preferably 1 to 15%
solid carriers: 5 to 95%, preferably 15 to 90%
Granules:
active ingredient: 0.1 to 30%, preferably 0.1 to 15%
solid carriers: 99.5 to 70%, preferably 97 to 85%
Waterdispersible Granules:
active ingredient: 1 to 90%, preferably 10 to 80%
surface-active agents: 0.5 to 80%, preferably 5 to 30%
solid carriers: 90 to 10%, preferably 70 to 30%

The following Examples further illustrate, but do not limit, the invention.

| F1. Emulsifiable concentrates | | | | |
|---|---|---|---|---|
| | a) | b) | c) | d) |
| active ingredient | 5% | 10% | 25% | 50% |
| calcium dodecylbenzene-sulfonate | 6% | 8% | 6% | 8% |
| castor oil polyglycol ether (36 mol of ethylene oxide) | 4% | — | 4% | 4% |
| octylphenol polyglycol ether (7-8 mol of ethylene oxide) | — | 4% | — | 2% |
| NMP | — | 10% | — | 20% |
| arom. hydrocarbon mixture $C_9$-$C_{12}$ | 85% | 68% | 65% | 16% |

Emulsions of any desired concentration can be prepared from such concentrates by dilution with water.

| F2. Solutions | | | | |
|---|---|---|---|---|
| | a) | b) | c) | d) |
| active ingredient | 5% | 10% | 50% | 90% |
| 1-methoxy-3-(3-methoxy-propoxy)-propane | 40% | 50% | — | — |
| polyethylene glycol MW 400 | 20% | 10% | — | — |
| NMP | — | — | 50% | 10% |
| arom. hydrocarbon mixture $C_9$-$C_{12}$ | 35% | 30% | — | — |

The solutions are suitable for application undiluted or after dilution with water.

| F3. Wettable powders | | | | |
|---|---|---|---|---|
| | a) | b) | c) | d) |
| active ingredient | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7-8 mol of ethylene oxide) | — | 1% | 2% | — |
| highly dispersed silicic acid | 1% | 3% | 5% | 10% |
| kaolin | 88% | 62% | 35% | — |

The active ingredient is thoroughly mixed with the adjuvants and the mixture is thoroughly ground in a suitable mill, yielding wettable powders which can be diluted with water to give suspensions of any desired concentration.

| F4. Coated granules | | | |
| --- | --- | --- | --- |
|  | a) | b) | c) |
| active ingredient | 0.1% | 5% | 15% |
| highly dispersed silica | 0.9% | 2% | 2% |
| inorg. carrier (diameter 0.1-1 mm) e.g. CaCO$_3$ or SiO$_2$ | 99.0% | 93% | 83% |

The active ingredient is dissolved in methylene chloride, the solution is sprayed onto the carrier and the solvent is subsequently evaporated off in vacuo.

| F5. Coated granules | | | |
| --- | --- | --- | --- |
|  | a) | b) | c) |
| active ingredient | 0.1% | 5% | 15% |
| polyethylene glycol MW 200 | 1.0% | 2% | 3% |
| highly dispersed silica | 0.9% | 1% | 2% |
| inorg. carrier (diameter 0.1-1 mm) e.g. CaCO$_3$ or SiO$_2$ | 98.0% | 92% | 80% |

The finely ground active ingredient is applied uniformly, in a mixer, to the carrier moistened with polyethylene glycol. Non-dusty coated granules are obtained in this manner.

| F6. Extruded granules | | | | |
| --- | --- | --- | --- | --- |
|  | a) | b) | c) | d) |
| active ingredient | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants and the mixture is moistened with water. The resulting mixture is extruded and then dried in a stream of air.

| F7. Water-dispersible granules | | | | |
| --- | --- | --- | --- | --- |
|  | a) | b) | c) | d) |
| active ingredient | 5% | 10% | 40% | 90% |
| sodium lignosulfonate | 20% | 20% | 15% | 7% |
| dibutyl naphthalene sulfonate | 5% | 5% | 4% | 2% |
| Gum arabic | 2% | 1% | 1% | 1% |
| Diatomaceous earth | 20% | 30% | 5% |  |
| Sodium sulphate |  | 4% | 5% |  |
| kaolin | 48% | 30% | 30% |  |

The active ingredient is mixed and ground with the adjuvants and the mixture is moistened with water. The resulting mixture is extruded and then dried in a stream of air.

| F7. Dusts | | | |
| --- | --- | --- | --- |
|  | a) | b) | c) |
| active ingredient | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

| F8. Suspension concentrates | | | | |
| --- | --- | --- | --- | --- |
|  | a) | b) | c) | d) |
| active ingredient | 3% | 10% | 25% | 50% |
| propylene glycol | 5% | 5% | 5% | 5% |
| nonylphenol polyglycol ether (15 mol of ethylene oxide) | — | 1% | 2% | — |
| sodium lignosulfonate | 3% | 3% | 7% | 6% |
| heteropolysacharide (Xanthan) | 0.2% | 0.2% | 0.2% | 0.2% |
| 1,2-Benzisothiazolin-3-on | 0.1% | 0.1% | 0.1% | 0.1% |
| silicone oil emulsion | 0.7% | 0.7% | 0.7% | 0.7% |
| water | 87% | 79% | 62% | 38% |

The finely ground active ingredient is intimately mixed with the adjuvants, yielding a suspension concentrate from which suspensions of any desired concentration can be prepared by dilution with water.

Preferably, the term "active ingredient" as used in the examples mentioned above refers to one of the compounds selected from Tables 1 to 21 shown below. It can also refer to mixtures of the compound of formula I, in particular a compound selected from said Tables 1 to 21, with other herbicides or safeners, which mixtures are specifically disclosed below.

The invention also provides a method of controlling grasses and weeds in crops of useful plants, which comprises applying a herbicidally effective amount of a compound of formula I as defined herein, or of a composition comprising such a compound, to the plants or to the locus thereof.

Crops of useful plants, in which the compositions and/or the methods of controlling grasses and weeds according to the invention can be used, are typically cereals (in particular wheat, barley, rye or triticale; preferably wheat or barley), rice, corn (i.e. maize), rape, sugarbeet, sugarcane, soybean, cotton, sunflower, peanut, or plantation crops. Alternatively, the crops of useful plants can be oats (e.g. *Avena sativa*, the common oat). The crops of useful plants are preferably cereals (e.g. wheat, barley, rye or triticale), corn or soybean; or more preferably are wheat, barley, corn or soybean; or most preferably are wheat or barley.

The term "crops" is to be understood as also including crops that have been rendered tolerant to herbicides or classes of herbicides (for example ALS, GS, EPSPS, PPO and HPPD inhibitors) as a result of conventional methods of breeding or genetic engineering. An example of a crop that has been rendered tolerant e.g. to imidazolinones, such as imazamox, by conventional methods of breeding is Clearfield® summer rape (Canola). Examples of crops that have been rendered tolerant to herbicides by genetic engineering methods include e.g. glyphosate- and glufosinate-resistant maize varieties commercially available under the trade names RoundupReady® and LibertyLink®.

The weeds to be controlled may be monocotyledonous and/or dicotyledonous weeds, such as, for example, *Stellaria, Nasturtium, Agrostis, Digitaria* (e.g. *Digitaria sanguinalis* (DIGSA)), *Avena* (e.g. *Avena* species other than *Avena sativa* (the common oat); preferably *Avena fatua* (AVEFA), also known as the common wild oat), *Setaria* (e.g. *Setaria faberi* (SETFA)), *Sinapis, Lolium* (e.g. *Lolium perenne* (LOLPE)), *Solanum, Echinochloa* (e.g. *Echinochloa crus-galli* (ECHCG)), *Scirpus, Monochoria, Sagittaria, Bromus, Alopecurus* (e.g. *Alopecurus myosuroides* (ALOMY)), *Sorghum, Rottboellia, Cyperus, Abutilon, Sida, Xanthium, Amaranthus, Chenopodium, Ipomoea, Chrysanthemum, Galium, Viola* and/or *Veronica*. The weeds to be controlled may alternatively be *Phalaris, Apera, Leptochloa, Geranium, Beta, Brassica, Kochia, Poa, Sinapis, Polygonum, Brachiaria, Eriochloa, Bidens, Euphorbia*, and/or *Panicum*.

Control of monocotyledonous weeds (e.g. weedy grasses) is preferred; in particular *Agrostis, Avena* (e.g. *Avena* species other than *Avena sativa* (the common oat); preferably *Avena fatua* (AVEFA), also known as the common wild oat), *Setaria* (e.g. *Setaria faberi* (SETFA)), *Lolium* (e.g. *Lolium perenne* (LOLPE)), *Echinochloa* (e.g. *Echinochloa crus-galli* (ECHCG)), *Bromus, Alopecurus* (e.g. *Alopecurus myosuroides* (ALOMY)), and/or *Sorghum*. Alternatively, the monocotyledonous weeds to be controlled are, in particular, *Phalaris, Apera, Panicum, Digitaria, Brachiaria, Poa, Eriochloa, Rottboellia*, and/or *Leptochloa*; and/or can be volunteer (non-crop) cereals and/or volunteer (non-crop) maize. The monocotyledonous weeds, to be controlled by compound of formula I, can be either sensitive to or partially or wholly resistant to one or more herbicides, not being a compound of formula I, which are already approved and commercially-available for herbicidal use (and/or which are already used in agriculture as herbicides).

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt-176 maize hybrids of NK® (Syngenta Seeds). The Bt toxin is a protein that is formed naturally by *Bacillus thuringiensis* soil bacteria. Examples of toxins and transgenic plants able to synthesise such toxins are described in EP-A-451 878, EP-A-374 753, WO 93/07278, WO 95/34656, WO 03/052073 and EP-A-427 529. Examples of transgenic plants that contain one or more genes which code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops and their seed material can be resistant to herbicides and at the same time also to insect feeding ("stacked" transgenic events). Seed can, for example, have the ability to express an insecticidally active Cry3 protein and at the same time be glyphosate-tolerant. The term "crops" is to be understood as also including crops obtained as a result of conventional methods of breeding or genetic engineering which contain so-called output traits (e.g. improved flavour, storage stability, nutritional content).

Areas under cultivation are to be understood as including land where the crop plants are already growing as well as land intended for the cultivation of those crop plants.

The compounds of formula I according to the invention can also be used in combination with further herbicides. Preferably, in these mixtures, the compound of the formula I is one of those compounds listed in Tables 1 to 21 and/or in Tables A1, B1 and/or C1 hereinbelow. The following mixtures of the compound of formula I may be important:

compound of formula I+acetochlor, compound of formula I+acifluorfen, compound of formula I+acifluorfen-sodium, compound of formula I+aclonifen, compound of formula I+acrolein, compound of formula I+alachlor, compound of formula I+alloxydim, compound of formula I+allyl alcohol, compound of formula I+ametryn, compound of formula I+amicarbazone, compound of formula I+amidosulfuron, compound of formula I+aminopyralid, compound of formula I+amitrole, compound of formula I+ammonium sulfamate, compound of formula I+anilofos, compound of formula I+asulam, compound of formula I+atraton, compound of formula I+atrazine, compound of formula I+azimsulfuron, compound of formula I+BCPC, compound of formula I+beflubutamid, compound of formula I+benazolin, compound of formula I+benfluralin, compound of formula I+benfuresate, compound of formula I+bensulfuron, compound of formula I+bensulfuron-methyl, compound of formula I+bensulide, compound of formula I+bentazone, compound of formula I+benzfendizone, compound of formula I+benzobicyclon, compound of formula I+benzofenap, compound of formula I+bifenox, compound of formula I+bilanafos, compound of formula I+bispyribac, compound of formula I+bispyribac-sodium, compound of formula I+borax, compound of formula I+bromacil, compound of formula I+bromobutide, compound of formula I+bromoxynil, compound of formula I+butachlor, compound of formula I+butafenacil, compound of formula I+butamifos, compound of formula I+butralin, compound of formula I+butroxydim, compound of formula I+butylate, compound of formula I+cacodylic acid, compound of formula I+calcium chlorate, compound of formula I+cafenstrole, compound of formula I+carbetamide, compound of formula I+carfentrazone, compound of formula I+carfentrazone-ethyl, compound of formula I+CDEA, compound of formula I+CEPC, compound of formula I+chlorflurenol, compound of formula I+chlorflurenol-methyl, compound of formula I+chloridazon, compound of formula I+chlorimuron, compound of formula I+chlorimuron-ethyl, compound of formula I+chloroacetic acid, compound of formula I+chlorotoluron, compound of formula I+chlorpropham, compound of formula I+chlorsulfuron, compound of formula I+chlorthal, compound of formula I+chlorthal-dimethyl, compound of formula I+cinidon-ethyl, compound of formula I+cinmethylin, compound of formula I+cinosulfuron, compound of formula I+cisanilide, compound of formula I+clethodim, compound of formula I+clodinafop, compound of formula I+clodinafop-propargyl, compound of formula I+clomazone, compound of formula I+clomeprop, compound of formula I+clopyralid, compound of formula I+cloransulam, compound of formula I+cloransulam-methyl, compound of formula I+CMA, compound of formula I+4-CPB, compound of formula I+CPMF, compound of formula I+4-CPP, compound of formula I+CPPC, compound of formula I+cresol, compound of formula I+cumyluron, compound of formula I+cyanamide, compound of formula I+cyanazine, compound of formula I+cycloate, compound of formula I+cyclosulfamuron, compound of formula I+cycloxydim, compound of formula I+cyhalofop, compound of formula I+cyhalofop-butyl, compound of formula I+2,4-D, compound of formula I+3,4-DA, compound of formula I+daimuron, compound of formula I+dalapon, compound of formula I+dazomet, compound of formula I+2,4-DB, compound of formula I+3,4-DB, compound of formula I+2,4-DEB, compound of formula I+desmedipham, compound of formula I+dicamba, compound of formula I+dichlobenil, compound of formula I+ortho-dichlorobenzene, compound of formula I+para-dichlorobenzene, compound of formula I+dichlorprop, compound of formula I+dichlorprop-P, compound of formula I+diclofop, compound of formula I+diclofop-methyl, compound of formula I+diclosulam, compound of formula I+difenzoquat, compound of formula I+difenzoquat metilsulfate, compound of formula I+diflufenican, compound of formula I+diflufenzopyr, compound of formula I+dimefuron, compound of formula I+dimepiperate, compound of formula I+dimethachlor, compound of formula I+dimethametryn, compound of formula I+dimethenamid, compound of formula I+dimethenamid-P, compound of formula I+dimethipin, compound of formula I+dimethylarsinic acid, compound of formula I+dinitramine, compound of formula I+dinoterb, compound of formula I+diphenamid, compound of formula I+diquat, compound of formula I+diquat dibromide, compound of formula I+dithiopyr, compound of formula I+diuron, compound of formula I+DNOC, compound of formula I+3,4-DP, compound of formula I+DSMA, compound of formula I+EBEP, compound of formula I+endothal, compound of formula I+EPTC, compound of formula I+esprocarb, compound of formula I+ethalfluralin, compound of formula I+ethametsulfuron, compound of formula I+ethametsulfuronmethyl, compound of formula I+ethofumesate, compound of formula I+ethoxyfen, compound of formula I+ethoxysulfuron, compound of formula I+etobenzanid, compound of formula I+fenoxaprop-P, compound of formula I+fenoxaprop-P-ethyl, compound of formula I+fentrazamide, compound of formula I+ferrous sulfate, compound of formula I+flamprop-M, compound of formula I+flazasulfuron, compound of formula I+florasulam, compound of formula I+fluazifop, compound of formula I+fluazifop-butyl, compound of formula I+fluazifop-P, compound of formula I+fluazifop-P-butyl, compound of formula I+flucarbazone, compound of formula I+flucarbazone-sodium, compound of formula I+flucetosulfuron, compound of formula I+fluchloralin, compound of formula I+flufenacet, compound of formula I+flufenpyr, compound of formula I+flufenpyr-ethyl, compound of formula I+flumetsulam, compound of formula I+flumiclorac, compound of formula I+flumiclorac-pentyl, compound of formula I+flumioxazin, compound of formula I+fluometuron, compound of formula I+fluoroglycofen, compound of formula I+fluoroglycofen-ethyl, compound of formula I+flupropanate, compound of formula I+flupyrsulfuron, compound of formula I+flupyrsulfuron-methyl-sodium, compound of formula I+flurenol, compound of formula I+fluridone, compound of formula I+fluorochloridone, compound of formula I+fluoroxypyr, compound of formula I+flurtamone, compound of formula I+fluthiacet, compound of formula I+fluthiacet-methyl, compound of formula I+fomesafen, compound of formula I+foramsulfuron, compound of formula I+fosamine, compound of formula I+glufosinate, compound of formula I+glufosinate-ammonium, compound of formula I+glyphosate, compound of formula I+halosulfuron, compound of formula I+halosulfuron-methyl, compound of formula I+haloxyfop, compound of formula I+haloxyfop-P, compound of formula I+HC-252, compound of formula I+hexazinone, compound of formula I+imazamethabenz, compound of formula I+imazamethabenz-methyl, compound of formula I+imazamox, compound of formula I+imazapic, compound of formula I+imazapyr, compound of formula I+imazaquin, compound of formula I+imazethapyr, compound of formula I+imazosulfuron, compound of formula I+indanofan, compound of formula I+iodomethane, compound of formula I+iodosulfuron, compound of formula I+iodosulfuron-methyl-sodium, compound of formula I+ioxynil, compound of formula I+isoproturon, compound of formula I+isouron, compound of formula I+isoxaben, compound of formula I+isoxachlortole, compound of formula I+isoxaflutole, compound of formula I+karbutilate, compound of formula I+lactofen, compound of formula I+lenacil, compound of formula I+linuron, compound of formula I+MAA, compound of formula I+MAMA, compound of formula I+MCPA, compound of formula I+MCPA-thioethyl, compound of formula I+MCPB, compound of formula I+mecoprop, compound of formula I+mecoprop-P, compound of formula I+mefenacet, compound of formula I+mefluidide, compound of formula I+mesosulfuron, compound of formula I+mesosulfuron-methyl, compound of formula I+mesotrione, compound of formula I+metam, compound of formula I+metamifop, compound of formula I+metamitron, compound of formula I+metazachlor, compound of formula I+methabenzthiazuron, compound of formula I+methylarsonic acid, compound of formula I+methyldymron, compound of formula I+methyl isothiocyanate, compound of formula I+metobenzuron, compound of formula I+metolachlor, compound of formula I+S-metolachlor, compound of formula I+metosulam, compound of formula I+metoxuron, compound of formula I+metribuzin, compound of formula I+metsulfuron, compound of formula I+metsulfuron-methyl, compound of formula I+MK-616, compound of formula I+molinate, compound of formula I+monolinuron, compound of formula I+MSMA, compound of formula I+naproanilide, compound of formula I+napropamide, compound of formula I+naptalam, compound of formula I+neburon, compound of formula I+nicosulfuron, compound of formula I+nonanoic acid, compound of formula I+norflurazon, compound of formula I+oleic acid (fatty acids), compound of formula I+orbencarb, compound of formula I+orthosulfamuron, compound of formula I+oryzalin, compound of formula I+oxadiargyl, compound of formula I+oxadiazon, compound of formula I+oxasulfuron, compound of formula I+oxaziclomefone, compound of formula I+oxyfluorfen, compound of formula I+paraquat, compound of formula I+paraquat dichloride, compound of formula I+pebulate, compound of formula I+pendimethalin, compound of formula I+penoxsulam, compound of formula I+pentachlorophenol, compound of formula I+pentanochlor, compound of formula I+pentoxazone, compound of formula I+pethoxamid, compound of formula I+petrolium oils, compound of formula I+phenmedipham, compound of formula I+phenmedipham-ethyl, compound of formula I+picloram, compound of formula I+picolinafen, compound of formula I+pinoxaden, compound of formula I+piperophos, compound of formula I+potassium arsenite, compound of formula I+potassium azide, compound of formula I+pretilachlor, compound of formula I+primisulfuron, compound of formula I+primisulfuron-methyl, compound of formula I+prodiamine, compound of formula I+profluazol, compound of formula I+profoxydim, compound of formula I+prometon, compound of formula I+prometryn, compound of formula I+propachlor, compound of formula I+propanil, compound of formula I+propaquizafop, compound of formula I+propazine, compound of formula I+propham, compound of formula I+propisochlor, compound of formula I+propoxycarbazone, compound of formula I+propoxycarbazone-sodium, compound of formula I+propyzamide, compound of formula I+prosulfocarb, compound of formula I+prosulfuron, compound of formula I+pyraclonil, compound of formula I+pyraflufen, compound of formula I+pyraflufen-ethyl, compound of formula I+pyrazolynate, compound of formula I+pyrazosulfuron, compound of formula I+pyrazosulfuron-ethyl, compound of formula I+pyrazoxyfen, compound of formula I+pyribenzoxim, compound of formula I+pyributicarb, compound of formula I+pyridafol, compound of formula I+pyridate, compound of formula I+pyriftalid, compound of formula I+pyriminobac, compound of formula I+pyriminobac-methyl, compound of formula I+pyrimisulfan, compound of formula I+pyrithiobac, compound of formula I+pyrithiobac-sodium, compound of formula I+quinclorac, compound of formula I+quinmerac, compound of formula I+quinoclamine, compound of formula I+quizalofop, compound of formula I+quizalofop-P, compound of formula I+rimsulfuron, compound of formula I+sethoxydim, compound of formula I+siduron, compound of formula I+simazine, compound of formula I+simetryn, compound of formula I+SMA, compound of formula I+sodium arsenite, compound of formula I+sodium azide, compound of formula I+sodium chlorate, compound of formula I+sulcotrione, compound of formula I+sulfentrazone, compound of formula I+sulfometuron, compound of formula I+sulfometuron-methyl, compound of formula I+sulfosate, compound of formula I+sulfosulfuron, compound of formula I+sulfuric acid, compound of formula I+tar oils, compound of formula I+2,3,6-TBA, compound of formula I+TCA, compound of formula I+TCA-sodium, compound of formula I+tebuthiuron, compound of formula I+tepraloxydim, compound of formula I+terbacil, compound of formula I+terbumeton, compound of formula I+terbuthylazine, compound of formula I+terbutryn, compound of formula I+thenylchlor, compound of formula I+thiazopyr, compound of formula I+thifensulfuron, compound of formula I+thifensulfuron-methyl, compound of formula I+thiobencarb, compound of formula I+tiocarbazil, compound of formula I+topramezone, compound of formula I+tralkoxydim, compound of formula I+tri-allate, compound of formula I+triasulfuron, compound of formula I+triaziflam, compound of formula I+tribenuron, compound of formula I+tribenuron-methyl, compound of formula I+tricamba, compound of formula I+triclopyr, compound of formula I+trietazine, compound of formula I+trifloxysulfuron, compound of formula I+trifloxysulfuron-sodium, compound of formula I+trifluralin, compound of formula I+triflusulfuron, compound of formula I+triflusulfuron-methyl, compound of formula I+trihydroxytriazine, compound of formula I+tritosulfuron, compound of formula I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6), compound of formula I+4-[(4,5-dihydro-3-methoxy-4-methyl-5-oxo)-1H-1,2,4-triazol-1-ylcarbonylsulfamoyl]-5-methylthiophene-3-carboxylic acid (BAY636), compound of formula I+BAY747 (CAS RN 335104-84-2), compound of formula I+topramezone (CAS RN 210631-68-8), compound of formula I+4-hydroxy-3-[[2-[(2-methoxyethoxy)methyl]-6-(trifluoromethyl)-3-pyridinyl]carbonyl]-bicyclo[3.2.1]oct-3-en-2-one (CAS RN 352010-68-5), and compound of formula I+4-hydroxy-3-[[2-(3-methoxypropyl)-6-(difluoromethyl)-3-pyridinyl]carbonyl]-bicyclo[3.2.1]oct-3-en-2-one.

The following alternative mixtures of the compound of formula I may be important (preferably, in these mixtures, the compound of the formula I is one of those compounds listed in Tables 1 to 21 and/or in Tables A1, B1 and/or C1 hereinbelow):

compound of formula I+one of the herbicidal compounds disclosed in WO2010/059676 (Dow, e.g. for use with cereal crops, e.g. can be plus cloquintocet-mexyl), compound of formula I+one of the herbicidal compounds disclosed in WO2010/059680 (Dow, e.g. for use with cereal crops, e.g. can be plus a safener other than cloquintocet-mexyl), and compound of formula I+one of the herbicidal compounds disclosed in WO2010/059671 (Dow, e.g. for use with rice crops, e.g. can be plus a safener).

The mixing partners for the compound of formula I may also be in the form of esters or salts, as mentioned e.g. in The Pesticide Manual, 12th Edition (BCPC) 2000.

The compounds of formula I according to the invention can also be used in combination with safeners. Preferably, in these mixtures, the compound of the formula I is one of those compounds listed in Tables 1 to 21 below. The following mixtures with safeners, especially, come into consideration: compound of formula I+cloquintocet-mexyl, compound of formula I+cloquintocet acid and salts thereof, compound of formula I+fenchlorazole-ethyl, compound of formula I+fenchlorazole acid and salts thereof, compound of formula I+mefenpyr-diethyl, compound of formula I+mefenpyr diacid, compound of formula I+isoxadifen-ethyl, compound of formula I+isoxadifen acid, compound of formula I+furilazole, compound of formula I+furilazole R isomer, compound of formula (I)+N-(2-methoxybenzoyl)-4-[(methylaminocarbonyl)amino]benzenesulfonamide, compound of formula I+benoxacor, compound of formula I+dichlormid, compound of formula I+AD-67, compound of formula I+oxabetrinil, compound of formula I+cyometrinil, compound of formula I+cyometrinil Z-isomer, compound of formula I+fenclorim, compound of formula I+cyprosulfamide, compound of formula I+naphthalic anhydride, compound of formula I+flurazole, compound of formula I+CL 304,415, compound of formula I+dicyclonon, compound of formula I+fluxofenim, compound of formula I+DKA-24, compound of formula I+R-29148 and compound of formula I+PPG-1292. A safening effect can also be observed for the mixtures compound of the formula I+dymron, compound of the formula I+MCPA, compound of the formula I+mecopropand compound of the formula I+mecoprop-P.

The above-mentioned safeners and herbicides are described, for example, in the Pesticide Manual, Twelfth Edition, British Crop Protection Council, 2000. R-29148 is described, for example by P. B. Goldsbrough et al., Plant Physiology, (2002), Vol. 130 pp. 1497-1505 and references therein, PPG-1292 is known from WO09211761 and N-(2-methoxybenzoyl)-4-[(methylaminocarbonyl)amino]benzenesulfonamide is known from EP365484.

Benoxacor, cloquintocet-mexyl, cyprosulfamide, mefenpyr-diethyl and N-(2-methoxybenzoyl)-4-[(methylaminocarbonyl)amino]benzenesulfonamide are especially preferred safeners.

Cloquintocet-mexyl is the most preferred safener. Cloquintocet-mexyl is particularly valuable for use in combination with (e.g. in a mixture with) a compound of formula I according to the invention.

Therefore, the invention also provides a herbicidal composition, which comprises a herbicidally effective amount of a compound of formula I as defined herein, and optionally (or preferably) a further herbicide as mixture partner for the compound of formula I, or optionally (or preferably) a safener, or both.

The invention also provides a herbicidal composition, which comprises a herbicidally effective amount of a compound of formula I as defined herein, a safener, and optionally (or preferably) a further herbicide as mixture partner for the compound of formula I, wherein the safener is benoxacor, cloquintocet-mexyl, cyprosulfamide, mefenpyr-diethyl or N-(2-methoxybenzoyl)-4-[(methylaminocarbonyl)amino]benzenesulfonamide.

The rate of application of safener, relative to the herbicide (e.g. the compound of formula I), is largely dependent upon the mode of application. In the case of field treatment:

a) generally from 0.001 to 5.0 kg of safener/ha, preferably from 0.001 to 0.5 kg of safener/ha, more preferably 2 to 100 g of safener/ha (in particular at 2.5, 5, 7.5, 10, 20 or 50 g of safener/ha); and b) generally from 0.001 to 2 kg of herbicide/ha, but preferably from 0.005 to 1 kg of herbicide/ha, more preferably 5 to 500 g of herbicide/ha, and most preferably at 10 to 250 g of herbicide/ha (in particular at 10, 15, 16, 20, 30, 50, 60, 62.5, 100, 125 or 250 g of herbicide/ha);

are applied.

The safener and the herbicide (e.g. the compound of formula I) can for example be used (e.g. when together in a mixture formulation) at a herbicide:safener ratio of from 16:1 to 1:1, such as 8:1, 4:1 or 2:1, measured on the basis of the rates of application of herbicide and safener in g/ha; in particular where the safener is cloquintocet-mexyl.

The herbicidal compositions according to the invention are suitable for all methods of application customary in agriculture, such as, for example, pre-emergence application, post-emergence application and seed dressing. Depending upon the intended use, the safeners can be used for pretreating the seed material of the crop plant (dressing the seed or seedlings) or introduced into the soil before or after sowing, followed by the application of the (unsafened) compound of the formula (I), optionally in combination with a co-herbicide. It can, however, also be applied alone or together with the herbicide before or after emergence of the plants. The treatment of the plants or the seed material with the safener can therefore take place in principle independently of the time of application of the herbicide. The treatment of the plant by simultaneous application of herbicide and safener (e.g. in the form of a tank mixture) is generally preferred. The rate of application of safener relative to herbicide is largely dependent upon the mode of application. In the case of field treatment, generally from 0.001 to 5.0 kg of safener/ha, preferably from 0.001 to 0.5 kg of safener/ha, are applied. In the case of seed dressing, generally from 0.001 to 10 g of safener/kg of seed, preferably from 0.05 to 2 g of safener/kg of seed, are applied. When the safener is applied in liquid form, with seed soaking, shortly before sowing, it is advantageous to use safener solutions which contain the active ingredient in a concentration of from 1 to 10 000 ppm, preferably from 100 to 1000 ppm.

It is preferred to apply the mixture partner of the compound of formula I together with one of the safeners mentioned above.

The following examples illustrate the invention further but do not limit the invention.

PREPARATION EXAMPLES

Those skilled in the art will appreciate that certain compounds described below are alpha-ketoenols, and as such may exist as a single tautomer or as a mixture of keto-enol and diketone tautomers, as described, for example by J. March, Advanced Organic Chemistry, third edition, John Wiley and Sons. The compounds are shown in Table T1 as a single enol tautomer, but it should be inferred that this description covers both the diketone form and any possible enols which could arise through tautomerism. Furthermore, some of the compounds in Table A1 and Table B1 are drawn as single enantiomers for the purposes of simplicity, but unless specified as single enantiomers these structures should be construed as representing a mixture of enantiomers.

Within the detailed experimental section the diketone tautomer is chosen for naming purposes, even if the predominant tautomer is the enol form.

Example 1

Preparation of 2,2-dimethyl-propionic acid 4-(4-methoxyimino-cyclohexylmethyl)-3-oxo-2-(2,4,6-trimethyl-phenyl)-cyclopent-1-enyl ester

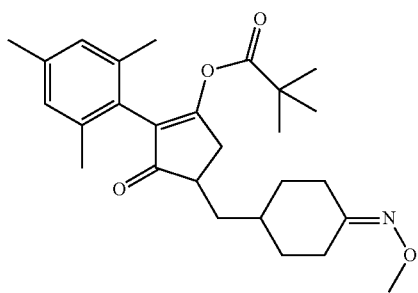 [SMILES: CON=C1CCC(CC2CC(OC(=O)C(C)(C)C)=C(c3c(C)cc(C)cc3C)C2=O)CC1]

Step 1

Preparation of 1,4-dioxa-spiro[4,5]decan-8-ol

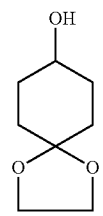

Into a 250 ml round bottom flask is weighed 20 g of 1,4-dioxa-spiro[4.5]decan-8-one (128 mmol) and dissolved in 200 ml of methanol to give a pale yellow solution. The solution is cooled to 5° C. and sodium borohydride (4 g, 106 mmol) is added portionwise keeping the temperature below 20° C. Once the addition is complete the solution was stirred at room temperature for 3 hours. The reaction is evaporated to one third volume and then diluted with water, acidified carefully with 0.5 M aqueous hydrochloric acid, and extracted with diethyl ether (2×100 ml). The combined organics extracts are dried over magnesium sulphate, filtered and evaporated to give 1,4-dioxa-spiro[4.5]decan-8-ol (12.2 g).

Step 2

Preparation of 8-benzyloxy-1,4-dioxa-spiro[4,5]decane

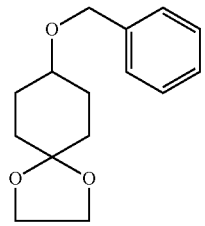 [SMILES: c1ccc(COC2CCC3(CC2)OCCO3)cc1]

1,4-dioxa-spiro[4.5]decan-8-ol (11.0 g, 70 mmol) in dry tetrahydrofuran (50 ml) is added dropwise to a stirred suspension of 60% sodium hydride disperse in mineral oil (2.80 g, 70 mmol) in dry tetrahydrofuran (50 ml). Once the addition is complete the reaction mixture is stirred for 2 hours at room temperature. A solution of benzyl bromide (13.2 g, 77 mmol) in dry tetrahydrofuran (50 ml) is added dropwise over a period of 20 minutes and stirred at room temp overnight. The reaction mixture is poured into water (200 ml), neutralised with 0.5 N aqueous hydrochloric acid and extracted with methylene chloride (2×100 ml). The combined organic layer was dried over magnesium sulphate, filtered and evaporated under reduced pressure. The residue is absorbed onto silica gel and purified on flash chromatography to give 8-benzyloxy-1,4-dioxa-spiro[4.5]decane (16 g).

Step 3

Preparation of 4-benzyloxy-cyclohexanone

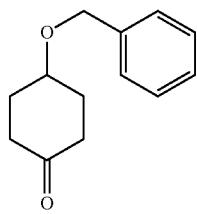 [SMILES: O=C1CCC(OCc2ccccc2)CC1]

8-Benzyloxy-1,4-dioxa-spiro[4.5]decane (15 g, 60 mmol) was dissolved in THF (150 ml) and 1M aqueous hydrochloric acid (40 ml) is added and the reaction mixture is heated to reflux overnight. The reaction mixture is cooled and diluted with water (200 ml) before being extracted with ethyl acetate (1×200 ml). The organic extract is washed with saturated solution of sodium bicarbonate and then dried over magnesium sulphate, filtered and evaporated under reduced pressure to give an oil. The oil is distilled under vacuum in a kugelrohr to give 4-benzyloxy-cyclohexanone (10 g).

Step 4

Preparation of 4-benzyloxy-cyclohexanecarbaldehyde

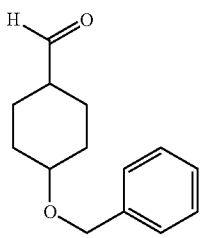 [SMILES: O=CC1CCC(OCc2ccccc2)CC1]

To a stirred suspension of methoxymethyl triphenylphosphonium chloride (13.8 g, 40 mmol) in dry THF (80 ml) is added dropwise a solution of lithium diisopropylamide (24.4 ml, 44 mmol, 1.8 M in hexane/THF/ethylbenzene), at 0-5° C. The resulting reaction mixture is stirred for 30 minutes and then cooled to −78° C. At this temperature, a solution of 4-benzyloxy-cyclohexanone (6.1 g, mmol) in tetrahydrofuran (30 ml) is added over a period of 30 minutes. Once the addition is completed the reaction mixture is stirred at −78° C. for 1 hour and then allowed to warm to room temperature and stirred overnight. The reaction mixture is then diluted to pH=2 with a 2N aqueous solution of hydrochloric acid and stirred for 3 hours at room temperature. The reaction was diluted with water and extracted with ethyl acetate (2×100 ml). The combined organic extracts are dried over magnesium sulphate, filtered and evaporated under reduced pressure. The residue is purified by flash chromatography to give 4-benzyloxy-cyclohexanecarbaldehyde (5.7 g).

Step 5

Preparation of 5-[(4-benzyloxy-cyclohexyl)-hydroxy-methyl]-3-methoxy-2-(2,46-trimethyl-phenyl)-cyclopent-2-enone

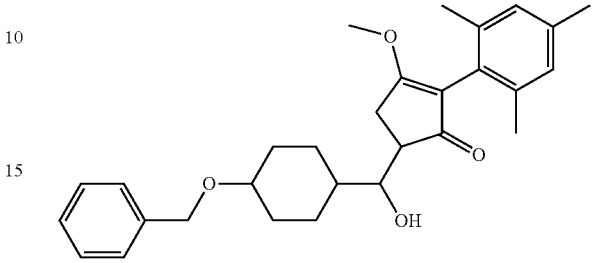

Into a 250 ml round bottom flask was weighed 3-methoxy-2-(2,4,6-trimethyl-phenyl)-cyclopent-2-enone (6 g, 26 mmol) and dissolved in dry tetrahydrofuran (30 ml).

The solution was cooled to −78° C. where upon a solution of lithium diisopropylamide (13.5 ml, 24.3 mmol, 1.8 M in hexane/THF/ethylbenzene) is added dropwise over a period of 20 minutes. The resultant solution is stirred for 30 minutes at −78° C. before adding the 4-benzyloxy-cyclohexanecarbaldehyde (4.74 g, 21.7 mmol) dissolved in tetrahydrofuran (30 ml). The reaction mixture is stirred for 30 minutes and then allowed to warm to room temperature. The reaction mixture is then poured into a saturated aqueous solution of ammonium chloride and extracted with ethyl acetate (2×200 ml). The combined organic extract are dried over magnesium sulphate, filtered and evaporated under reduced pressure to give an orange oil. The residue is purified by flash chromatography to give 5-[(4-benzyloxy-cyclohexyl)-hydroxy-methyl]-3-methoxy-2-(2,4,6-trimethyl-phenyl)-cyclopent-2-enone (6.7 g).

Step 6

Preparation of 4-[1-(4-benzyloxy-cyclohexyl)-meth-(E)-ylidene]-2-(2,4,6-trimethyl-phenyl)-cyclopentane-1,3-dione

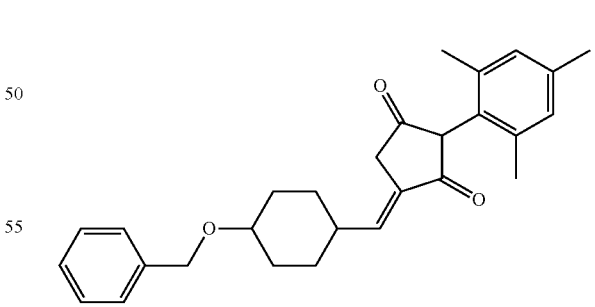

Into six 20 ml microwave vials is added the 5-[(4-benzyloxy-cyclohexyl)-hydroxy-methyl]-3-methoxy-2-(2,4,6-trimethyl-phenyl)-cyclopent-2-enone (1 g, 2.2 mmol) in a mixture of acetone (7.5 ml) and 2N aqueous hydrochloric acid (7.5 ml). Each vial is therefore heated for 1 hour to 120° C. by microwave irradiation. The reaction mixtures were then combined and diluted with water (100 ml) and extracted with dichloromethane (2×50 m). The combined organic extracts are dried over magnesium sulphate, filtered and evaporated under reduced pressure to give a yellow gum. The gum is purified by flash chromatography to give 4-[1-(4-benzyloxy-cyclohexyl)-meth-(E)-ylidene]-2-(2,4,6-trimethyl-phenyl)-cyclopentane-1,3-dione (4.3 g).

Step 7

Preparation of 2,2-dimethyl-propionic acid 4-[1-(4-benzyloxy-cyclohexyl)-meth-(E)-ylidene]-3-oxo-2-(2,4,6-trimethyl-phenyl)-cyclopentyl ester

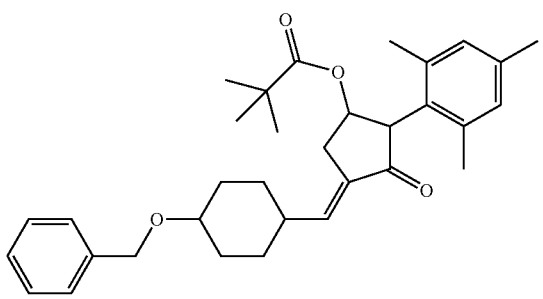 [SMILES: Cc1cc(C)c(C2C(=O)/C(=C/C3CCC(OCc4ccccc4)CC3)CC2OC(=O)C(C)(C)C)c(C)c1]

To a solution of the 4-[1-(4-benzyloxy-cyclohexyl)-meth-(E)-ylidene]-2-(2,4,6-trimethyl-phenyl)-cyclopentane-1,3-dione (4.0 g, 9.6 mmol) in dichloromethane (60 ml) and triethylamine (2 ml) is added the pivaloyl chloride (1.73 g, 14.3 mmol) at 0° C. The reaction is allowed to warm to room temperature and then stirred for 3 hours. The reaction mixture is poured into water (50 ml) and extracted with dichloromethane (2×50 ml). The combined organic extracts are dried over magnesium sulphate, filtered and evaporated to give 2,2-dimethyl-propionic acid 4-[1-(4-benzyloxy-cyclohexyl)-meth-(E)-ylidene]-3-oxo-2-(2,4,6-trimethyl-phenyl)-cyclopentyl ester (4.5 g).

Step 8

Preparation of 2,2-dimethyl-propionic acid 4-(4-hydroxy-cyclohexylmethyl)-3-oxo-2-(2,4,6-trimethyl-phenyl)-cyclopentyl ester

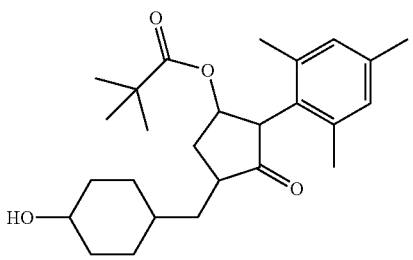 [SMILES: Cc1cc(C)c(C2C(=O)C(CC3CCC(O)CC3)CC2OC(=O)C(C)(C)C)c(C)c1]

The 2,2-dimethyl-propionic acid 4-[1-(4-benzyloxy-cyclohexyl)-meth-(E)-ylidene]-3-oxo-2-(2,4,6-trimethyl-phenyl)-cyclopentyl ester (4.5 g, 9.0 mmol) is dissolved in ethyl acetate (40 ml), 1 g of 5% palladium on carbon is added and the reaction mixture is placed under hydrogen pressure (3 bars) for 3 hours. The reaction mixture is filtered and washed with ethyl acetate. The filtrate is absorbed onto silica gel and purified by flash chromatography to give a sticky solid. The solid was crystallised from hexane to give 2,2-dimethyl-propionic acid 4-(4-hydroxy-cyclohexylmethyl)-3-oxo-2-(2,4,6-trimethyl-phenyl)-cyclopentyl ester (1.37 g).

Step 9

Preparation of 2,2-dimethyl-propionic acid 3-oxo-4-(4-oxo-cyclohexylmethyl)-2-(2,4,6-trimethyl-phenyl)-cyclopentyl ester

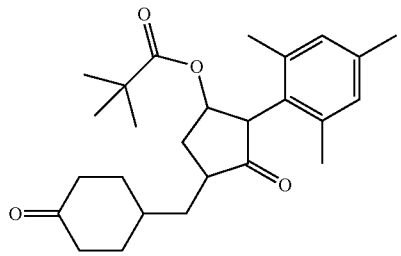 [SMILES: Cc1cc(C)c(C2C(=O)C(CC3CCC(=O)CC3)CC2OC(=O)C(C)(C)C)c(C)c1]

The 2,2-dimethyl-propionic acid 4-(4-hydroxy-cyclohexylmethyl)-3-oxo-2-(2,4,6-trimethyl-phenyl)-cyclopentyl ester (100 mg) is dissolved in acetone and cooled to 0° C. The Jones reagent (1.3 ml, 167 M) is added dropwise over a period of 30 minutes. The reaction is allowed to warm to room temperature over 1 hour. The reaction is poured into water and extracted with ethyl acetate (3×50 ml). The combined organic extracts are washed with a saturated aqueous solution of sodium bicarbonate, dried over magnesium sulphate, filtered and the solvents were removed under reduced pressure to give a white crystalline solid. The solid is purified by flash chromatography to give the 2,2-dimethyl-propionic acid 3-oxo-4-(4-oxo-cyclohexylmethyl)-2-(2,4,6-trimethyl-phenyl)-cyclopentyl ester (72 mg).

Step 10

Preparation of 2,2-dimethyl-propionic acid 4-(4-methoxyimino-cyclohexylmethyl)-3-oxo-2-(2,4,6-trimethyl-phenyl)-cyclopentyl ester

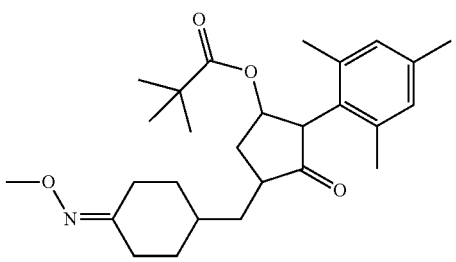

2,2-dimethyl-propionic acid 3-oxo-4-(4-oxo-cyclohexylmethyl)-2-(2,4,6-trimethyl-phenyl)-cyclopentyl ester (150 mg, 0.36 mmol) is dissolved in ethanol (8 ml) and hydroxylamine hydrochloride (36 mg, 0.43 mmol) is added. The solution is stirred while adding pyridine (32 mg, 0.40 mmol). The reaction mixture is heated to reflux for 2 hours. The reaction mixture is diluted with water and extracted with dichloromethane (1×40 ml). The organic extract is dried over magnesium sulphate, filtered and evaporated to a brown gum. The product is purified by HPLC to give 2,2-dimethyl-propionic acid 4-(4-methoxyimino-cyclohexylmethyl)-3-oxo-2-(2,4,6-trimethyl-phenyl)-cyclopentyl ester.

Example 2

Preparation of 4-cyclohexylmethyl-2-(2,6-dimethyl-phenyl)-cyclopentane-1,3-dione

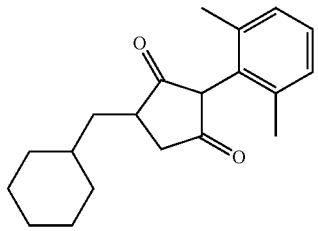 [SMILES: Cc1cccc(C)c1C1C(=O)CC(CC2CCCCC2)C1=O]

Step 1

Preparation of 2-(4-bromo-2,6-dimethyl-phenyl)-5-(cyclohexyl-hydroxy-methyl)-3-methoxy-cyclopent-2-enone

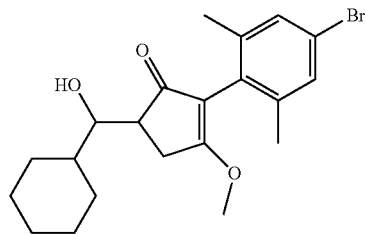 [SMILES: COC1=C(c2c(C)cc(Br)cc2C)C(=O)C(C(O)C2CCCCC2)C1]

To a solution of 2-(4-bromo-2,6-dimethyl-phenyl)-3-methoxy-cyclopent-2-enone (1 g, 3.4 mmol) in 10 ml of dry tetrahydrofuran under nitrogen atmosphere at −78° C. LiHMDS (4.42 ml, 4.42 mmol) is added slowly and it is stirred at −78° C. for 40 minutes. A solution of cyclohexyl carboxaldehyde (761 mg, 6.8 mmol) in dry tetrahydrofuran (10 ml) is added to the reaction mixture at −78° C. The reaction mixture is stirred at this temperature for 2 hours and then at room temperature for 3 hours. The reaction mixture is quenched with water (50 ml) and the aqueous layer is extracted with ethyl acetate (3*100 ml). The combined organic layers are dried with sodium sulfate and concentrated under vacuum to obtain crude product which is directly taken to the next step without further purification.

Step 2

Preparation of 2-(4-bromo-2,6-dimethyl-phenyl)-4-[1-cyclohexyl-meth-(E)-ylidene]-cyclopentane-1,3-dione

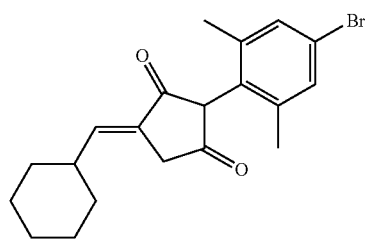 [SMILES: Cc1cc(Br)cc(C)c1C1C(=O)C/C(=C\C2CCCCC2)C1=O]

A solution of 2-(4-bromo-2,6-dimethyl-phenyl)-5-(cyclohexyl-hydroxy-methyl)-3-methoxy-cyclopent-2-enone (1.38 g, 3.4 mmol) in ethanol (27.6 ml) and 2N aqueous hydrochloric acid (13.8 ml) is subjected to microwave irradiation at 130° C. for 40 minutes. The reaction mixture is concentrated under vacuum to remove ethanol. The aqueous layer was extracted with ethyl acetate (3×100 ml) and combined organic layers are dried with sodium sulfate and concentrated under vacuum to obtain crude mass. The compound was purified by column chromatography to give 2-(4-bromo-2,6-dimethyl-phenyl)-4-[1-cyclohexyl-meth-(E)-ylidene]-cyclopentane-1,3-dione (250 mg).

Step 3

Preparation of 4-cyclohexylmethyl-2-(2,6-dimethyl-phenyl)-cyclopentane-1,3-dione

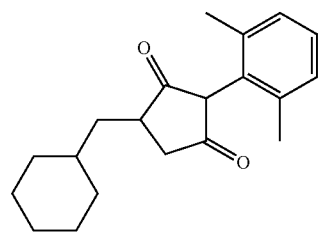 [SMILES: Cc1cccc(C)c1C1C(=O)CC(CC2CCCCC2)C1=O]

To a solution of 2-(4-bromo-2,6-dimethyl-phenyl)-4-[1-cyclohexyl-meth-(E)-ylidene]-cyclopentane-1,3-dione (250 mg, 0.844 mmol) in methanol (25 ml) was added 10% palladium on carbon (50 mg, 20%) and stirred at room temperature under hydrogen balloon pressure for 7-8 hours. The reaction mixture was filtered through celite bed, concentrated under high vacuum. Compounds were separated by auto prep purification system to give 4-cyclohexylmethyl-2-(2,6-dimethyl-phenyl)-cyclopentane-1,3-dione.

Example 3

Preparation of 2,2-dimethyl-propionic acid 4-(4-fluoro-benzyl)-3-oxo-2-(2,4,6-trimethyl-phenyl)-cyclopent-1-enyl ester

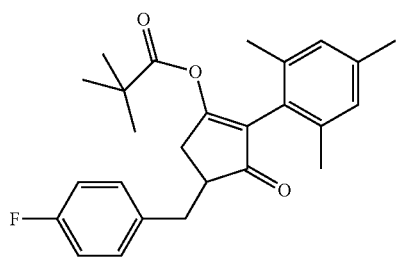 [SMILES: Cc1cc(C)c(C2=C(OC(=O)C(C)(C)C)CC(Cc3ccc(F)cc3)C2=O)c(C)c1]

Step 1

Preparation of 5-(4-Fluoro-benzyl)-3-methoxy-2-(2,4,6-trimethyl-phenyl)-cyclopent-2-enone

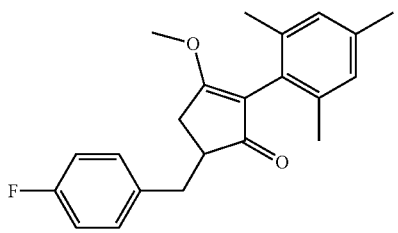 [SMILES: COC1=C(c2c(C)cc(C)cc2C)C(=O)C(Cc2ccc(F)cc2)C1]

To a solution of 3-methoxy-2-(2,4,6-trimethyl-phenyl)-cyclopent-2-enone (200 mg, 0.86 mmol) in THF (3 ml) under $N_2$ at −78° C. is added, dropwise, a 1.8 M solution of lithium diisopropylamine in tetrahydrofuran/heptane/ethylbenzene (0.53 ml, 0.95 mmol). The resulting solution is allowed to stir at −78° C. for 40 minutes. A solution of 4-fluorobenzyl bromide (0.16 ml, 1.3 mmol) in THF (1 ml) is then added in one portion, the reaction mixture is stirred at −78° C. for 30 minutes before being allowed to warm to room temperature over a period of 60 minutes. The reaction is quenched by the addition of saturated aqueous ammonium chloride (5 ml) and extracted with ethyl acetate (2×10 ml). The combined organics are purified by flash chromatography to give 5-(4-fluoro-benzyl)-3-methoxy-2-(2,4,6-trimethyl-phenyl)-cyclopent-2-enone (236 mg).

Step 2

Preparation of 4-(4-fluoro-benzyl)-2-(2,4,6-trimethyl-phenyl)-cyclopentane-1,3-dione

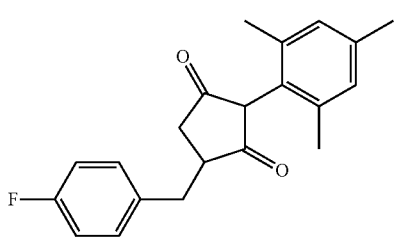 [SMILES: Cc1cc(C)c(C2C(=O)CC(Cc3ccc(F)cc3)C2=O)c(C)c1]

To a solution of 5-(4-fluoro-benzyl)-3-methoxy-2-(2,4,6-trimethyl-phenyl)-cyclopent-2-enone (136 mg, 0.40 mmol) in acetone (2 ml) is added a 2N solution of hydrochloric acid (2 ml) and the resulting solution is heated to 40° C. by microwave irradiation for 30 minutes. The reaction mixture is diluted with 2N hydrochloric acid (25 ml), and extracted with ethyl acetate (2×25 ml). The combined organics are washed with brine (25 ml), dried over magnesium sulphate, filtered and concentrated in vacuo to give 4-(4-fluoro-benzyl)-2-(2,4,6-trimethyl-phenyl)-cyclopentane-1,3-dione (124 mg).

Step 3

Preparation of 2,2-dimethyl-propionic acid 4-(4-fluoro-benzyl)-3-oxo-2-(2,4,6-trimethyl-phenyl)-cyclopent-1-enyl ester

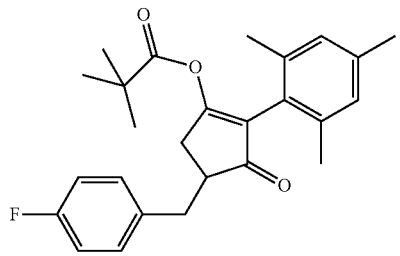 [SMILES: Cc1cc(C)c(C2=C(OC(=O)C(C)(C)C)CC(Cc3ccc(F)cc3)C2=O)c(C)c1]

To a solution of 4-(4-fluoro-benzyl)-2-(2,4,6-trimethyl-phenyl)-cyclopentane-1,3-dione (30 mg, 0.09 mmol) in dichloromethane (1 ml) and triethylamine (52 µl, 0.37 mmol) is added the pivaloyl chloride (34 µl, 0.37 mmol) at room temperature. The reaction mixture is stirred overnight at room temperature. Silica gel is added to the crude reaction mixture, the solvent is evaporated under reduced pressure and the residue is purified by flash chromatography on silica gel to give 2,2-dimethyl-propionic acid 4-(4-fluoro-benzyl)-3-oxo-2-(2,4,6-trimethyl-phenyl)-cyclopent-1-enyl ester (31 mg).

Example 4

Preparation of 4-cycloheptylmethyl-2-(2,4,6-trimethyl-phenyl)-cyclopentane-1,3-dione

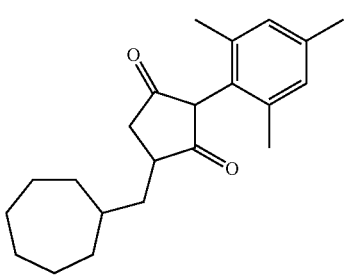 [SMILES: Cc1cc(C)c(C2C(=O)CC(CC3CCCCCC3)C2=O)c(C)c1]

Step 1

Preparation of cycloheptyl-methanol

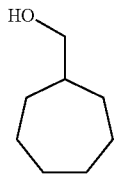

To an oven-dried, three-necked flask under an N₂ atmosphere was added LiAlH₄ (4.0 g, 0.11 mol) followed by anhydrous Et₂O (100 ml). To the stirred suspension was added dropwise over 1 hour a solution of cycloheptane carboxylic acid (5.0 g, 0.035 mol) in anhydrous Et₂O (50 ml). The reaction was stirred at room temperature for 2 hours and then cooled with an ice bath. H₂O (4 ml) was added cautiously dropwise over 20 minutes, followed by cautious dropwise addition of NaOH (4 ml of a 15% aqueous solution) and then dropwise addition of further H₂O (12 ml). The reaction was stirred vigorously for 5 minutes and the resultant white precipitate was removed by filtration and washed with copious Et₂O. The combined filtrate and washings were evaporated to dryness under reduced pressure to yield the desired compound (3.74 g) as a colourless oil with no need for further purification.

Step 2

Preparation of cycloheptanecarbaldehyde

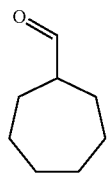

To a stirred solution of cycloheptyl-methanol (1.28 g, 0.01 mol) in CH₂Cl₂ (50 ml) at room temperature was added portionwise PCC (3.23 g, 0.015 mol). The reaction turned almost instantly dark brown as was stirred at room temperature for 4 hours. The reaction was then diluted with Et₂O (50 ml) and the solvent decanted away from the solid residue. The residue was washed with further Et₂O (2×25 ml). The reaction mixture and combined washing were then filtered through a 10 g SiO₂ chromatography cartridge and washed through with further Et₂O (25 ml). The solvent was then removed under reduced pressure to yield the desired compound (1.08 g) as a colourless, pungent oil which was used without further purification.

Step 3

Preparation of 5-(Cycloheptyl-hydroxy-methyl)-3-methoxy-2-(2,4,6-trimethyl-phenyl)-cyclopent-2-enone

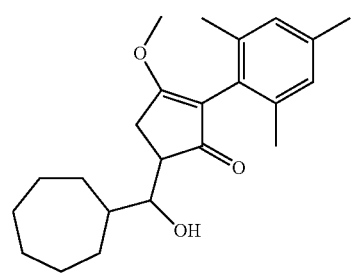 [SMILES: COC1=C(c2c(C)cc(C)cc2C)C(=O)C(C(O)C2CCCCCC2)C1]

To a stirred solution of 3-methoxy-2-(2,4,6-trimethyl-phenyl)-cyclopent-2-enone (0.46 g, 2.0 mmol) in anhydrous THF (20 ml) at −78 C under an N₂ atmosphere was added dropwise a solution of lithium diisopropylamide (1.22 ml of a 1.8M solution in THF/heptanes/ethyl benzene, 2.2 mmol). The reaction was stirred at −78 C for 90 minutes and then a solution of cycloheptanecarbaldehyde (316 mg, 2.5 mmol) in anhydrous THF (3 ml) was added dropwise. The reaction was stirred at −78 C for a further 30 minutes and then allowed to warm to room temperature over 30 minutes. The reaction was quenched by addition of H₂O (25 ml) and extracted with EtOAc (3×20 ml). The combined organic extracts were washed with brine (15 ml), dried over MgSO₄, filtered and evaporated to dryness under reduced pressure to give a brown oil (628 mg). The crude material was purified by flash chromatography over SiO₂ using a 100% isohexane to 100% EtOAc gradient to give the desired product as a colourless oil (101 mg).

Step 4

Preparation of 4-[1-Cycloheptyl-methylidene]-2-(2,4,6-trimethyl-phenyl)-cyclopentane-1,3-dione

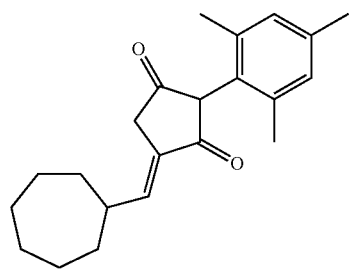 [SMILES: Cc1cc(C)c(C2C(=O)C/C(=C\C3CCCCCC3)C2=O)c(C)c1]

To a solution of 5-(Cycloheptyl-hydroxy-methyl)-3-methoxy-2-(2,4,6-trimethyl-phenyl)-cyclopent-2-enone (100 mg, 0.28 mmol) in acetone (4 ml) in a 10 ml vial was added 2M HCl (4 ml). The reaction was capped and heated to 120 C for 30 minutes under microwave irradiation. The reaction was diluted with H₂O (20 ml) and extracted with EtOAc (3×15 ml). The combined organic extracts were washed with brine (10 ml), dried over MgSO₄, filtered and evaporated to dryness under reduced pressure to give a brown oil (88 mg). The crude material was purified by flash chromatography over SiO₂ using a 100% isohexane to 100% EtOAc gradient to give the desired product as a colourless oil (62 mg).

Step 5

Preparation of 4-Cycloheptylmethyl-2-(2,4,6-trimethyl-phenyl)-cyclopentane-1,3-dione

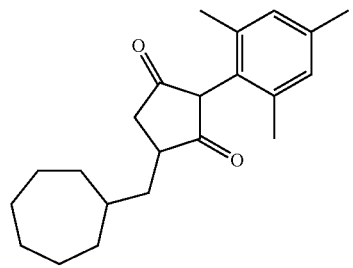 [SMILES: Cc1cc(C)c(C2C(=O)CC(CC3CCCCCC3)C2=O)c(C)c1]

To 5% w/w Pd/C (5 mg) was added a solution of 4-[1-Cycloheptyl-methylidene]-2-(2,4,6-trimethyl-phenyl)-cyclopentane-1,3-dione (39 mg, 0.12 mmol) in MeOH (10 ml). The reaction was stirred under an atmosphere of H$_2$ (1.5 bar) for 2 hours, filtered through a pad of celite and washed through with MeOH (20 ml). The solvent was removed under reduced pressure to give the desired product as a colourless oil (29 mg) without need for further purification.

Example 5

Preparation of 4-Cyclopropylmethyl-2-(2,4,6-trimethyl-phenyl)-cyclopentane-1,3-dione

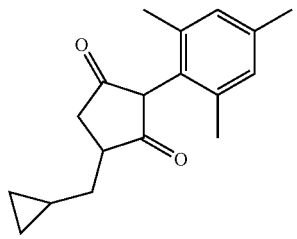 [SMILES: Cc1cc(C)c(C2C(=O)CC(CC3CC3)C2=O)c(C)c1]

Step 1

Preparation of 5-(Cyclopropyl-hydroxy-methyl)-3-methoxy-2-(2,4,6-trimethyl-phenyl)-cyclopent-2-enone

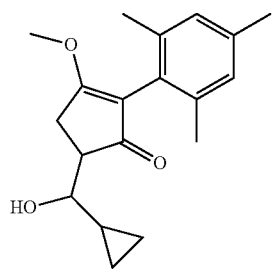 [SMILES: COC1=C(c2c(C)cc(C)cc2C)C(=O)C(C(O)C2CC2)C1]

To a stirred solution of 3-methoxy-2-(2,4,6-trimethyl-phenyl)-cyclopent-2-enone (0.69, 3.0 mmol) in anhydrous THF (10 ml) at −78 C under an N$_2$ atmosphere was added dropwise a solution of lithium diisopropylamide (1.75 ml of a 1.8M solution in THF/heptanes/ethyl benzene, 3.15 mmol). The reaction was stirred at −78 C for 60 minutes and then cyclopropanecarbaldehyde (0.27 ml, 3.6 mmol) was added dropwise. The reaction was stirred at −78 C for a further 30 minutes and then allowed to warm to room temperature over 210 minutes. The reaction was quenched by addition of H$_2$O (50 ml) and extracted with EtOAc (50 ml). The organic phase was washed with H$_2$O (50 ml) and brine (50 ml), dried over MgSO$_4$, filtered and evaporated to dryness under reduced pressure to give a brown oil (1.37 g). The crude material was purified by flash chromatography over SiO$_2$ using a 100% isohexane to 100% EtOAc gradient to give the desired product (mix of diastereomers) as a colourless oil (622 mg).

Step 2

Preparation of 5-[1-Cyclopropyl-methylidene]-3-methoxy-2-(2,4,6-trimethyl-phenyl)-cyclopent-2-enone

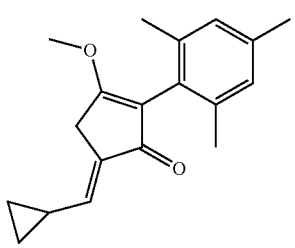 [SMILES: COC1=C(c2c(C)cc(C)cc2C)C(=O)/C(=C/C2CC2)C1]

To a solution of 5-(Cyclopropyl-hydroxy-methyl)-3-methoxy-2-(2,4,6-trimethyl-phenyl)-cyclopent-2-enone (622 mg, 2.1 mmol) in CH$_2$Cl$_2$ (10 ml) at 0 C were added dropwise Et$_3$N (0.59 ml, 4.2 mmol) followed my methane sulfonyl chloride (0.33 ml, 4.2 mmol). The reaction was allowed to warm to room temperature over 10 minutes and then quenched by addition of 1M HCl (10 ml). The layers were separated and the organic phase was evaporated to dryness under reduced pressure. The crude mesylate was dissolved in MeOH (10 ml) and K$_2$CO$_3$ (580 mg, 4.2 mmol) was added in a single portion. The reaction was stirred at room temperature for 2 hours and then the solvent was removed under reduced pressure. The crude material was partitioned between EtOAc (20 ml) and H$_2$O (20 ml), the organic phase was washed with brine (20 ml), dried over MgSO$_4$, filtered and evaporated to dryness under reduced pressure. The crude material was purified by flash chromatography over SiO$_2$ using a 100% isohexane to 100% EtOAc gradient to give the desired product as a colourless oil (83 mg).

Step 3

Preparation of 4-[1-Cyclopropyl-methylidene]-2-(2,4,6-trimethyl-phenyl)-cyclopentane-1,3-dione

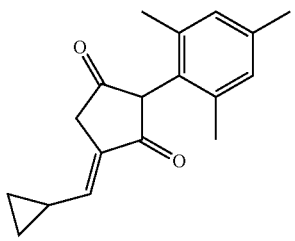

A solution of 5-[1-Cyclopropyl-methylidene]-3-methoxy-2-(2,4,6-trimethyl-phenyl)-cyclopent-2-enone (83 mg, 0.28 mmol) in morpholine (3 ml) was heated at 10° C. for 17 hours. The reaction was allowed to cool to room temperature and then evaporated to dryness under reduced pressure. The crude material was dissolved in EtOAc (15 ml) and then washed with 2M HCl (3×15 ml) and brine (15 ml). The organic phase was dried over Na$_2$SO$_4$, filtered and evaporated to dryness

Step 4

Preparation of 4-Cyclopropylmethyl-2-(2,4,6-trimethyl-phenyl)-cyclopentane-1,3-dione

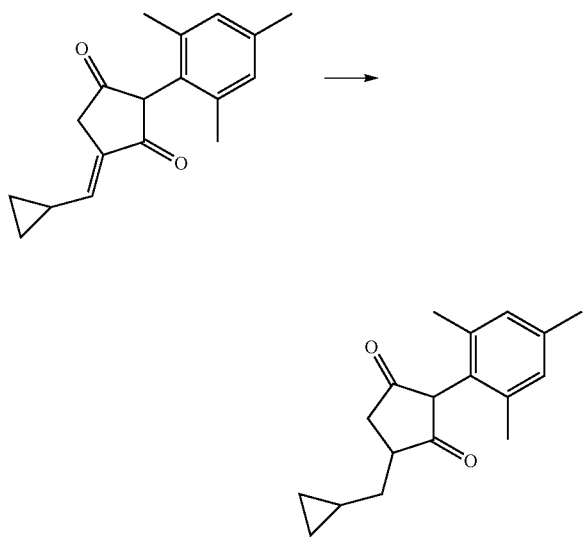 [SMILES: Cc1cc(C)c(C2C(=O)C/C(=C\C3CC3)C2=O)c(C)c1 ; Cc1cc(C)c(C2C(=O)CC(CC3CC3)C2=O)c(C)c1]

To 5% w/w Pd/C (5 mg) was added a solution of 4-[1-cyclopropyl-methylidene]-2-(2,4,6-trimethyl-phenyl)-cyclopentane-1,3-dione (28 mg, 0.09 mmol) in MeOH (10 ml). The reaction was stirred under an atmosphere of $H_2$ (1.5 bar) for 1.5 hours, filtered through a pad of celite and washed through with MeOH (20 ml). The solvent was removed under reduced pressure to give the crude product (20 mg) which was purified by mass-directed HPLC to give the desired product (5 mg).

Example 6

Preparation of 4-(4-Methoxy-cyclohexylmethyl)-2-(2,4,6-trimethyl-phenyl)-cyclopentane-1,3-dione

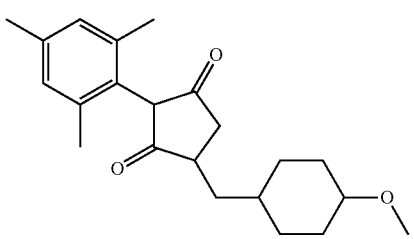

Step 1

Preparation of 4-methoxy-cyclohexanecarbaldehyde

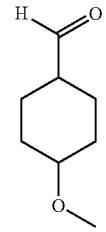

To a stirred suspension of methoxymethyl triphenylphosphonium chloride (20.8 g, 60 mmol) in dry THF (60 ml) is added dropwise to a solution of lithium diisopropylamide (38 ml, 69 mmol, 1.8 M in hexane/THF/ethylbenzene), at 0-5° C. The resulting reaction mixture is stirred for 30 minutes and then cooled to −78° C. At this temperature, a solution of methoxycyclohexanone (6 g, 47 mmol) in tetrahydrofuran (600 ml) is added over a period of 30 minutes. Once the addition is completed the reaction mixture is stirred at −78° C. for 1 hour and then allowed to warm to room temperature and stirred overnight. The reaction mixture is then diluted to pH=2 with a 2N aqueous solution of hydrochloric acid and stirred for 3 hours at room temperature. The reaction was diluted with water and extracted with ethyl acetate. The combined organic extracts are dried over magnesium sulfate, filtered and evaporated under reduced pressure. The residue is purified by flash chromatography to give 4-benzyloxy-cyclohexanecarbaldehyde (5.1 g).

Step 2

Preparation of 5-[Hydroxy-(4-methoxy-cyclohexyl)-methyl]-3-methoxy-2-(2,4,6-trimethyl-phenyl)-cyclopent-2-enone

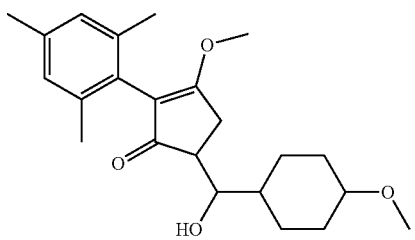

To a solution of 3-methoxy-2-(2,4,6-trimethyl-phenyl)-cyclopent-2-enone (2 g, 8.7 mmol) in dry tetrahydrofuran (25 ml) at −78° C. is added a solution of lithium diisopropylamide (5.8 ml, 10.4 mmol, 1.8 M in hexane/THF/ethylbenzene) dropwise over 20 minutes. The resultant solution is stirred for 30 minutes at −78° C. before adding 4-methoxy-cyclohexanecarbaldehyde (1.4 g, 9.8 mmol) dissolved in tetrahydrofuran (15 ml). The reaction mixture is allowed to warm to room temperature overnight then diluted with water, acidified with 2 N HCl and extracted with ethyl acetate (3×15 ml). The combined organic extract are dried over magnesium sulfate, filtered and evaporated under reduced pressure to give an brown oil. The residue is purified by flash chromatography to 5-[Hydroxy-(4-methoxy-cyclohexyl)-methyl]-3-methoxy-2-(2,4,6-trimethyl-phenyl)-cyclopent-2-enone (1.7 g).

Step 3

Preparation of 4-[1-(4-Methoxy-cyclohexyl)-meth-(E)-ylidene]-2-(2,4,6-trimethyl-phenyl)-cyclopentane-1,3-dione

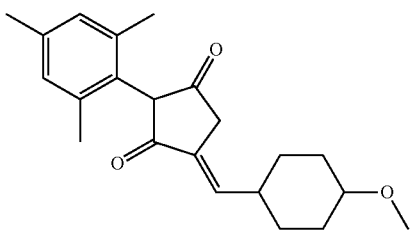

To a solution of 5-[(4-benzyloxy-cyclohexyl)-hydroxymethyl]-3-methoxy-2-(2,4,6-trimethyl-phenyl)-cyclopent-2-enone (1.5 g, 4.0 mmol) in acetone (3 ml) is added 2N aqueous hydrochloric acid (3 ml) and the mixture heated for 1 hour at 120° C. by microwave irradiation. The reaction mixtures is then diluted with water (20 ml) and extracted with ethyl acetate (3×15 ml). The combined organic extracts are dried over magnesium sulfate, filtered and evaporated under reduced pressure to give a brown gum. The gum is purified by flash chromatography eluting with hexane/ethyl acetate to give 4-[1-(4-Methoxy-cyclohexyl)-meth-(E)-ylidene]-2-(2,4,6-trimethyl-phenyl)-cyclopentane-1,3-dione as a colourless solid (0.32 g).

Step 4

Preparation of 4-(4-Methoxy-cyclohexylmethyl)-2-(2,4,6-trimethyl-phenyl)-cyclopentane-1,3-dione

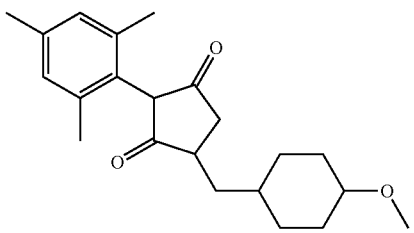

To a mixture of 4-[1-(4-Methoxy-cyclohexyl)-meth-(E)-ylidene]-2-(2,4,6-trimethyl-phenyl)-cyclopentane-1,3-dione (150 mg, 0.44 mmol) and ethanol (3.5 ml) is added 5% palladium on carbon (30 mg) and the resulting mixture hydrogenated at 3 bar pressure for 3 hours. The reaction mixture is then filtered through celite and the filtrate concentrated under reduced pressure to give 4-(4-Methoxy-cyclohexylmethyl)-2-(2,4,6-trimethyl-phenyl)-cyclopentane-1,3-dione as a pale yellow solid (142 mg).

Unless otherwise stated, proton NMR spectra were recorded at ambient temperature.

Compounds characterised by HPLC-MS were analysed using one of three methods described below.

Method A

Compounds characterised by HPLC-MS were analysed using a Waters 2795 HPLC equipped with a Waters Atlantis dC18 column (column length 20 mm, internal diameter of column 3 mm, particle size 3 micron, temperature 40° C.), Waters photodiode array and Micromass ZQ2000. The analysis was conducted using a three minutes run time, according to the following gradient table:

| Time (mins) | Solvent A (%) | Solvent B (%) | Flow (ml/mn) |
|---|---|---|---|
| 0.00 | 90.0 | 10.0 | 2.00 |
| 0.25 | 90.0 | 10.0 | 2.00 |
| 2.00 | 10.0 | 90.0 | 2.00 |
| 2.50 | 10.0 | 90.0 | 2.00 |
| 2.60 | 90.0 | 10.0 | 2.00 |
| 3.0 | 90.0 | 10.0 | 2.00 |

Solvent A: $H_2O$ containing 0.1% HCOOH
Solvent B: $CH_3CN$ containing 0.1% HCOOH Method B Compounds characterised by HPLC-MS were analysed using an Waters 2777 injector with a 1525 micro pump HPLC equipped with a Waters Atlantis dC18 IS column (column length 20 mm, internal diameter of column 3 mm, particle size 3 micron), Waters 2996 photodiode array, Waters 2420 ELSD and Micromass ZQ2000. The analysis was conducted using a three minutes run time, according to the following gradient table:

| Time (mins) | Solvent A (%) | Solvent B (%) | Flow (ml/mn) |
|---|---|---|---|
| 0.00 | 95.0 | 5 | 1.300 |
| 2.50 | 0.00 | 100 | 1.300 |
| 2.80 | 0.00 | 100 | 1.300 |
| 2.90 | 95.0 | 5 | 1.300 |

Solvent A: $H_2O$ with 0.05% TFA
Solvent B: $CH_3CN$ with 0.05% TFA

Method C:

Compounds characterised by HPLC-MS were analysed using a Finnigan Surveyor MSQ Plus equipped with a Waters Xterra column (column length 50 mm, internal diameter of column 4.6 mm, particle size 3.5 micron, temperature 40° C.), Waters photodiode array and Micromass ZQ2000. The analysis was conducted using a six minutes run time, according to the following gradient table:

| Time (mins) | Solvent A (%) | Solvent B (%) | Flow (ml/mn) |
|---|---|---|---|
| 0.00 | 90.0 | 10.0 | 1.30 |
| 3.80 | 0.00 | 100 | 1.30 |
| 4.80 | 0.00 | 100 | 1.30 |
| 5.00 | 90.0 | 10.0 | 1.30 |
| 6.00 | 90.0 | 10.0 | 1.30 |

Solvent A: $H_2O$ containing 0.05% HCOOH
Solvent B: $CH_3CN$ containing 0.05% HCOOH Method D Compounds characterised by HPLC-MS were analysed using a Waters Acquity HPLC equipped with a Waters Atlantis dC18 column (column length 20 mm, internal diameter of column 3 mm, particle size 3 micron, temperature 40° C.), Waters photodiode array and Micromass ZQ2000. The analysis was conducted using a two minute run time, according to the following gradient table:

| Time (mins) | Solvent A (%) | Solvent B (%) | Flow (ml/mn) |
|---|---|---|---|
| 0.00 | 90.0 | 10.0 | 2.00 |
| 1.50 | 10.0 | 90.0 | 2.00 |
| 1.75 | 10.0 | 90.0 | 2.00 |
| 1.9 | 90.0 | 10.0 | 2.00 |
| 2.00 | 90.0 | 10.0 | 2.00 |

Solvent A: $H_2O$ containing 0.1% HCOOH
Solvent B: $CH_3CN$ containing 0.1% HCOOH

TABLE A1

| Compound Number | Structure | LC/MS, NMR or other physical data |
|---|---|---|
| A1 | 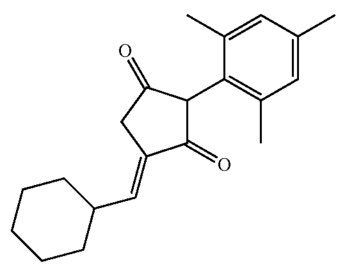 [SMILES: Cc1cc(C)c(C2C(=O)C/C(=C\C3CCCCC3)C2=O)c(C)c1] | LC/MS (Method A) $ES^+$: $MH^+$ = 311 rt = 1.76 min |
| A2 | 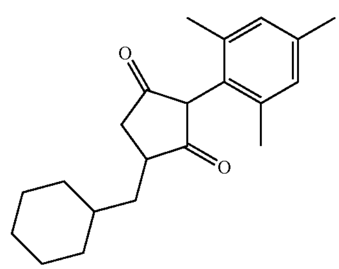 [SMILES: Cc1cc(C)c(C2C(=O)CC(CC3CCCCC3)C2=O)c(C)c1] | LC/MS (Method A) $ES^+$: $MH^+$ = 313 rt = 1.73 min |
| A3 | 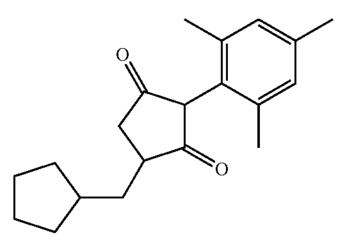 [SMILES: Cc1cc(C)c(C2C(=O)CC(CC3CCCC3)C2=O)c(C)c1] | LC/MS (Method A) $ES^+$: $MH^+$ = 299 rt = 1.64 min |
| A4 | 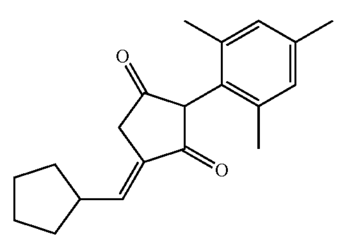 [SMILES: Cc1cc(C)c(C2C(=O)C/C(=C\C3CCCC3)C2=O)c(C)c1] | LC/MS (Method A) $ES^+$: $MH^+$ = 297 rt = 1.68 min |

TABLE A1-continued
Compounds A1 to A47
| Compound Number | Structure | LC/MS, NMR or other physical data |
| --- | --- | --- |
| A5 | 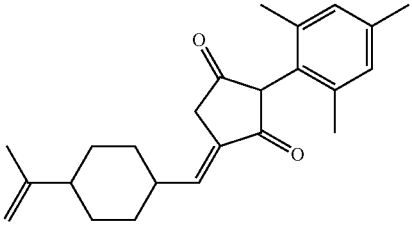 [SMILES: C=C(C)C1CCC(/C=C2\CC(=O)C(c3c(C)cc(C)cc3C)C2=O)CC1] | LC/MS (Method A) ES+: MH+ = 351 rt = 1.79 |
| A6 | 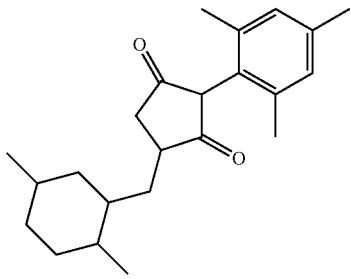 | LC/MS (Method A) ES+: MH+ = 341 rt = 1.91 min |
| A7 | 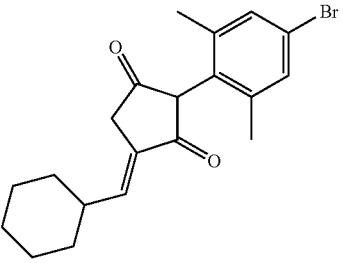 [SMILES: Cc1cc(Br)cc(C)c1C1C(=O)C/C(=C\C2CCCCC2)C1=O] | LC/MS (Method C) ES−: M − H+ = 377, 375 rt = 4.8 min |
| A8 | 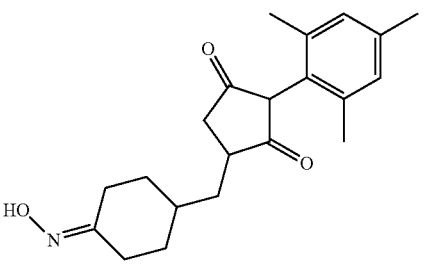 [SMILES: Cc1cc(C)c(C2C(=O)CC(CC3CCC(=NO)CC3)C2=O)c(C)c1] | LC/MS (Method B) ES+: MH+ = 342 rt = 1.28 min |
| A9 | 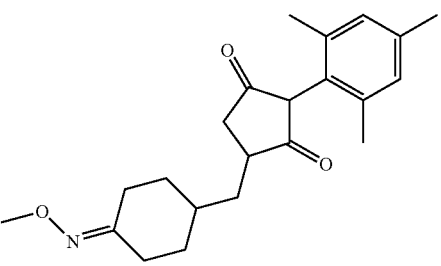 | LC/MS (Method B) ES+: MH+ = 356 rt = 1.45 min |

TABLE A1-continued

Compounds A1 to A47

| Compound Number | Structure | LC/MS, NMR or other physical data |
|---|---|---|
| A10 | 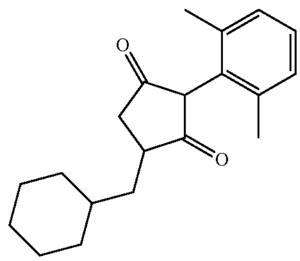 [SMILES: Cc1cccc(C)c1C1C(=O)CC(CC2CCCCC2)C1=O] | LC/MS (Method C) ES+: MH+ = 297<br>rt = 4.42 min<br>δ ppm 7.14 (m, 1H); 7.07 (m, 2H); 6.5 (br s, 1H); 2.8-3.0 (m, 2H); 2.2-2.4 (m, 1H); 2.1 (s, 6H); 1.7-1.9 (m, 6H); 1.4 (m, 1H); 1.1-1.4 (m, 6H) |
| A11 | 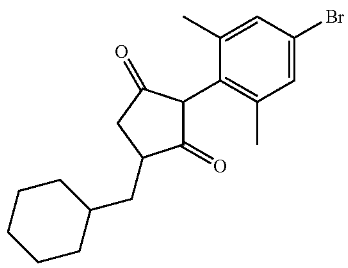 [SMILES: Cc1cc(Br)cc(C)c1C1C(=O)CC(CC2CCCCC2)C1=O] | LC/MS (Method C) ES−: M − H+ = 377, 375<br>rt = 4.8 min<br>δ ppm 7.25 (s, 2H); 2.8 (m, 2H); 2.36 (m, 1H); 2.09 (s, 6H); 1.6-1.8 (m, 6H); 1.4 (m, 1H); 1.2-1.3 (m, 6H) |
| A12 | 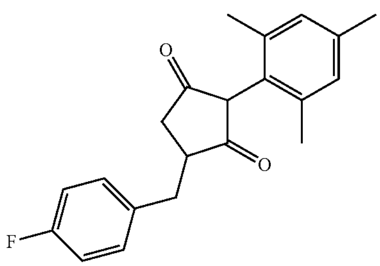 [SMILES: Cc1cc(C)c(C2C(=O)CC(Cc3ccc(F)cc3)C2=O)c(C)c1] | δ 7.27-7.18 (m, 2H), 7.11-7.02 (m, 2H), 6.90 (s, 2H), 6.71 (bs, 1H), 3.39-2.39 (m, 5H), 2.27 (s, 3H), 2.07 (s, 3H), 1.97 (s, 3H) ppm.<br>Mpt 183.1-183.2° C. |
| A13 | 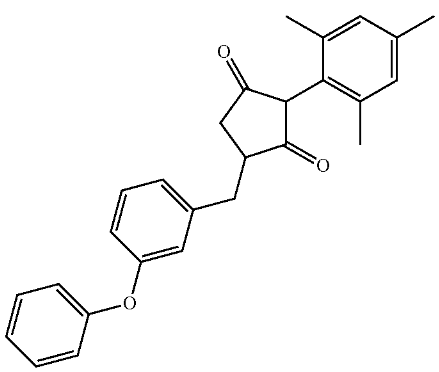 [SMILES: Cc1cc(C)c(C2C(=O)CC(Cc3cccc(Oc4ccccc4)c3)C2=O)c(C)c1] | δ 7.34 (t, 2H), 7.28-7.23 (m, 1H), 7.11 (t, 1H), 7.04-6.95 (m, 3H), 6.94-6.84 (m, 4H), 6.29 (bs, 1H), 3.36-2.86 (m, 5H), 2.28 (s, 3H), 2.08 (s, 3H), 1.98-1.96 (m, 3H) ppm.<br>Mpt: 192.0-194.8° C. |
| A14 | 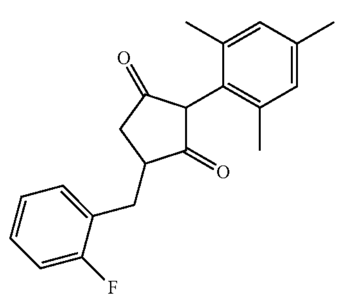 [SMILES: Cc1cc(C)c(C2C(=O)CC(Cc3ccccc3F)C2=O)c(C)c1] | δ 7.22-7.17 (m, 2H), 7.03-6.93 (m, 2H), 6.92-6.86 (m, 2H), 6.50 (bs, 1H), 3.85-2.82 (m, 5H), 2.28 (s, 3H), 2.08 (s, 3H), 1.92 (s, 3H) ppm.<br>Mpt 197.8-210.2° C. |

TABLE A1-continued

Compounds A1 to A47

| Compound Number | Structure | LC/MS, NMR or other physical data |
| --- | --- | --- |
| A15 | 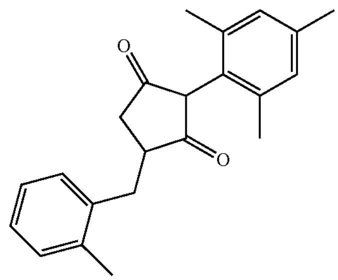 [SMILES: Cc1cc(C)c(C2C(=O)CC(Cc3ccccc3C)C2=O)c(C)c1] | δ 7.23-7.10 (m, 4H), 6.92 (s, 2H), 6.58-6.34 (bm, 1H), 3.45-2.42 (m, 5H), 2.38 (s, 3H), 2.28 (s, 3H), 2.13-2.03 (m, 6H) ppm.<br>Mpt 210-215.5° C. |
| A16 | 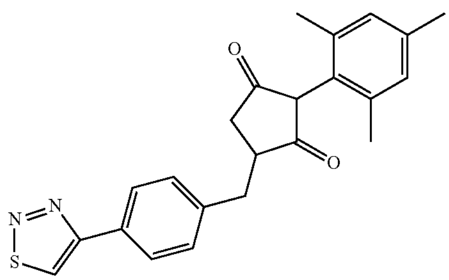 [SMILES: Cc1cc(C)c(C2C(=O)CC(Cc3ccc(-c4csnn4)cc3)C2=O)c(C)c1] | δ 8.65-8.59 (m, 1H), 8.03-7.95 (m, 2H), 7.43-7.36 (m, 2H), 6.95-9.87 (m, 2H), 6.36-6.20 (m, 1H), 3.46-2.32 (m, 5H), 2.28 (s, 3H), 2.11-2.07 (m, 3H), 1.97-1.94 (m, 3H) ppm.<br>Mpt 225-232° C. |
| A17 | 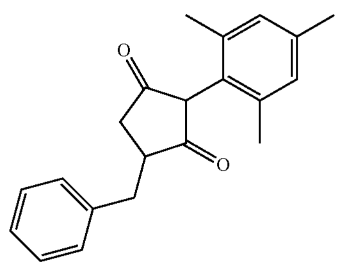 [SMILES: Cc1cc(C)c(C2C(=O)CC(Cc3ccccc3)C2=O)c(C)c1] | δ 7.34-7.19 (m, 5H), 6.93-6.86 (m, 2H), 6.49 (bs, 1H), 3.37-2.37 (m, 5H), 2.27 (s, 3H), 2.08 (s, 3H), 1.93 (s, 3H) ppm.<br>Mpt 160-165° C. |
| A18 | 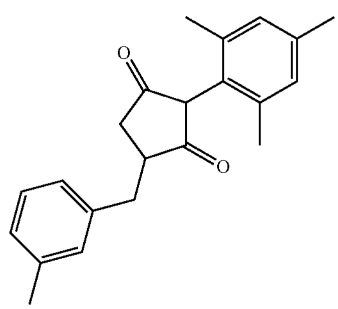 [SMILES: Cc1cccc(CC2CC(=O)C(c3c(C)cc(C)cc3C)C2=O)c1] | δ 7.18 (t, 1H), 7.10-6.99 (m, 3H), 6.94-6.86 (m, 2H), 6.86-6.6 (bs, 1H), 3.25-2.38 (m, 5H), 2.32 (s, 3H), 2.26 (s, 3H), 2.06 (s, 3H), 1.94 (s, 3H) ppm.<br>Mpt 173-179° C. |
| A19 | 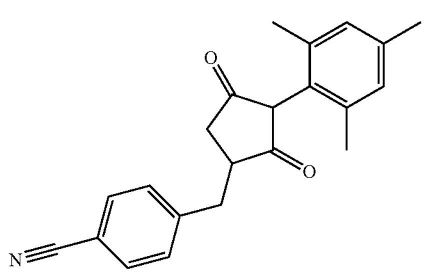 [SMILES: Cc1cc(C)c(C2C(=O)CC(Cc3ccc(C#N)cc3)C2=O)c(C)c1] | δ 7.59 (d, 2H), 7.36 (d, 2H), 6.92-6.89 (m, 2H), 6.79-6.66 (bs, 1H), 3.40-2.31 (m, 5H), 2.27 (s, 3H), 2.07 (s, 3H), 1.91 (s, 3H) ppm.<br>Mpt 249-251° C. |

TABLE A1-continued

Compounds A1 to A47

| Compound Number | Structure | LC/MS, NMR or other physical data |
|---|---|---|
| A20 | 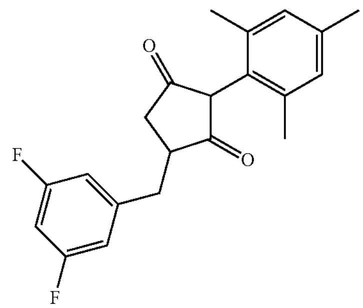 [SMILES: Cc1cc(C)c(C2C(=O)CC(Cc3cc(F)cc(F)c3)C2=O)c(C)c1] | δ 6.93-6.83 (m, 2H), 6.81-6.72 (m, 2H), 6.71-6.61 (m, 2H), 3.41-2.31 (m, 5H), 2.27 (s, 3H), 2.07 (s, 3H), 1.95 (s, 3H) ppm.<br>MPt 193.0-193.2° C. |
| A21 | 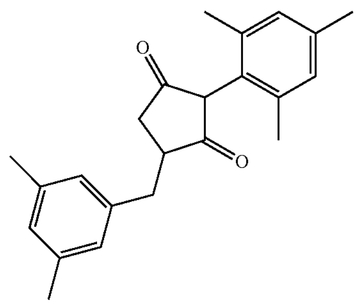 | δ 6.94-6.82 (m, 5H), 6.27 (bs, 1H), 3.35-2.89 (m, 5H), 2.31-2.25 (m, 9H), 2.10-2.07 (m, 3H), 2.00-1.98 (m, 3H) ppm.<br>MPt 181-184° C. |
| A22 | 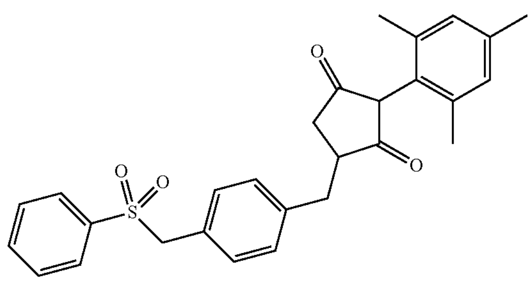 [SMILES: Cc1cc(C)c(C2C(=O)CC(Cc3ccc(CS(=O)(=O)c4ccccc4)cc3)C2=O)c(C)c1] | δ 7.80-7.58 (m, 3H), 7.56-7.42 (m, 2H), 7.37-7.13 (m, 4H), 7.08-6.75 (m, 3H), 4.48 (s, 2H), 3.35-2.34 (m, 5H), 2.27 (s, 3H), 2.07 (s, 3H), 2.02-1.93 (m, 3H) ppm.<br>MPt 189.0-191.7° C. |
| A23 | 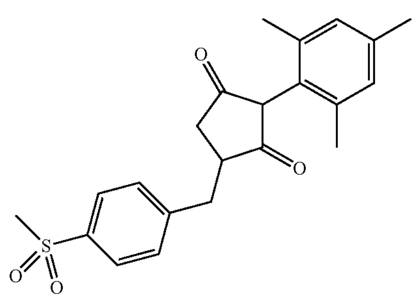 | δ 7.93-7.86 (m, 2H), 7.46 (d, 2H), 6.91 (d, 2H), 6.61-6.49 (m, 1H), 3.41-2.31 (m, 8H), 2.28 (s, 3H), 2.08 (s, 3H), 1.94-1.89 (m, 3H) ppm<br>MPt 235.3-238.6° C. |
| A24 | 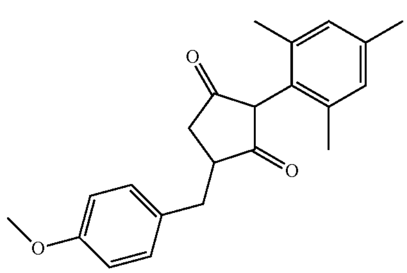 | δ 7.14 (d, 2H), 6.91-6.87 (m, 2H), 6.83 (d, 2H), 6.79-6.67 (bs, 1H), 3.79 (s, 3H), 3.21-2.38 (m, 5H), 2.27 (s, 3H), 2.07 (s, 3H), 1.93 (s, 3H) ppm.<br>MPt 197.3-197.6° C. |

TABLE A1-continued

Compounds A1 to A47

| Compound Number | Structure | LC/MS, NMR or other physical data |
|---|---|---|
| A25 | 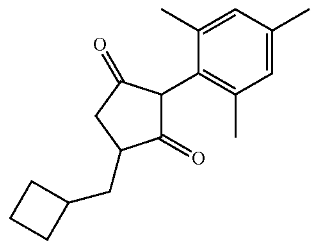 [SMILES: Cc1cc(C)c(C2C(=O)CC(CC3CCC3)C2=O)c(C)c1] | LC/MS (Method A) ES+: MH+ = 285 rt = 1.60 min |
| A26 | 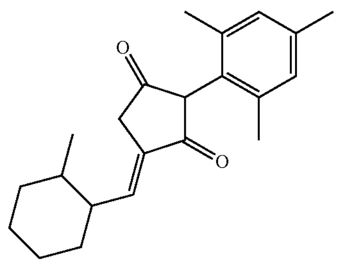 [SMILES: Cc1cc(C)c(C2C(=O)C/C(=C\C3CCCCC3C)C2=O)c(C)c1] | LC/MS (Method A) ES+: MH+ = 325 rt = 1.80 min |
| A27 | 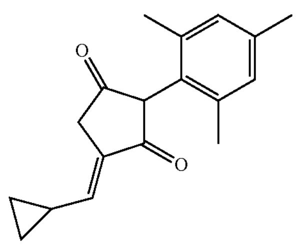 [SMILES: Cc1cc(C)c(C2C(=O)C/C(=C\C3CC3)C2=O)c(C)c1] | LC/MS (Method A) ES+: MH+ = 269 rt = 1.44 min |
| A28 | 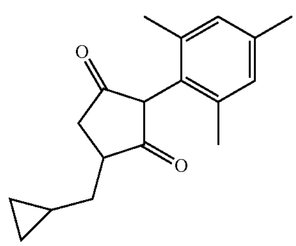 [SMILES: Cc1cc(C)c(C2C(=O)CC(CC3CC3)C2=O)c(C)c1] | LC/MS (Method A) ES+: MH+ = 271 rt = 1.53 min |
| A29 | 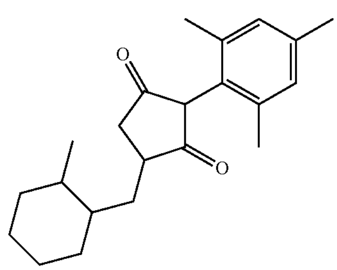 [SMILES: Cc1cc(C)c(C2C(=O)CC(CC3CCCCC3C)C2=O)c(C)c1] | LC/MS (Method D) ES+: MH+ = 327 rt = 1.12 min |
| A30 | 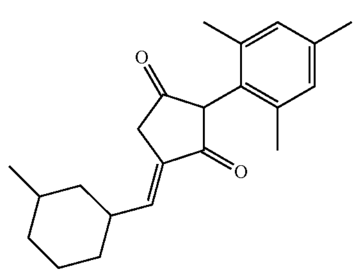 | LC/MS (Method A) ES+: MH+ = 325 rt = 1.81 min |

TABLE A1-continued

Compounds A1 to A47

| Compound Number | Structure | LC/MS, NMR or other physical data |
|---|---|---|
| A31 | 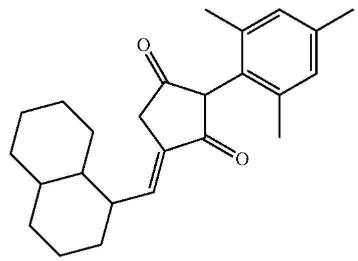 | LC/MS (Method A) ES+: MH+ = 365 rt = 2.03 min |
| A32 | 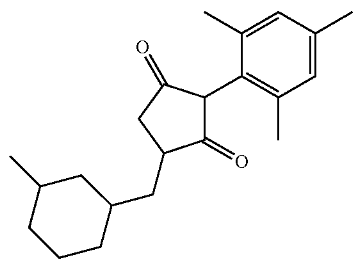 | LC/MS (Method A) ES+: MH+ = 327 rt = 1.80 min |
| A33 | 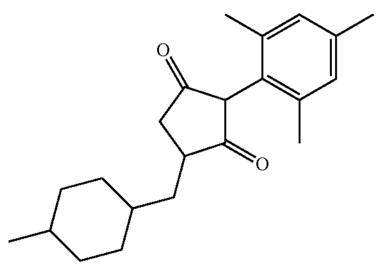 | LC/MS (Method A) ES+: MH+ = 327 rt = 1.85 min |
| A34 | 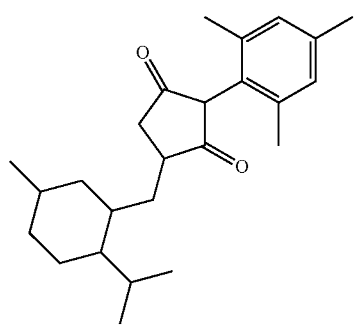 | LC/MS (Method A) ES+: MH+ = 369 rt = 2.06 min |
| A35 | 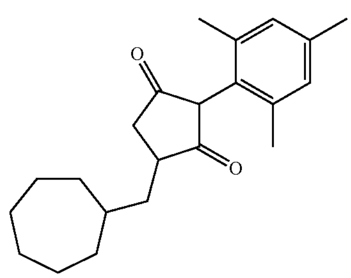 [SMILES: Cc1cc(C)c(C2C(=O)CC(CC3CCCCCC3)C2=O)c(C)c1] | LC/MS (Method A) ES+: MH+ = 327 rt = 1.83 min |

TABLE A1-continued
Compounds A1 to A47
| Compound Number | Structure | LC/MS, NMR or other physical data |
|---|---|---|
| A36 | 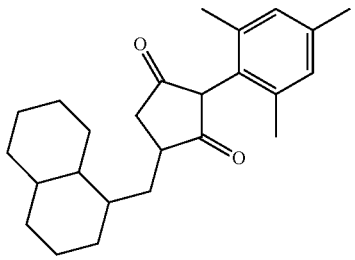 [SMILES: Cc1cc(C)c(C2C(=O)CC(CC3CCCC4CCCCC43)C2=O)c(C)c1] | LC/MS (Method A) ES+: MH+ = 367<br>rt = 2.02 min |
| A37 | 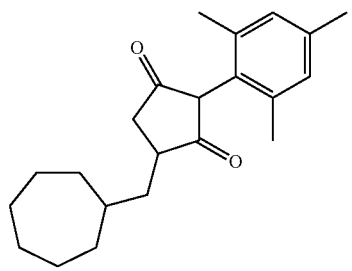 [SMILES: Cc1cc(C)c(C2C(=O)CC(CC3CCCCCC3)C2=O)c(C)c1] | LC/MS (Method A) ES+: MH+ = 325<br>rt = 1.84 min |
| A38 | 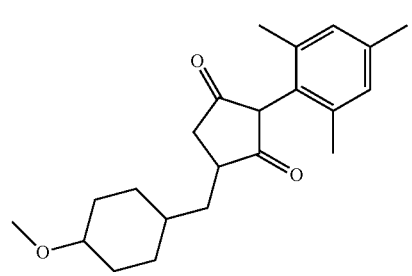 | LC/MS (Method A) ES+: MH+ = 343<br>rt = 1.41 min |
| A39 | 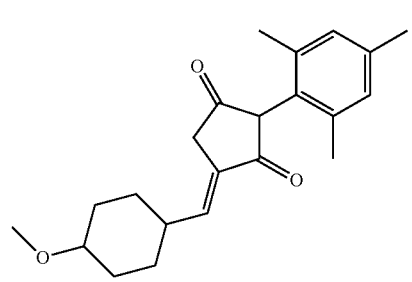 | LC/MS (Method A) ES+: MH+ = 341<br>rt = 1.54 min |
| A40 | 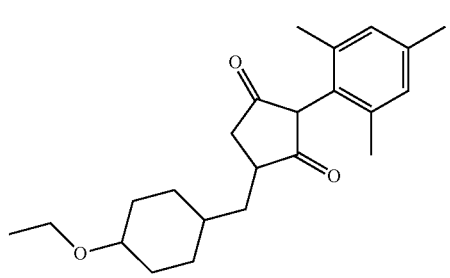 [SMILES: CCOC1CCC(CC2CC(=O)C(c3c(C)cc(C)cc3C)C2=O)CC1] | |

TABLE A1-continued
Compounds A1 to A47
| Compound Number | Structure | LC/MS, NMR or other physical data |
|---|---|---|
| A41 | 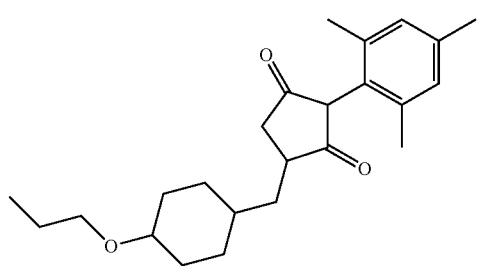 [SMILES: CCCOC1CCC(CC2CC(=O)C(c3c(C)cc(C)cc3C)C2=O)CC1] | |
| A42 | 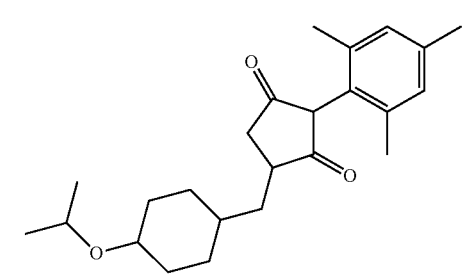 [SMILES: Cc1cc(C)c(C2C(=O)CC(CC3CCC(OC(C)C)CC3)C2=O)c(C)c1] | |
| A43 | 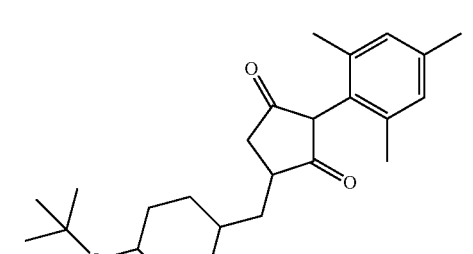 | |
| A44 | 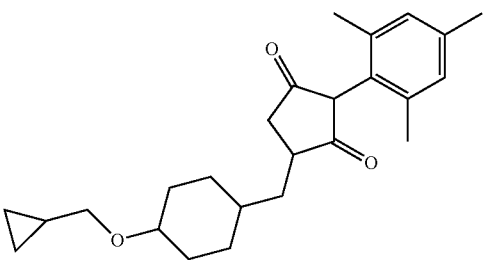 [SMILES: Cc1cc(C)c(C2C(=O)CC(CC3CCC(OCC4CC4)CC3)C2=O)c(C)c1] | |
| A45 | 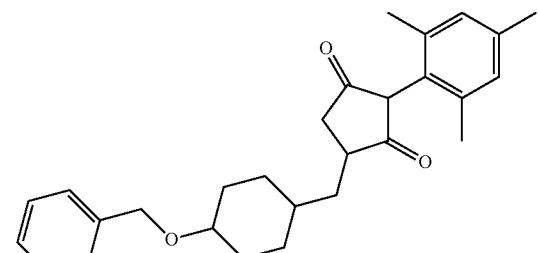 | |

TABLE A1-continued

Compounds A1 to A47

| Compound Number | Structure | LC/MS, NMR or other physical data |
|---|---|---|
| A46 | 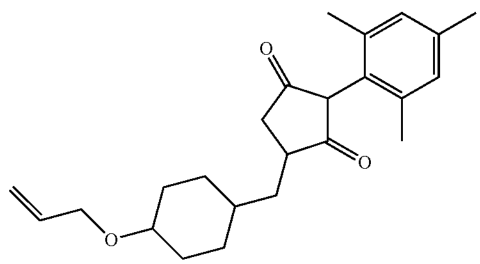 [SMILES: C=CCOC1CCC(CC2CC(=O)C(c3c(C)cc(C)cc3C)C2=O)CC1] | |
| A47 | 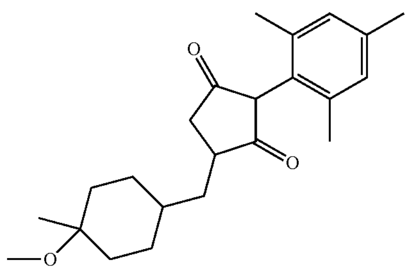 | |

TABLE B1

Compounds B1 to B28

| Compound Number | Structure | LC/MS, NMR or other physical data |
|---|---|---|
| B1 | 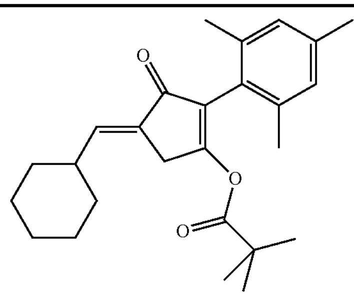 | LC/MS (Method A) ES$^+$: MH$^+$ = 395 rt = 2.23 min |
| B2 | 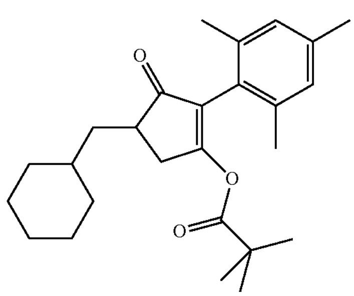 [SMILES: Cc1cc(C)c(C2=C(OC(=O)C(C)(C)C)CC(CC3CCCCC3)C2=O)c(C)c1] | LC/MS (Method A) ES$^+$: MH$^+$ = 397 rt = 2.29 min |

TABLE B1-continued

Compounds B1 to B28

| Compound Number | Structure | LC/MS, NMR or other physical data |
|---|---|---|
| B3 | 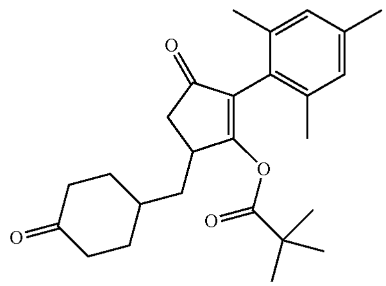 [SMILES: Cc1cc(C)c(C2=C(OC(=O)C(C)(C)C)C(CC3CCC(=O)CC3)CC2=O)c(C)c1] | LC/MS (Method A) ES⁺: MH⁺ = 411 rt = 1.81 |
| B4 | 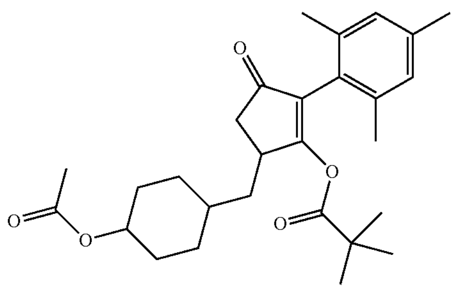 [SMILES: CC(=O)OC1CCC(CC2CC(=O)C(c3c(C)cc(C)cc3C)=C2OC(=O)C(C)(C)C)CC1] | LC/MS (Method A) ES⁺: M − H⁺ = 453 rt = 1.46 |
| B5 | 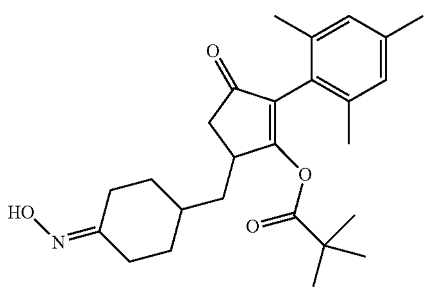 [SMILES: Cc1cc(C)c(C2=C(OC(=O)C(C)(C)C)C(CC3CCC(=NO)CC3)CC2=O)c(C)c1] | LC/MS (Method A) ES⁺: MH⁺ = 426 rt = 1.59 |
| B6 | 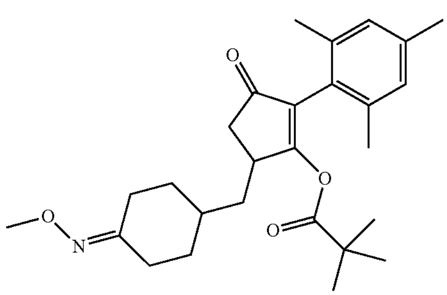 | LC/MS (Method A) ES⁺: MH⁺ = 440 rt = 1.98 |
| B7 | 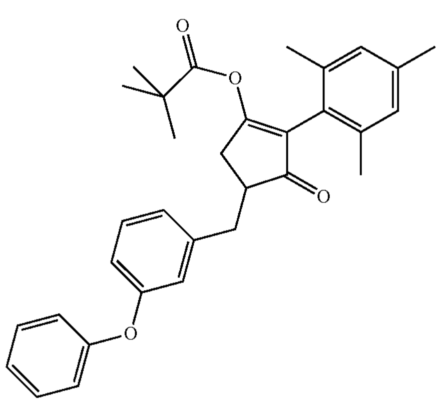 [SMILES: Cc1cc(C)c(C2=C(OC(=O)C(C)(C)C)CC(Cc3cccc(Oc4ccccc4)c3)C2=O)c(C)c1] | δ 7.37-7.30 (m, 2H), 7.28-7.23 (m, 1H), 7.11 (t, 1H), 7.03-6.96 (m, 3H), 6.92 (s, 1H), 6.89-6.81 (m, 3H), 3.35-3.26 (m, 1H), 3.24-3.09 (m, 2H), 2.79-2.68 (m, 2H), 2.25 (s, 3H), 2.06 (s, 3H), 1.98 (s, 3H), 1.06 (s, 9H) ppm. LC-MS (Method B) ES⁺: MH⁺ = 483, rt = 2.22 min |

TABLE B1-continued

Compounds B1 to B28

| Compound Number | Structure | LC/MS, NMR or other physical data |
|---|---|---|
| B8 | 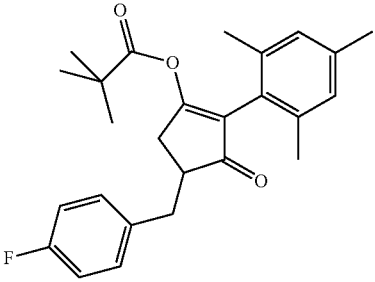 [SMILES: Cc1cc(C)c(C2=C(OC(=O)C(C)(C)C)CC(Cc3ccc(F)cc3)C2=O)c(C)c1] | δ 7.29-7.17 (m, 2H), 7.11-7.01 (m, 2H), 6.83 (s, 2H), 3.38 (dd, 1H), 3.16-3.08 (m, 1H), 3.01 (dd, 1H), 2.87-2.72 (m, 2H), 2.25 (s, 3H), 2.06 (s, 3H), 1.98 (s, 3H), 1.06 (s, 9H) ppm. LC-MS (Method B) ES$^+$: MH$^+$ = 409, rt = 2.03 min. |
| B9 | 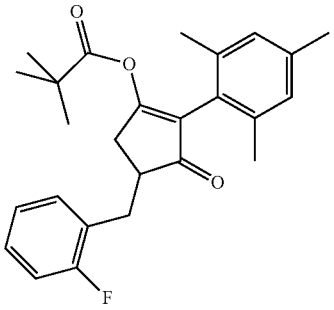 [SMILES: Cc1cc(C)c(C2=C(OC(=O)C(C)(C)C)CC(Cc3ccccc3F)C2=O)c(C)c1] | δ 7.23-7.17 (m, 2H), 7.02-6.95 (m, 2H), 6.86-6.81 (m, 2H), 3.26 (dd, 1H), 3.09-2.92 (m, 2H), 2.87-2.67 (m, 2H), 2.25 (s, 3H), 2.07 (s, 3H), 1.93 (s, 3H), 1.05 (s, 9H) ppm. LC-MS (Method B) ES$^+$: MH$^+$ = 409, rt = 2.01 min. |
| B10 | 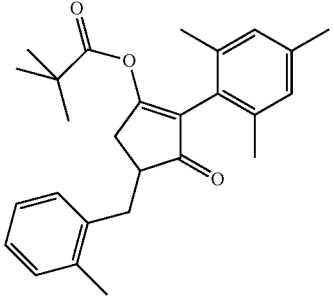 [SMILES: Cc1cc(C)c(C2=C(OC(=O)C(C)(C)C)CC(Cc3ccccc3C)C2=O)c(C)c1] | δ 7.22-7.13 (m, 4H), 6.85 (s, 2H), 3.42 (dd, 1H), 3.12-3.05 (m, 1H), 3.03-2.94 (m, 1H), 2.77-2.60 (m, 2H), 2.38 (s, 3H), 2.26 (s, 3H), 2.09-2.06 (m, 6H), 1.06 (s, 9H) ppm. LC-MS (Method B) ES$^+$: MH$^+$ = 405, rt = 2.09 min. |
| B11 | 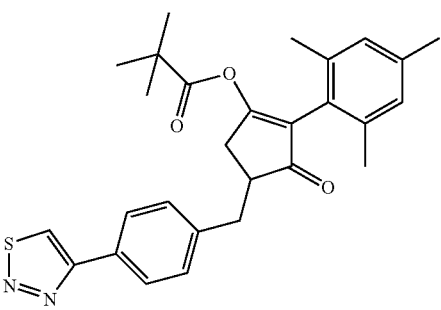 [SMILES: Cc1cc(C)c(C2=C(OC(=O)C(C)(C)C)CC(Cc3ccc(-c4csnn4)cc3)C2=O)c(C)c1] | LC/MS (Method B) ES$^+$: MH$^+$ = 475, rt = 1.99 min. |
| B12 | 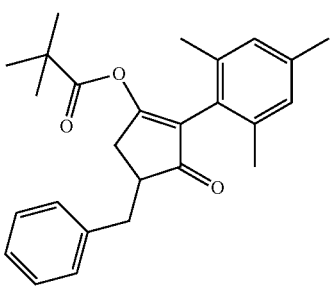 [SMILES: Cc1cc(C)c(C2=C(OC(=O)C(C)(C)C)CC(Cc3ccccc3)C2=O)c(C)c1] | LC/MS (Method B) ES$^+$: MH$^+$ = 391, rt = 2.02 min. |

TABLE B1-continued

Compounds B1 to B28

| Compound Number | Structure | LC/MS, NMR or other physical data |
|---|---|---|
| B13 | 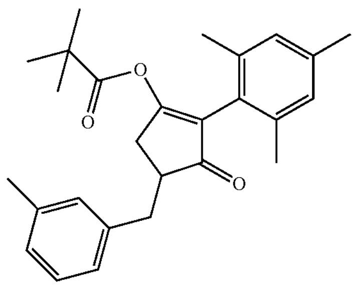 | LC/MS (Method B) ES+: MH+ = 405, rt = 2.10 min. |
| B14 | 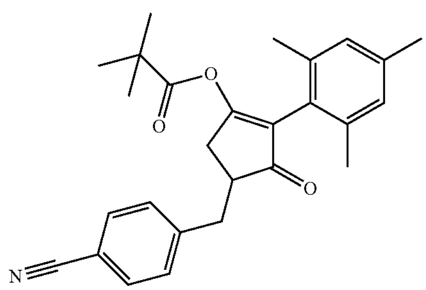 [SMILES: Cc1cc(C)c(C2=C(OC(=O)C(C)(C)C)CC(Cc3ccc(C#N)cc3)C2=O)c(C)c1] | LC/MS (Method B) ES+: MH+ = 416, rt = 1.91 min. |
| B15 | 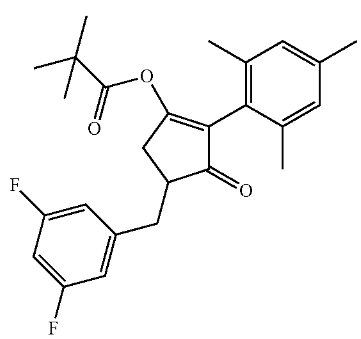 [SMILES: Cc1cc(C)c(C2=C(OC(=O)C(C)(C)C)CC(Cc3cc(F)cc(F)c3)C2=O)c(C)c1] | LC/MS (Method B) ES+: MH+ = 427, rt = 2.04 min. |
| B16 | 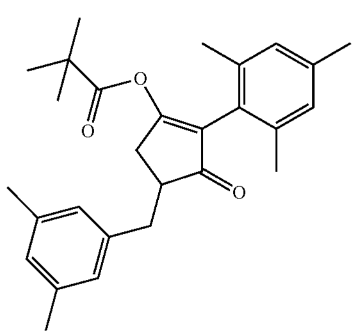 | LC/MS (Method B) ES+: MH+ = 419, rt = 2.19 min. |

TABLE B1-continued
Compounds B1 to B28
| Compound Number | Structure | LC/MS, NMR or other physical data |
|---|---|---|
| B17 | 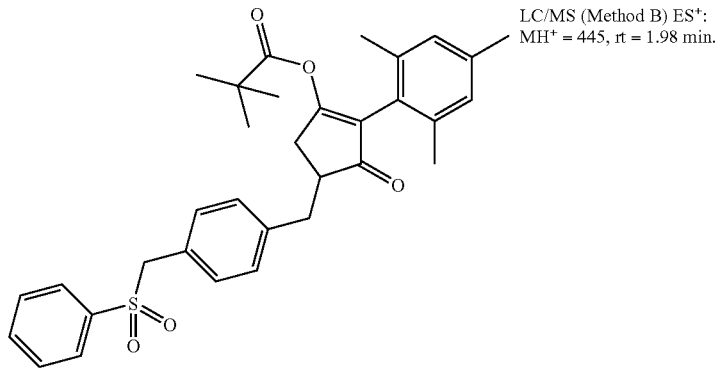 | LC/MS (Method B) ES$^+$: MH$^+$ = 445, rt = 1.98 min. |
| B18 | 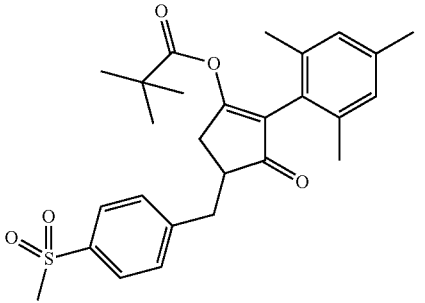 [SMILES: Cc1cc(C)c(C2=C(OC(=O)C(C)(C)C)CC(Cc3ccc(S(C)(=O)=O)cc3)C2=O)c(C)c1] | LC/MS (Method B) ES$^+$: MH$^+$ = 469, rt = 1.75 min. |
| B19 | 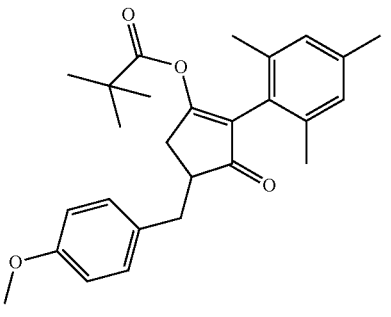 | LC/MS (Method B) ES$^+$: MH$^+$ = 421, rt = 1.99 min. |
| B20 | 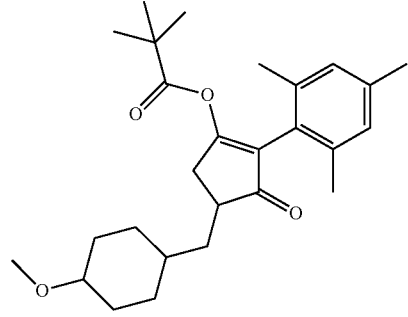 | |

TABLE B1-continued
Compounds B1 to B28
| Compound Number | Structure | LC/MS, NMR or other physical data |
|---|---|---|
| B21 | 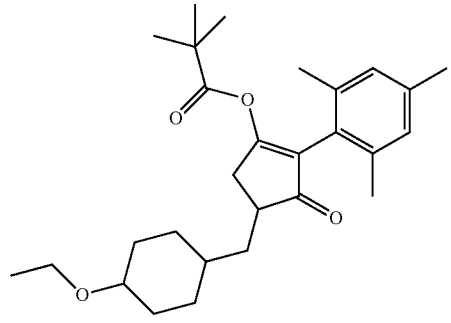 [SMILES: CCOC1CCC(CC2CC(OC(=O)C(C)(C)C)=C(c3c(C)cc(C)cc3C)C2=O)CC1] | |
| B22 | 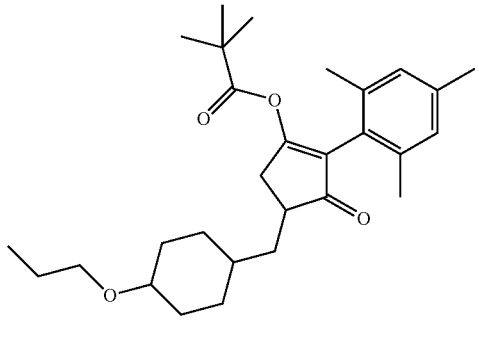 [SMILES: CCCOC1CCC(CC2CC(OC(=O)C(C)(C)C)=C(c3c(C)cc(C)cc3C)C2=O)CC1] | |
| B23 | 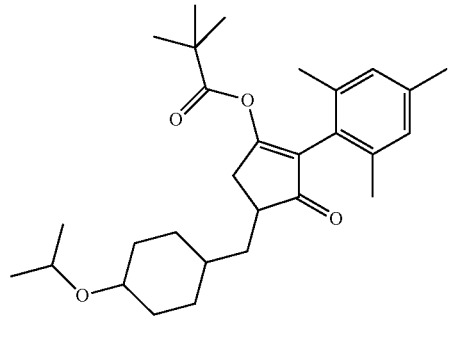 [SMILES: Cc1cc(C)c(C2=C(OC(=O)C(C)(C)C)CC(CC3CCC(OC(C)C)CC3)C2=O)c(C)c1] | |
| B24 | 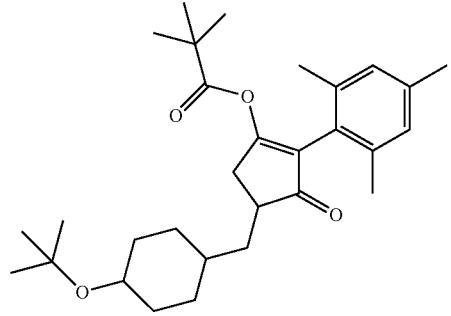 [SMILES: Cc1cc(C)c(C2=C(OC(=O)C(C)(C)C)CC(CC3CCC(OC(C)(C)C)CC3)C2=O)c(C)c1] | |

TABLE B1-continued
Compounds B1 to B28
| Compound Number | Structure | LC/MS, NMR or other physical data |
|---|---|---|
| B25 | 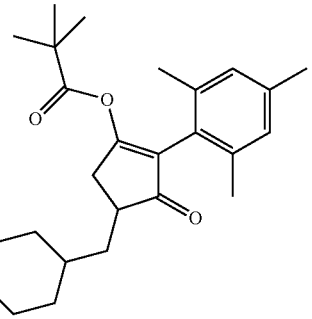 | |
| B26 | 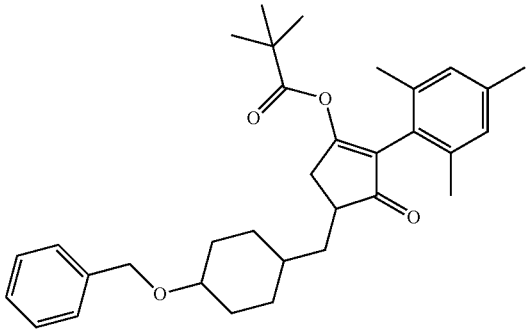 [SMILES: Cc1cc(C)c(C2=C(OC(=O)C(C)(C)C)CC(CC3CCC(OCc4ccccc4)CC3)C2=O)c(C)c1] | |
| B27 | 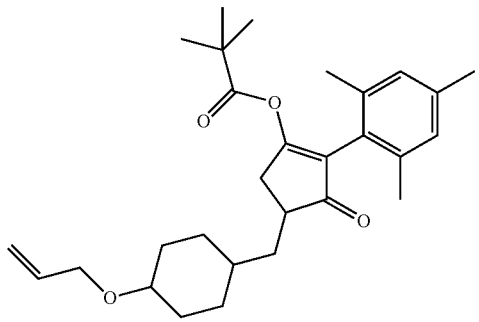 [SMILES: C=CCOC1CCC(CC2CC(OC(=O)C(C)(C)C)=C(c3c(C)cc(C)cc3C)C2=O)CC1] | |
| B28 | 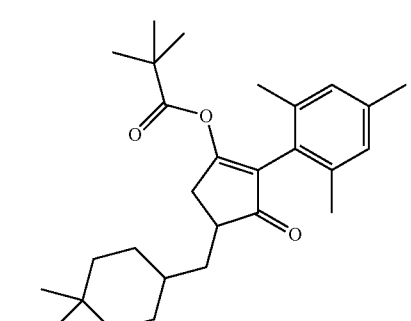 | |

103

Table C1: Compounds C1 to C10

The following 2-(2,6-diethyl-4-methylphenyl)-cyclopentane-1,3-diones, containing a benzyl or substituted benzyl side-chain on the cyclopentanedione (i.e. wherein A=optionally substituted phenyl according to formula (I)), were synthesised in general by substantially the following synthetic route and conditions:

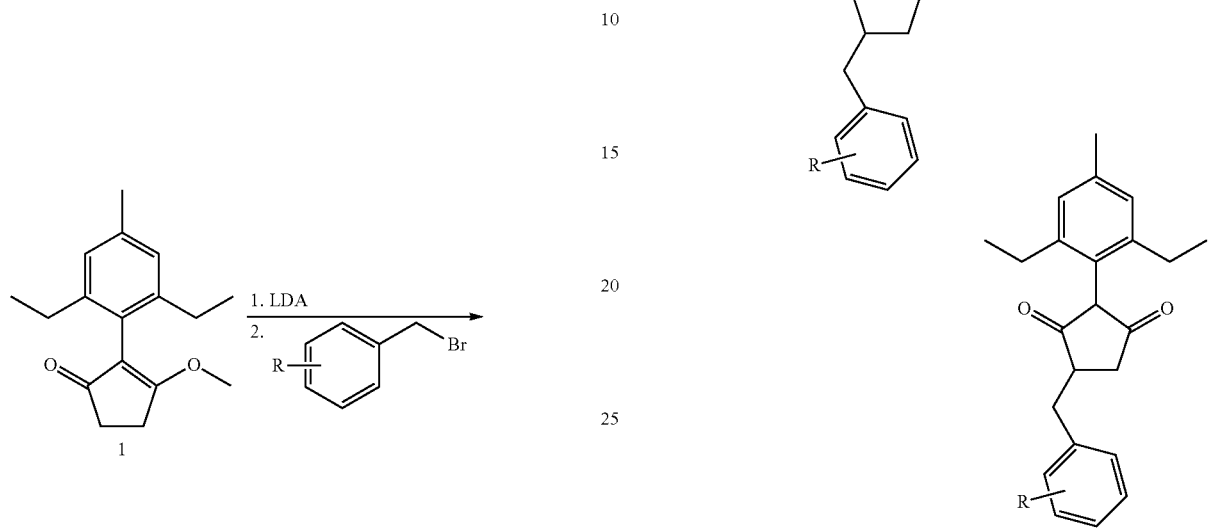

Compound 1 in the above scheme is known from WO2009/19005 (see Example 2, step 2, page 55-56, therein). LDA=lithium diisopropylamide.

| Compound number | Structure | Data |
|---|---|---|
| C1 | 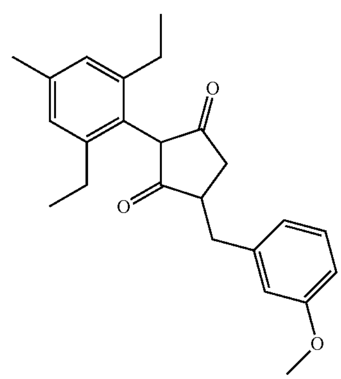 [SMILES: CCc1cc(C)cc(CC)c1C1C(=O)CC(Cc2cccc(OC)c2)C1=O] | LC/MS (Method A) ES+:<br>MH+ = 365<br>rt = 1.68 |
| C2 | 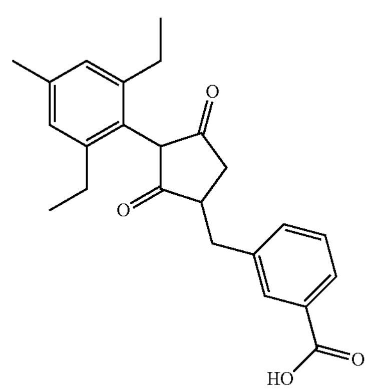 [SMILES: CCc1cc(C)cc(CC)c1C1C(=O)CC(Cc2cccc(C(=O)O)c2)C1=O] | LC/MS (Method A) ES+:<br>MH+ = 379<br>rt = 1.49 min |

| Compound number | Structure | Data |
|---|---|---|
| C3 | 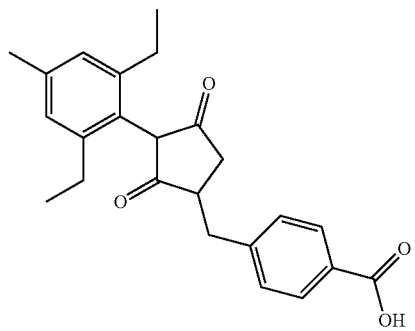 [SMILES: CCc1cc(C)cc(CC)c1C1C(=O)CC(Cc2ccc(C(=O)O)cc2)C1=O] | LC/MS (Method A) ES+:<br>MH+ = 379<br>rt = 1.50 min |
| C4 | 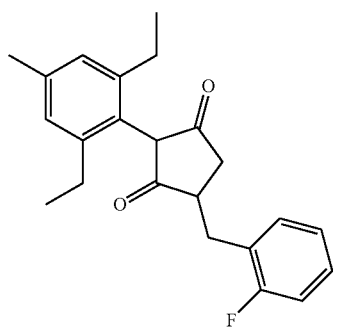 [SMILES: CCc1cc(C)cc(CC)c1C1C(=O)CC(Cc2ccccc2F)C1=O] | LC/MS (Method A) ES+:<br>MH+ = 353<br>rt = 1.72 min |
| C5 | 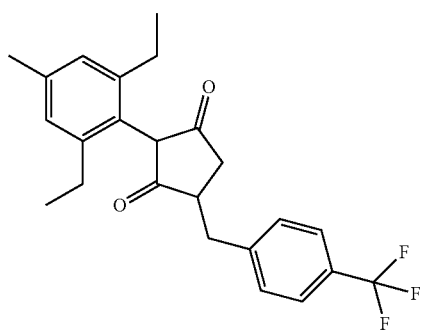 [SMILES: CCc1cc(C)cc(CC)c1C1C(=O)CC(Cc2ccc(C(F)(F)F)cc2)C1=O] | LC/MS (Method A) ES+:<br>MH+ = 403<br>rt = 1.82 min |
| C6 | 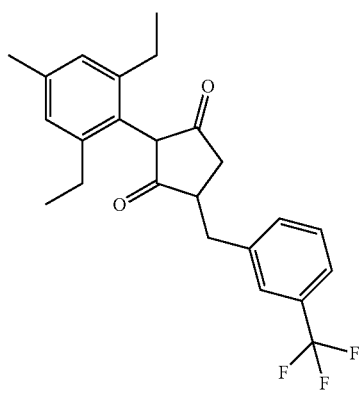 [SMILES: CCc1cc(C)cc(CC)c1C1C(=O)CC(Cc2cccc(C(F)(F)F)c2)C1=O] | LC/MS (Method A) ES+:<br>MH+ = 403<br>rt = 1.80 min |

-continued
| Compound number | Structure | Data |
|---|---|---|
| C7 | 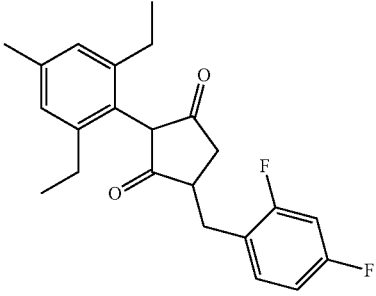 [SMILES: CCc1cc(C)cc(CC)c1C1C(=O)CC(Cc2ccc(F)cc2F)C1=O] | LC/MS (Method A) ES+:<br>MH+ = 371<br>rt = 1.73 min |
| C8 | 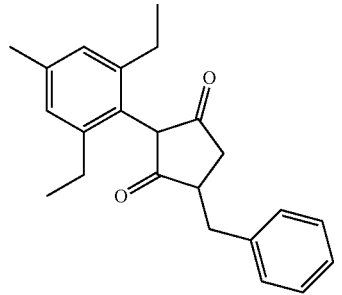 [SMILES: CCc1cc(C)cc(CC)c1C1C(=O)CC(Cc2ccccc2)C1=O] | LC/MS (Method A) ES+:<br>MH+ = 335<br>rt = 1.70 min |
| C9 | 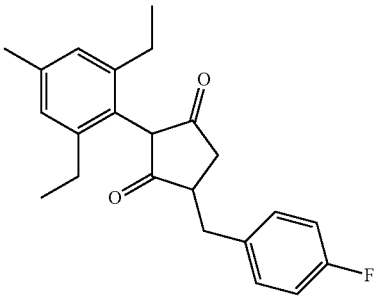 [SMILES: CCc1cc(C)cc(CC)c1C1C(=O)CC(Cc2ccc(F)cc2)C1=O] | LC/MS (Method A) ES+:<br>MH+ = 353<br>rt = 1.70 min |
| C10 | 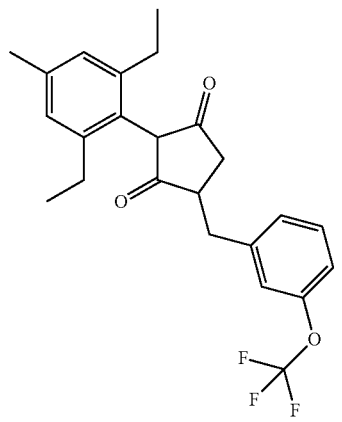 [SMILES: CCc1cc(C)cc(CC)c1C1C(=O)CC(Cc2cccc(OC(F)(F)F)c2)C1=O] | LC/MS (Method A) ES+:<br>MH+ = 419<br>rt = 1.85 min |

The compounds of the following Tables 1 to 21 can be obtained in an analogous manner.

Table 1 covers 82 compounds of the following type:

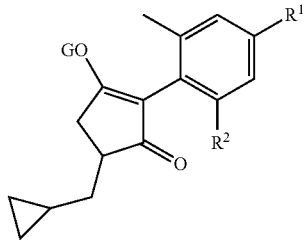

where G is hydrogen, and R$^1$ and R$^2$ are as described in Table 1 below:

| Compound Number | R$^1$ | R$^2$ |
|---|---|---|
| 1.001 | H | CH$_3$ |
| 1.002 | CH$_3$ | CH$_3$ |
| 1.003 | CH$_2$CH$_3$ | CH$_3$ |
| 1.004 | F | CH$_3$ |
| 1.005 | Cl | CH$_3$ |
| 1.006 | Br | CH$_3$ |
| 1.007 | CH$_3$O | CH$_3$ |
| 1.008 | CH$_3$CH$_2$O | CH$_3$ |
| 1.009 | —CH=CH$_2$ | CH$_3$ |
| 1.010 | —CCH | CH$_3$ |
| 1.011 | phenyl | CH$_3$ |
| 1.012 | 2-fluorophenyl | CH$_3$ |
| 1.013 | 2-chlorophenyl | CH$_3$ |
| 1.014 | 2-trifluoromethylphenyl | CH$_3$ |
| 1.015 | 2-nitrophenyl | CH$_3$ |
| 1.016 | 2-methylphenyl | CH$_3$ |
| 1.017 | 2-methanesulfonylphenyl | CH$_3$ |
| 1.018 | 2-cyanophenyl | CH$_3$ |
| 1.019 | 3-fluorophenyl | CH$_3$ |
| 1.020 | 3-chlorophenyl | CH$_3$ |
| 1.021 | 3-trifluoromethylphenyl | CH$_3$ |
| 1.022 | 3-nitrophenyl | CH$_3$ |
| 1.023 | 3-methylphenyl | CH$_3$ |
| 1.024 | 3-methanesulfonylphenyl | CH$_3$ |
| 1.025 | 3-cyanophenyl | CH$_3$ |
| 1.026 | 4-fluorophenyl | CH$_3$ |
| 1.027 | 4-chlorophenyl | CH$_3$ |
| 1.028 | 4-bromophenyl | CH$_3$ |
| 1.029 | 4-difluoromethoxyphenyl | CH$_3$ |
| 1.030 | 2-fluoro-4-chlorophenyl | CH$_3$ |
| 1.031 | 3-fluoro-4-chlorophenyl | CH$_3$ |
| 1.032 | 2-chloro-4-chlorophenyl | CH$_3$ |
| 1.033 | 2-chloro-4-fluorophenyl | CH$_3$ |
| 1.034 | 3-chloro-4-chlorophenyl | CH$_3$ |
| 1.035 | 3-chloro-4-fluorophenyl | CH$_3$ |
| 1.036 | 2-methyl-4-chlorophenyl | CH$_3$ |
| 1.037 | 4-trifluoromethylphenyl | CH$_3$ |
| 1.038 | 4-nitrophenyl | CH$_3$ |
| 1.039 | 4-methylphenyl | CH$_3$ |
| 1.040 | 4-methanesulfonylphenyl | CH$_3$ |
| 1.041 | 4-cyanophenyl | CH$_3$ |
| 1.042 | H | CH$_3$O |
| 1.043 | CH$_3$ | CH$_3$O |
| 1.044 | CH$_2$CH$_3$ | CH$_3$O |
| 1.045 | F | CH$_3$O |
| 1.046 | Cl | CH$_3$O |
| 1.047 | Br | CH$_3$O |
| 1.048 | CH$_3$O | CH$_3$O |
| 1.049 | CH$_3$CH$_2$O | CH$_3$O |
| 1.050 | —CH=CH$_2$ | CH$_3$O |
| 1.051 | —CCH | CH$_3$O |
| 1.052 | phenyl | CH$_3$O |
| 1.053 | 2-fluorophenyl | CH$_3$O |
| 1.054 | 2-chlorophenyl | CH$_3$O |
| 1.055 | 2-trifluoromethylphenyl | CH$_3$O |
| 1.056 | 2-nitrophenyl | CH$_3$O |
| 1.057 | 2-methylphenyl | CH$_3$O |
| 1.058 | 2-methanesulfonylphenyl | CH$_3$O |
| 1.059 | 2-cyanophenyl | CH$_3$O |
| 1.060 | 3-fluorophenyl | CH$_3$O |
| 1.061 | 3-chlorophenyl | CH$_3$O |
| 1.062 | 3-trifluoromethylphenyl | CH$_3$O |
| 1.063 | 3-nitrophenyl | CH$_3$O |
| 1.064 | 3-methylphenyl | CH$_3$O |
| 1.065 | 3-methanesulfonylphenyl | CH$_3$O |
| 1.066 | 3-cyanophenyl | CH$_3$O |
| 1.067 | 4-fluorophenyl | CH$_3$O |
| 1.068 | 4-chlorophenyl | CH$_3$O |
| 1.069 | 4-bromophenyl | CH$_3$O |
| 1.070 | 4-difluoromethoxyphenyl | CH$_3$O |
| 1.071 | 2-fluoro-4-chlorophenyl | CH$_3$O |
| 1.072 | 3-fluoro-4-chlorophenyl | CH$_3$O |
| 1.073 | 2-chloro-4-chlorophenyl | CH$_3$O |
| 1.074 | 2-chloro-4-fluorophenyl | CH$_3$O |
| 1.075 | 3-chloro-4-chlorophenyl | CH$_3$O |
| 1.076 | 3-chloro-4-fluorophenyl | CH$_3$O |
| 1.077 | 2-methyl-4-chlorophenyl | CH$_3$O |
| 1.078 | 4-trifluoromethylphenyl | CH$_3$O |
| 1.079 | 4-nitrophenyl | CH$_3$O |
| 1.080 | 4-methylphenyl | CH$_3$O |
| 1.081 | 4-methanesulfonylphenyl | CH$_3$O |
| 1.082 | 4-cyanophenyl | CH$_3$O |

Table 2 covers 82 compounds of the following type where G is hydrogen and R$^1$ and R$^2$ are as described in Table 1.

Table 3 covers 82 compounds of the following type where G is hydrogen and R$^1$ and R$^2$ are as described in Table 1.

Table 4 covers 82 compounds of the following type

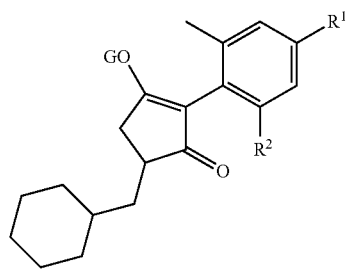

where G is hydrogen and R¹ and R² are as described in Table 1.

Table 5 covers 82 compounds of the following type

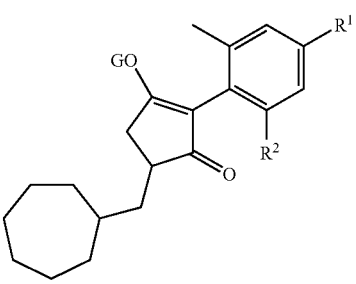

where G is hydrogen and R¹ and R² are as described in Table 1.

Table 6a covers 82 compounds of the following type

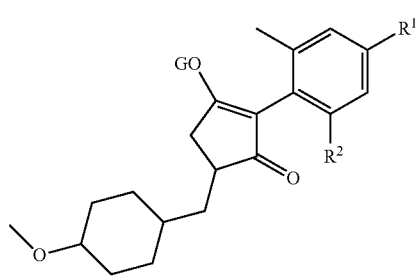

where G is hydrogen and R¹ and R² are as described in Table 1.

Table 6b covers 82 compounds of the following type

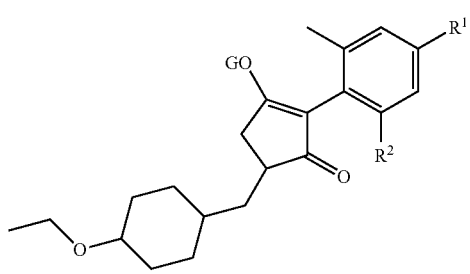

where G is hydrogen and R¹ and R² are as described in Table 1.

Table 6c covers 82 compounds of the following type

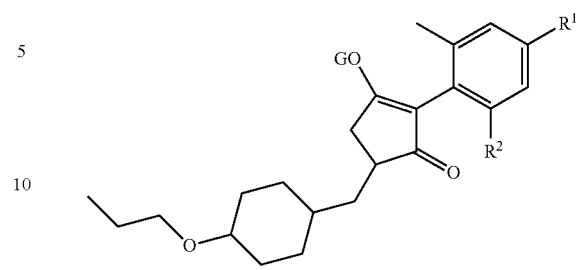

where G is hydrogen and R¹ and R² are as described in Table 1.

Table 6d covers 82 compounds of the following type

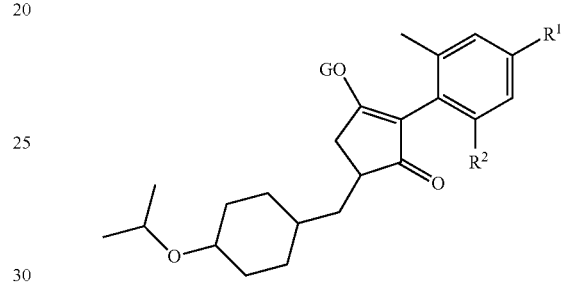

where G is hydrogen and R¹ and R² are as described in Table 1.

Table 6e covers 82 compounds of the following type

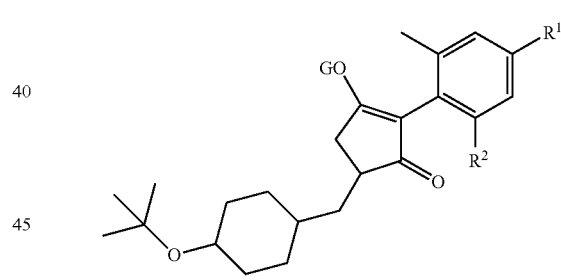

where G is hydrogen and R¹ and R² are as described in Table 1.

Table 6f covers 82 compounds of the following type

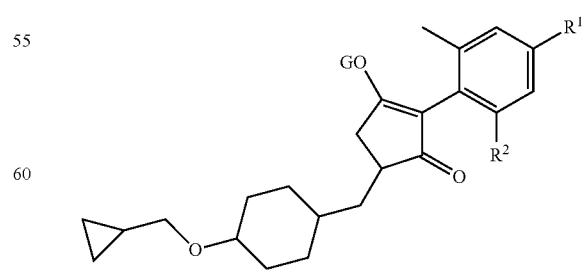

where G is hydrogen and R¹ and R² are as described in Table 1.

Table 6g covers 82 compounds of the following type

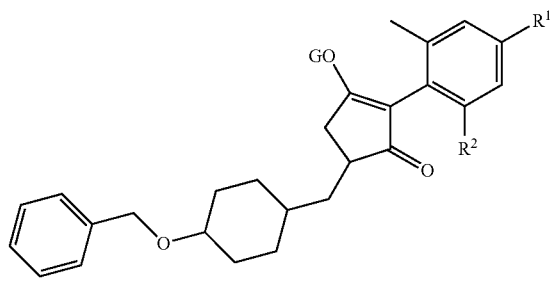

where G is hydrogen and $R^1$ and $R^2$ are as described in Table 1.

Table 6h covers 82 compounds of the following type

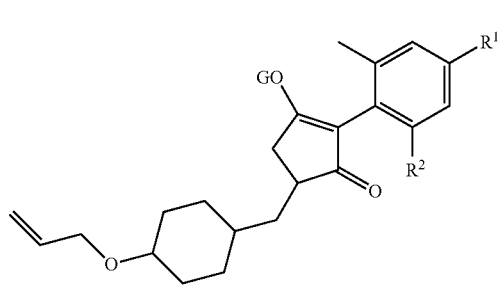

where G is hydrogen and $R^1$ and $R^2$ are as described in Table 1.

Table 6i covers 82 compounds of the following type

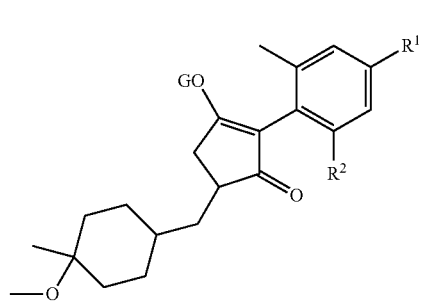

where G is hydrogen and $R^1$ and $R^2$ are as described in Table 1.

Table 7 covers 82 compounds of the following type

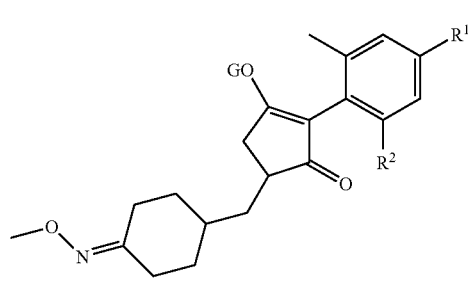

where G is hydrogen and $R^1$ and $R^2$ are as described in Table 1.

Table 8 covers 82 compounds of the following type

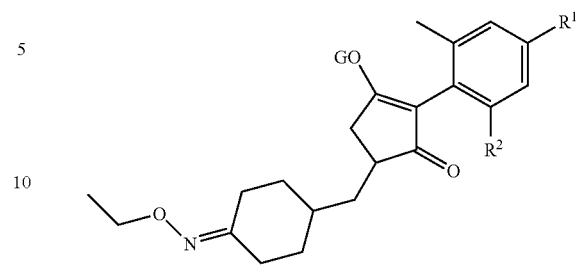

where G is hydrogen and $R^1$ and $R^2$ are as described in Table 1.

Table 9 covers 82 compounds of the following type

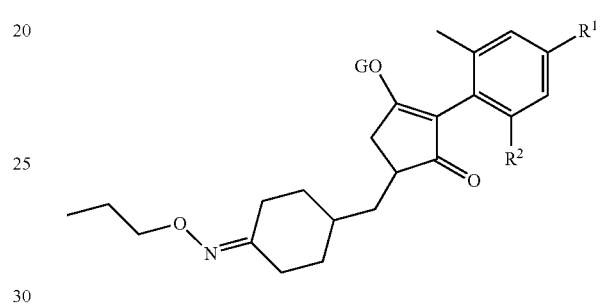

where G is hydrogen and $R^1$ and $R^2$ are as described in Table 1.

Table 10 covers 82 compounds of the following type

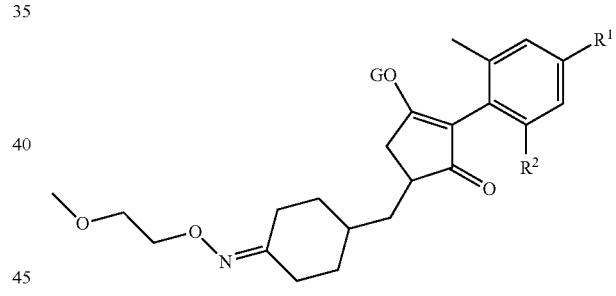

where G is hydrogen and $R^1$ and $R^2$ are as described in Table 1.

Table 11 covers 82 compounds of the following type

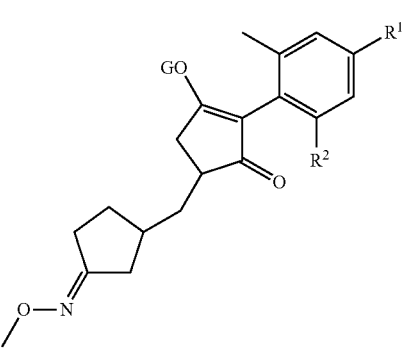

where G is hydrogen and $R^1$ and $R^2$ are as described in Table 1.

Table 12 covers 82 compounds of the following type

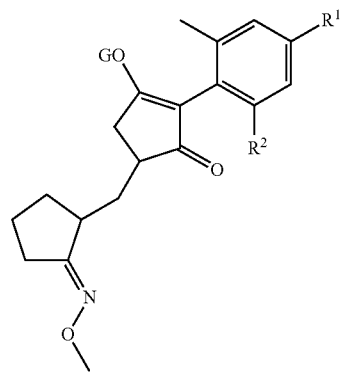

where G is hydrogen and $R^1$ and $R^2$ are as described in Table 1.

Table 13 covers 82 compounds of the following type

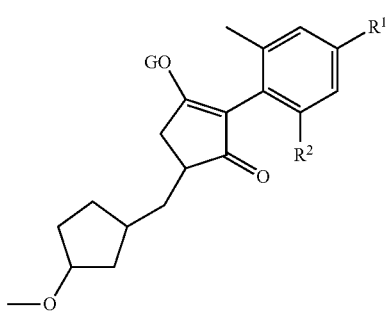

where G is hydrogen and $R^1$ and $R^2$ are as described in Table 1.

Table 14 covers 82 compounds of the following type

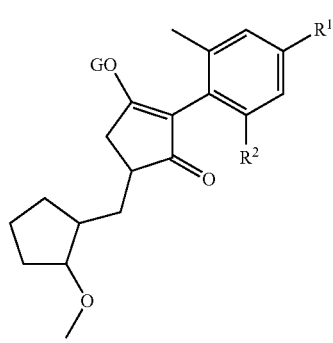

where G is hydrogen and $R^1$ and $R^2$ are as described in Table 1.

Table 15 covers 82 compounds of the following type

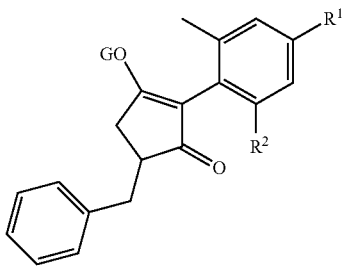

where G is hydrogen and $R^1$ and $R^2$ are as described in Table 1.

Table 16 covers 82 compounds of the following type

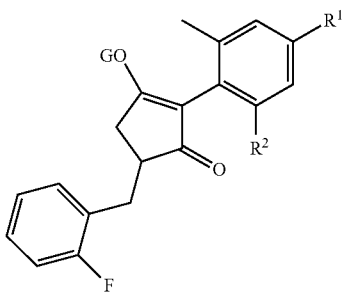

where G is hydrogen and $R^1$ and $R^2$ are as described in Table 1.

Table 17 covers 82 compounds of the following type

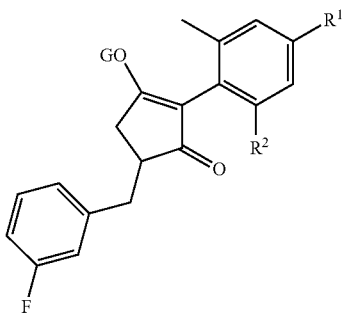

where G is hydrogen and $R^1$ and $R^2$ are as described in Table 1.

Table 18 covers 82 compounds of the following type

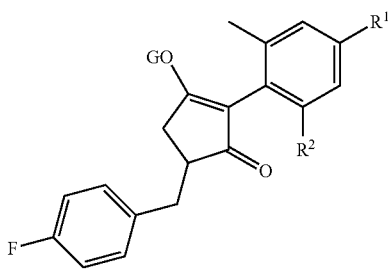

where G is hydrogen and $R^1$ and $R^2$ are as described in Table 1.

Table 19 covers 82 compounds of the following type

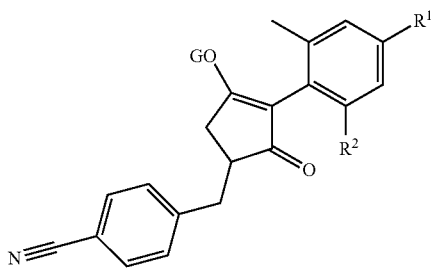

where G is hydrogen and $R^1$ and $R^2$ are as described in Table 1.

Table 20 covers 82 compounds of the following type

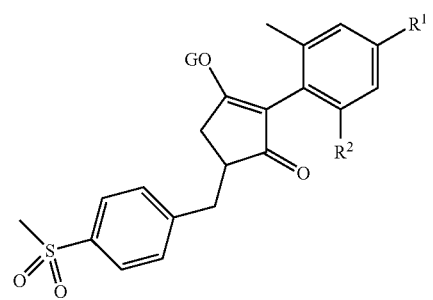

where G is hydrogen and $R^1$ and $R^2$ are as described in Table 1.

Table 21 covers 82 compounds of the following type

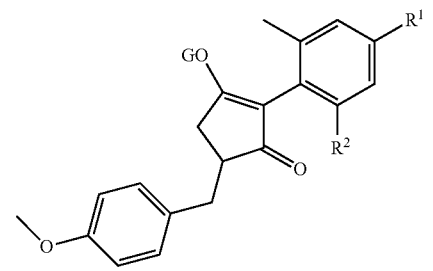

where G is hydrogen and $R^1$ and $R^2$ are as described in Table 1.

BIOLOGICAL EXAMPLES

Example A

Seeds of a variety of test species are sown in standard soil in pots. After cultivation for one day (pre-emergence) or after 8 days cultivation (post-emergence) under controlled conditions in a glasshouse (at 24/16° C., day/night; 14 hours light; 65% humidity), the plants are sprayed with an aqueous spray solution derived from the formulation of the technical active ingredient in acetone/water (50:50) solution containing 0.5% Tween 20 (polyoxyethelyene sorbitan monolaurate, CAS RN 9005-64-5).

The test plants are then grown in a glasshouse under controlled conditions in a glasshouse (at 24/16° C., day/night; 14 hours light; 65% humidity) and watered twice daily. After 13 days for pre and post-emergence, the test is evaluated (100=total damage to plant; 0=no damage to plant).

Test Plants:
*Lolium perenne* (LOLPE), *Alopecurus myosuroides* (ALOMY), *Echinochloa crus-galli* (ECHCG), *Avena fatua* (AVEFA)

Post-Emergence Activity

| Compound Number | Rate g/ha | LOLPE | ALOMY | ECHCG | AVEFA |
|---|---|---|---|---|---|
| A1 | 250 | 80 | 80 | 90 | 80 |
| A2 | 250 | 100 | 70 | 90 | 80 |
| A3 | 250 | 90 | 90 | 90 | 80 |
| A4 | 250 | 60 | 70 | 90 | 70 |
| A5 | 250 | 30 | 30 | 30 | 20 |
| A6 | 250 | 80 | 80 | 80 | 60 |
| A7 | 250 | 30 | 50 | 80 | 40 |
| A8 | 250 | 100 | 70 | 50 | 90 |
| A9 | 250 | 100 | 100 | 80 | 90 |
| A10 | 250 | 40 | 20 | 70 | 20 |
| A11 | 250 | 50 | 10 | 20 | 0 |
| A13 | 250 | 20 | 30 | 20 | 30 |
| A14 | 250 | 90 | 80 | 80 | 30 |
| A15 | 250 | 90 | 80 | 40 | 50 |
| A16 | 250 | 30 | 20 | 50 | 50 |
| A17 | 250 | 80 | 80 | 60 | 40 |
| A18 | 250 | 90 | 80 | 50 | 50 |
| A19 | 250 | 90 | 90 | 90 | 60 |
| A20 | 250 | 50 | 20 | 50 | 30 |
| A21 | 250 | 30 | 40 | 60 | 20 |
| A22 | 250 | 20 | 0 | 20 | 10 |
| A23 | 250 | 50 | 90 | 90 | 90 |
| A24 | 250 | 80 | 80 | 30 | 90 |
| A25 | 250 | 100 | 60 | 90 | 80 |
| A26 | 250 | 90 | 60 | 70 | 50 |
| A27 | 250 | 100 | 60 | 100 | 70 |
| A28 | 250 | 100 | 70 | 90 | 50 |
| A29 | 250 | 90 | 0 | 50 | 0 |
| A30 | 250 | 60 | 60 | 80 | 70 |
| A31 | 250 | 70 | 20 | 80 | 20 |
| A32 | 250 | 100 | 70 | 100 | 90 |
| A33 | 250 | 100 | 30 | 60 | 70 |
| A34 | 250 | 30 | 20 | 10 | 10 |
| A35 | 250 | 80 | 50 | 80 | 20 |
| A36 | 250 | 70 | 40 | 70 | 90 |
| A37 | 250 | 50 | 20 | 60 | 10 |
| A38 | 250 | 100 | 100 | 100 | 100 |
| A39 | 250 | 50 | 90 | 100 | 90 |
| B1 | 250 | 70 | 50 | 30 | 10 |
| B2 | 250 | 90 | 80 | 60 | 80 |
| B3 | 250 | 90 | 70 | 90 | 90 |
| B4 | 250 | 90 | 60 | 70 | 80 |
| B6 | 250 | 90 | 80 | 90 | 90 |
| B7 | 250 | 20 | 20 | 20 | 0 |
| B8 | 250 | 70 | 40 | 40 | 20 |
| B9 | 250 | 80 | 70 | 80 | 20 |
| B10 | 250 | 90 | 50 | 40 | 30 |
| B12 | 250 | 90 | 60 | 50 | 30 |
| B13 | 250 | 80 | 60 | 60 | 30 |
| B14 | 250 | 60 | 70 | 70 | 50 |
| B15 | 250 | 70 | 10 | 50 | 10 |
| B16 | 250 | 40 | 30 | 50 | 10 |
| B18 | 250 | 50 | 70 | 80 | 80 |
| B19 | 250 | 80 | 80 | 30 | 60 |

Pre-Emergence Activity

| Compound Number | Rate g/ha | LOLPE | ALOMY | ECHCG | AVEFA |
|---|---|---|---|---|---|
| A1 | 250 | 100 | 70 | 100 | 50 |
| A2 | 250 | 100 | 70 | 90 | 70 |
| A3 | 250 | 100 | 100 | 100 | 70 |
| A4 | 250 | 100 | 100 | 100 | 70 |
| A5 | 250 | 40 | 30 | 80 | 0 |

-continued

| Compound Number | Rate g/ha | LOLPE | ALOMY | ECHCG | AVEFA |
|---|---|---|---|---|---|
| A6 | 250 | 100 | 50 | 90 | 50 |
| A7 | 250 | 60 | 40 | 50 | 20 |
| A8 | 250 | 90 | 60 | 90 | 40 |
| A9 | 250 | 100 | 70 | 100 | 70 |
| A10 | 250 | 80 | 0 | 20 | 0 |
| A11 | 250 | 20 | 0 | 0 | 0 |
| A13 | 250 | 40 | 10 | 20 | 0 |
| A14 | 250 | 100 | 70 | 90 | 40 |
| A15 | 250 | 100 | 70 | 60 | 70 |
| A16 | 250 | 70 | 10 | 80 | 30 |
| A17 | 250 | 90 | 50 | 70 | 30 |
| A18 | 250 | 100 | 80 | 100 | 50 |
| A19 | 250 | 90 | 80 | 100 | 40 |
| A20 | 250 | 100 | 30 | 80 | 20 |
| A21 | 250 | 100 | 60 | 90 | 20 |
| A22 | 250 | 20 | 0 | 30 | 0 |
| A23 | 250 | 100 | 90 | 90 | 80 |
| A24 | 250 | 100 | 90 | 80 | 80 |
| A25 | 250 | 100 | 100 | 100 | 60 |
| A26 | 250 | 100 | 90 | 100 | 90 |
| A27 | 250 | 100 | 90 | 100 | 70 |
| A28 | 250 | 100 | 90 | 100 | 70 |
| A29 | 250 | 90 | 50 | 90 | 50 |
| A30 | 250 | 100 | 80 | 100 | 70 |
| A31 | 250 | 90 | 40 | 90 | 20 |
| A32 | 250 | 90 | 70 | 100 | 50 |
| A33 | 250 | 0 | 30 | 100 | 50 |
| A34 | 250 | 0 | 10 | 60 | 0 |
| A35 | 250 | 30 | 50 | 100 | 50 |
| A36 | 250 | 10 | 70 | 70 | 50 |
| A37 | 250 | 0 | 40 | 60 | 20 |
| A38 | 250 | 100 | 90 | 100 | 60 |
| A39 | 250 | 50 | 60 | 100 | 80 |
| B1 | 250 | 80 | 70 | 100 | 20 |
| B2 | 250 | 100 | 30 | 100 | 0 |
| B3 | 250 | 90 | 70 | 50 | 50 |
| B5 | 250 | 90 | 70 | 70 | 40 |
| B6 | 250 | 100 | 70 | 90 | 50 |
| B7 | 250 | 20 | 30 | 0 | 0 |
| B8 | 250 | 100 | 70 | 50 | 30 |
| B9 | 250 | 100 | 90 | 70 | 40 |
| B10 | 250 | 100 | 30 | 30 | 20 |
| B12 | 250 | 90 | 30 | 40 | 20 |
| B13 | 250 | 70 | 40 | 60 | 20 |
| B14 | 250 | 80 | 60 | 50 | 10 |
| B15 | 250 | 70 | 20 | 40 | 20 |
| B16 | 250 | 80 | 40 | 50 | 10 |
| B18 | 250 | 70 | 60 | 80 | 60 |
| B19 | 250 | 80 | 40 | 10 | 30 |

Example B

Seeds of the Winter Wheat variety 'Hereward' were sown in standard soil in pots. After 8 days cultivation under controlled conditions in a glasshouse (at 24/16° C., day/night; 14 hours light; 65% humidity), the plants were sprayed post-emergence with an aqueous spray solution derived from the formulation of the technical active ingredient in acetone/water (50:50) solution containing 0.5% Tween 20 (polyoxyethelyene sorbitan monolaurate, CAS RN 9005-64-5).

Seeds of the Winter Wheat variety 'Hereward' were seed treated with a wettable powder formulation of the cereal herbicide safener, cloquintocet mexyl, at a rate of 0.5 grams per kilogram of dry seed prior to the initiation of glasshouse testing. One seed was sown per 1.5 inch plastic pot into a sandy loam soil at a depth of 1 cm, 8 days prior to application of the test compounds and was watered and grown under controlled conditions in a glasshouse (at 24/16° C., day/night; 14 hours light; 65% humidity). The plants were sprayed post-emergence with an aqueous spray solution derived from the formulation of the technical active ingredient in acetone/water (50:50) solution containing 0.5% Tween 20 (polyoxyethelyene sorbitan monolaurate, CAS RN 9005-64-5).

The test plants were then grown in a glasshouse under controlled conditions in a glasshouse (at 24/16° C., day/night; 14 hours light; 65% humidity) and watered twice daily. After 13 days for pre and post-emergence, the test was evaluated (100=total damage to plant; 0=no damage to plant).

| Compound Number | Rate g/ha | Winter Wheat (Hereward) | Winter Wheat (Hereward) + cloquintocet mexyl |
|---|---|---|---|
| A1 | 250 | 60 | 50 |
| A2 | 250 | 70 | 10 |
| A3 | 250 | 60 | 20 |
| A4 | 250 | 60 | 0 |
| A5 | 250 | 10 | 0 |
| A6 | 250 | 10 | 0 |
| A7 | 250 | 20 | 0 |
| A8 | 250 | 30 | 10 |
| A9 | 250 | 30 | 40 |
| A10 | 250 | 10 | 0 |
| A11 | 250 | 0 | 0 |
| A14 | 250 | 30 | 20 |
| A15 | 250 | 30 | 20 |
| A17 | 250 | 10 | 10 |
| A18 | 250 | 20 | 10 |
| A19 | 250 | 60 | 10 |
| A20 | 250 | 10 | 0 |
| A21 | 250 | 20 | 20 |
| A23 | 250 | 50 | 50 |
| A24 | 250 | 40 | 10 |
| A25 | 250 | 30 | 0 |
| A26 | 250 | 40 | 20 |
| A27 | 250 | 40 | 0 |
| A28 | 250 | 30 | 10 |
| A30 | 250 | 50 | 0 |
| A31 | 250 | 20 | 0 |
| A32 | 250 | 30 | 0 |
| A33 | 250 | 40 | 0 |
| A34 | 250 | 20 | 10 |
| A35 | 250 | 20 | 0 |
| A36 | 250 | 20 | 0 |
| A38 | 250 | 70 | 50 |
| B1 | 250 | 10 | 0 |
| B2 | 250 | 70 | 0 |
| B3 | 250 | 40 | 30 |
| B5 | 250 | 40 | 10 |

The invention claimed is:

1. A compound of formula I

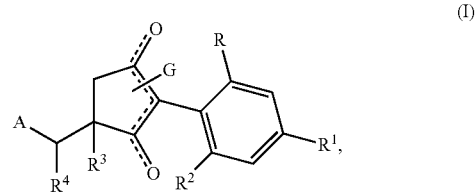

wherein

R is methyl, ethyl, vinyl, ethynyl or cyclopropyl, $R^1$ is $C_1$-$C_6$alkyl, $C_1$-$C_6$haloalkyl, $C_3$-$C_7$cycloalkyl, $C_1$-$C_6$alkoxy, $C_1$-$C_6$haloalkoxy, vinyl, propenyl, ethynyl, propynyl, halogen, phenyl, or phenyl substituted by $C_1$-$C_4$alkyl, $CF_3$, $CF_2Cl$, $CF_2H$, $CCl_2H$, $FCH_2$, $ClCH_2$, $BrCH_2$, $CH_3CHF$, $(CH_3)_2CF$, $CF_3CH_2$, $CHF_2CH_2$, $C_1$-$C_4$alkylsulfonyl, halogen, nitro or cyano, $R^2$ is methyl, ethyl, vinyl, ethynyl or methoxy, $R^3$ and $R^4$ are hydrogen or together form a double bond, and A is $C_3$-$C_7$cycloalkyl which is unsubstituted or substituted once or twice by $C_1$-$C_6$alkyl, $C_1$-$C_6$haloalkyl, $C_1$-$C_6$alkoxy, $C_1$-$C_6$alkylcarbonyloxy, $C_2$-$C_6$alkenyl, =O or =N—$R^{10}$, where $R^{10}$ is hydroxyl, $C_1$-$C_6$alkyl, $C_1$-$C_6$haloalkyl, $C_3$-$C_7$cycloalkyl, $C_1$-$C_6$alkoxy, $C_1$-$C_6$alkoxy$C_1$-$C_6$alkoxy or $C_1$-$C_6$haloalkoxy, or A is cyclohexyl substituted once, at the 4-position (calculated with respect to the cyclohexyl connection point), by one ($C_3$-$C_6$cycloalkyl)methoxy, $C_3$-$C_6$cycloalkyloxy, $C_2$-$C_5$alkenyl-$CH_2$-oxy, benzyloxy, (monomethyl- or dimethyl-phenyl)methoxy, (monomethoxy- or dimethoxy-phenyl)methoxy or (monofluoro- or difluoro-phenyl)methoxy substituent, or A is decahydro-1-naphthyl or decahydro-2-naphthyl, or A is optionally substituted phenyl, and G is hydrogen or an agriculturally acceptable metal, sulfonium, ammonium or a latentiating group;

wherein, when G is a latentiating group, the latentiating group G is selected from the groups $C_1$-$C_8$alkyl, $C_2$-$C_8$haloalkyl, phenyl$C_1$-$C_8$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro), heteroaryl$C_1$-$C_8$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$-$C_8$alkenyl, $C_3$-$C_8$haloalkenyl, $C_3$-$C_8$alkynyl, $C(X^a)$—$R^a$, $C(X^b)$—$X^c$—$R^b$, $C(X^d)$—$N(R^c)$—$R^d$, —$SO_2$—$R^e$, —$P(X^e)$($R^f$)—$R^g$ and $CH_2$—$X^f$—$R^h$;

wherein $X^a$, $X^b$, $X^c$, $X^d$, $X^e$ and $X^f$ are independently of each other oxygen or sulfur;

and wherein $R^a$ is H, $C_1$-$C_{18}$alkyl, $C_2$-$C_{18}$alkenyl, $C_2$-$C_{18}$alkynyl, $C_1$-$C_{10}$haloalkyl, $C_1$-$C_{10}$cyanoalkyl, $C_1$-$C_{10}$nitroalkyl, $C_1$-$C_{10}$ aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$-trialkylsilyl($C_1$-$C_5$)alkyl, phenyl($C_1$-$C_5$)alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl($C_1$-$C_5$)alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, or heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro;

$R^b$ is $C_1$-$C_{18}$alkyl, $C_3$-$C_{18}$alkenyl, $C_3$-$C_{18}$alkynyl, $C_2$-$C_{10}$haloalkyl, $C_1$-$C_{10}$ cyanoalkyl, $C_1$-$C_{10}$ nitroalkyl, $C_2$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$-trialkylsilyl($C_1$-$C_5$)alkyl, phenyl($C_1$-$C_5$)alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl($C_1$-$C_5$)alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkyl-thio, $C_1$-$C_3$alkylsulfinyl, $C_1$-$C_3$alkylsulfonyl, halogen, cyano, or by nitro), $C_3$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, or heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro; and $R^c$ and $R^d$ are each independently of each other hydrogen, $C_1$-$C_{10}$alkyl, $C_3$-$C_{10}$alkenyl, $C_3$-$C_{10}$alkynyl, $C_2$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_2$-$C_5$)alkylaminoalkyl, $C_3$-$C_8$-trialkylsilyl($C_1$-$C_5$)alkyl, phenyl($C_1$-$C_5$)alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl($C_1$-$C_5$)alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroarylamino or heteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro, diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro or $C_3$-$C_7$cycloalkylamino, di-$C_3$-$C_7$cycloalkylamino or $C_3$-$C_7$cycloalkoxy;

or $R^c$ and $R^d$ may join together to form a 3-7 membered ring, optionally containing one heteroatom selected from O or S; and $R^e$ is $C_1$-$C_{10}$alkyl, $C_2$-$C_{10}$alkenyl, $C_2$-$C_{10}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$-trialkylsilyl($C_1$-$C_5$)alkyl, phenyl($C_1$-$C_5$)alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl($C_1$-$C_5$)alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro, heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro, diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or $C_3$-$C_7$cycloalkylamino, di$C_3$-$C_7$cycloalkylamino, $C_3$-$C_7$cycloalkoxy, $C_1$-$C_{10}$alkoxy, $C_1$-$C_{10}$haloalkoxy, $C_1$-$C_5$alkylamino or $C_2$-$C_8$dialkylamino;

$R^f$ and $R^g$ are each independently of each other $C_1$-$C_{10}$alkyl, $C_2$-$C_{10}$alkenyl, $C_2$-$C_{10}$alkynyl, $C_1$-$C_{10}$alkoxy, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_2$-$C_5$)alkylaminoalkyl, $C_3$-$C_6$-trialkylsilyl($C_1$-$C_5$)alkyl, phenyl($C_1$-$C_5$)alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl($C_1$-$C_5$)alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or by nitro, heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro, diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or $C_3$-$C_7$cycloalkylamino, di$C_3$-$C_7$cycloalkylamino, $C_3$-$C_7$cycloalkoxy, $C_1$-$C_{10}$haloalkoxy, $C_1$-$C_5$alkylamino or $C_2$-$C_8$dialkylamino, or benzyloxy or phenoxy, wherein the benzyl and phenyl groups may in turn be substituted by $C_1$-$C_3$alkyl, $C_1$-$C_3$haloalkyl, $C_1$-$C_3$alkoxy, $C_1$-$C_3$haloalkoxy, halogen, cyano or nitro; and $R^h$ is $C_1$-$C_{10}$ alkyl, $C_3$-$C_{10}$ alkenyl, $C_3$-$C_{10}$ alkynyl, $C_1$-$C_{10}$ haloalkyl, $C_1$-$C_{10}$ cyanoalkyl, $C_1$-$C_{10}$ nitroalkyl, $C_2$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$-trialkylsilyl($C_1$-$C_5$)alkyl, phenyl($C_1$-$C_5$)alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryl($C_1$-$C_5$)alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), phenoxy($C_1$-$C_5$)alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryloxy($C_1$-$C_5$)alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen or by nitro, or heteroaryl, or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro;

and wherein, when A is optionally substituted phenyl, then, either:

(a) the compound of formula (I) is a compound of formula (IB):

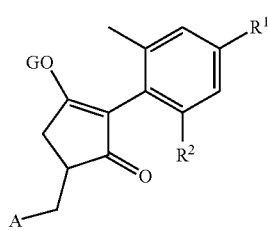

(IB)

wherein:

G is hydrogen;

$R^2$ is $CH_3$ or $CH_3O$;

$R^1$ is $CH_3$, $CH_2CH_3$, F, Cl, Br, $CH_3O$, $CH_3CH_2O$, —CH=$CH_2$, —CCH, phenyl, 2-fluorophenyl, 2-chlorophenyl, 2-trifluoromethylphenyl, 2-nitrophenyl, 2-methylphenyl, 2-methanesulfonylphenyl, 2-cyanophenyl, 3-fluorophenyl, 3-chlorophenyl, 3-trifluoromethylphenyl, 3-nitrophenyl, 3-methylphenyl, 3-methanesulfonylphenyl, 3-cyanophenyl, 4-fluorophenyl, 4-chlorophenyl, 4-bromophenyl, 4-difluoromethoxyphenyl, 2-fluoro-4-chlorophenyl, 3-fluoro-4-chlorophenyl, 2-chloro-4-chlorophenyl, 2-chloro-4-fluorophenyl, 3-chloro-4-chlorophenyl, 3-chloro-4-fluorophenyl, 2-methyl-4-chlorophenyl, 4-trifluoromethylphenyl, 4-nitrophenyl, 4-methylphenyl, 4-methanesulfonylphenyl, or 4-cyanophenyl; and A is of sub-formula (xv), (xvi), (xvii), (xviii), (xix), (xx) or (xxi):

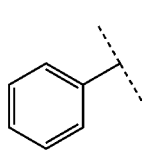

(xv)

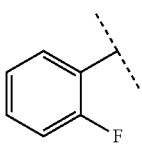

(xvi)

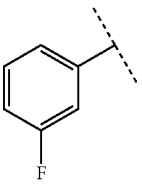

(xvii)

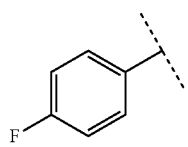

(xviii)

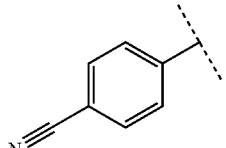

(xix)

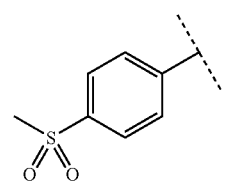

(xx)

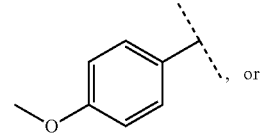

(xxi)

, or (b) the compound is one of the following compounds A13, A15, A16, A18, A20, A21, A22, B7, B8, B9, B10, B11, B12, B13, B14, B15, B16, B17, B18 or B19, or is one of the following compounds C1 to C10:

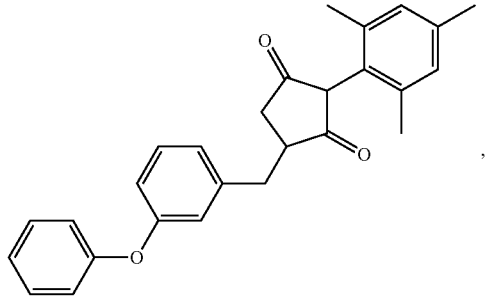

(A13)

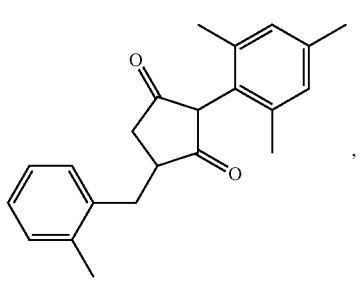

(A15)

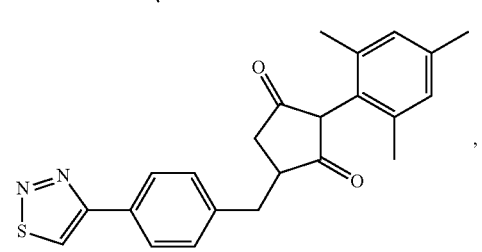

(A16)

-continued (A18), (A20), (A21), (A22), (B7), (B8), (B9), (B10), (B11), (B12), (B13)

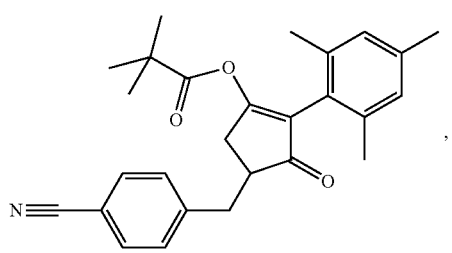
(B14)
,
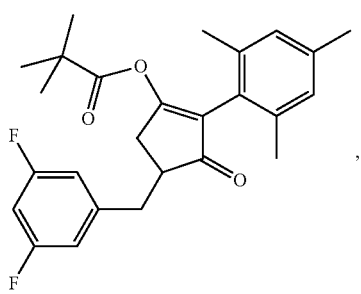
(B15)
,
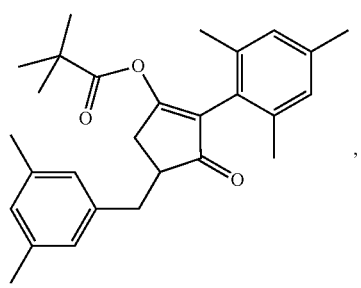
(B16)
,
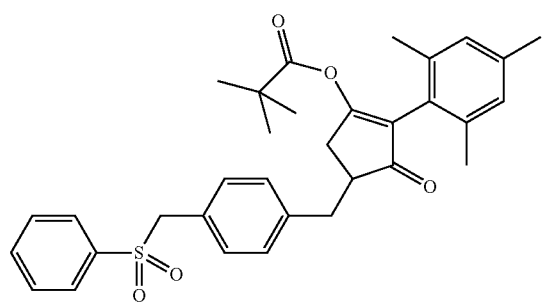
(B17)
,
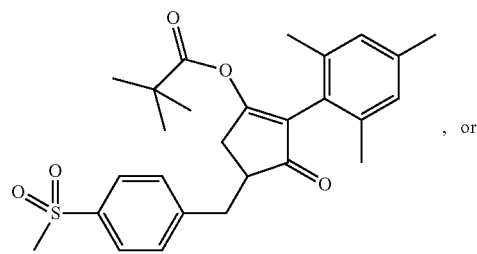
(B18) , or
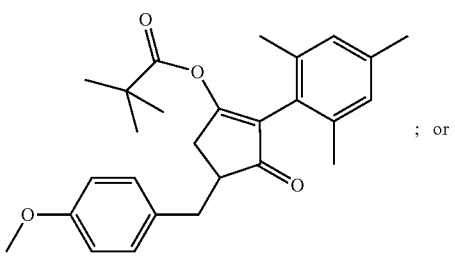
(B19) ; or
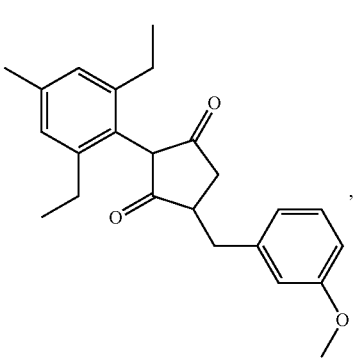
(C1)
,
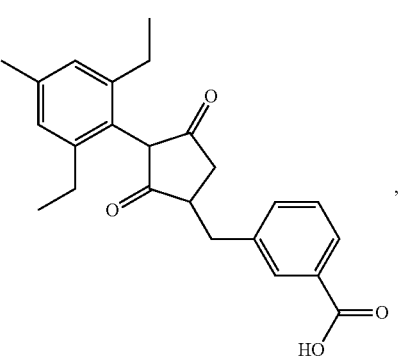
(C2)
,
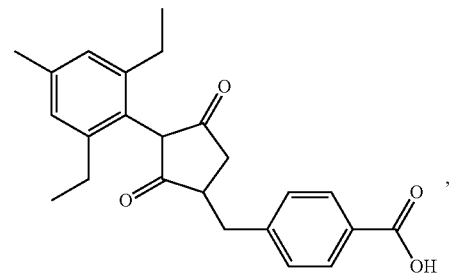
(C3)
,
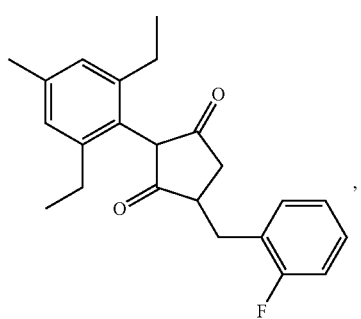
(C4)
, -continued (C5)
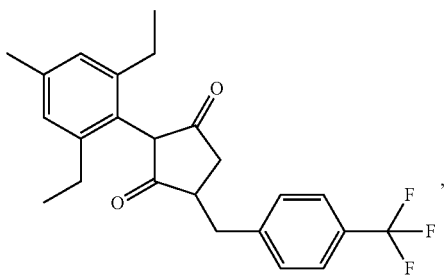

(C6)
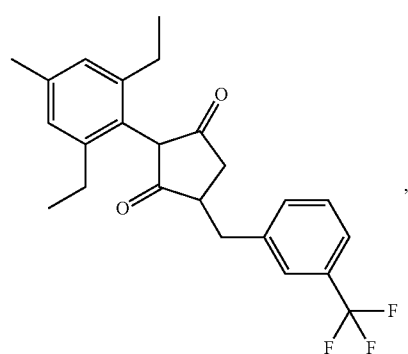

(C7)
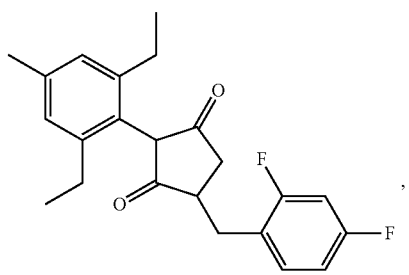

(C8)
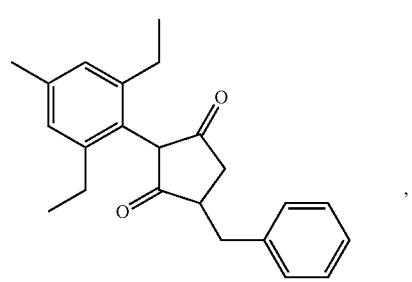

(C9)
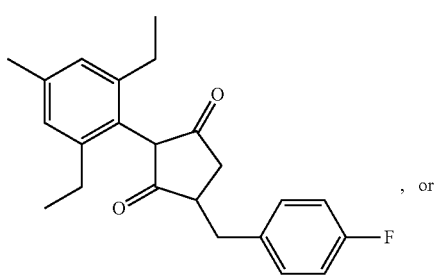, or

-continued (C10)
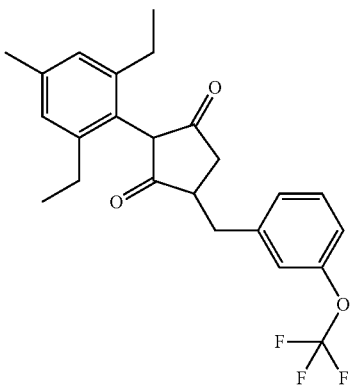

2. Compound according to claim 1, wherein
R is methyl, ethyl, vinyl, ethynyl or cyclopropyl,
$R^1$ is $C_1$-$C_6$alkyl, $C_1$-$C_6$haloalkyl, $C_3$-$C_7$cycloalkyl, $C_1$-$C_6$alkoxy, $C_1$-$C_6$haloalkoxy, vinyl, propenyl, ethynyl, propynyl, halogen, phenyl, or phenyl substituted by $C_1$-$C_4$alkyl, $CF_3$, $CF_2Cl$, $CF_2H$, $CCl_2H$, $FCH_2$, $ClCH_2$, $BrCH_2$, $CH_3CHF$, $(CH_3)_2CF$, $CF_3CH_2$, $CHF_2CH_2$, $C_1$-$C_4$alkylsulfonyl, halogen, nitro or cyano,
$R^2$ is methyl, ethyl, vinyl, ethynyl or methoxy,
$R^3$ and $R^4$ are hydrogen or together form a double bond,
A is $C_3$-$C_7$cycloalkyl which is unsubstituted or substituted once or twice by $C_1$-$C_6$alkyl, $C_1$-$C_6$haloalkyl, $C_1$-$C_6$alkoxy, $C_1$-$C_6$alkylcarbonyloxy, $C_2$-$C_6$alkenyl, =O or =N—$R^{10}$, where $R^{10}$ is hydroxyl, $C_1$-$C_6$alkyl, $C_1$-$C_6$haloalkyl, $C_3$-$C_7$cycloalkyl, $C_1$-$C_6$alkoxy, $C_1$-$C_6$alkoxy$C_1$-$C_6$alkoxy or $C_1$-$C_6$haloalkoxy,
or A is optionally substituted phenyl as defined in claim 1, and
G is hydrogen or an agriculturally acceptable metal, sulfonium, ammonium, or latentiating group,
wherein the latentiating group is as defined in claim 1.

3. Compound according to claim 2, wherein $R^1$ is $C_1$-$C_4$alkyl, $C_1$-$C_2$alkoxy, $C_1$-$C_2$haloalkoxy, halogen, phenyl, or phenyl substituted by $C_1$-$C_4$alkyl, $CF_3$, $CF_2C_1$, $CF_2H$, $CCl_2H$, $FCH_2$, $ClCH_2$, $BrCH_2$, $CH_3CHF$, $(CH_3)_2CF$, $CF_3CH_2$, $CHF_2CH_2$, $C_1$-$C_4$alkylsulfonyl, halogen, nitro or cyano.

4. Compound according to claim 1, wherein $R^1$ is $C_1$-$C_4$alkyl, $C_1$-$C_2$alkoxy, $C_1$-$C_2$haloalkoxy, halogen, phenyl, or phenyl substituted by $C_1$-$C_4$alkyl, $CF_3$, $CF_2C_1$, $CF_2H$, $CCl_2H$, $FCH_2$, $ClCH_2$, $BrCH_2$, $CH_3CHF$, $(CH_3)_2CF$, $CF_3CH_2$, $CHF_2CH_2$, $C_1$-$C_4$alkylsulfonyl, halogen, nitro or cyano.

5. Compound according to claim 4, wherein $R^1$ is $C_1$-$C_4$alkyl or halogen.

6. Compound according to claim 1, wherein $R^2$ is methyl.

7. Compound according to claim 1, wherein $R^3$ and $R^4$ are hydrogen.

8. Compound according to claim 1, wherein A is $C_3$-$C_7$-cycloalkyl which is unsubstituted or substituted once or twice by $C_1$-$C_4$alkyl, $C_1$-$C_6$alkylcarbonyloxy, $C_4$-$C_6$alkenyl, =O or =N—$R^{10}$, where $R^{10}$ is hydroxyl or $C_1$-$C_4$alkoxy.

9. Compound according to claim 1, wherein G is hydrogen or an agriculturally acceptable metal, sulfonium or ammonium group, or a latentiating group of the formula C($X^a$)—$R^a$ or C($X^b$)—$X^c$—$R^b$, wherein $X^a$ and $X^b$ are independently of each other oxygen or sulfur, and $R^a$ and $R^b$ are as defined in claim 1.

10. Compound according to claim 1, wherein G is hydrogen or an agriculturally acceptable metal, sulfonium or ammonium group, or a latentiating group of the formula $C(X^a)$—$R^a$ or $C(X^b)$—$X^c$—$R^b$, wherein $X^a$ and $X^b$ are independently of each other oxygen or sulfur, and $R^a$ is hydrogen or $C_1$-$C_{18}$alkyl and $R^b$ is $C_1$-$C_{18}$alkyl.

11. Compound according to claim 1, wherein $R^1$ is $C_1$-$C_6$alkyl or halogen, $R^2$ is methyl, $R^3$ and $R^4$ are hydrogen or together form a double bond, and A is $C_3$-$C_7$-cycloalkyl which is unsubstituted or substituted once or twice by $C_1$-$C_6$alkyl, $C_1$-$C_6$alkylcarbonyloxy, $C_2$-$C_6$alkenyl, =O or =N—$R^{10}$, where $R^{10}$ is hydroxyl or $C_1$-$C_6$alkoxy, and G is hydrogen or a latentiating group.

12. Compound according to claim 11, wherein $R^1$ is methyl or bromo, $R^2$ is methyl, $R^3$ and $R^4$ are hydrogen, and A is $C_5$- or $C_6$-cycloalkyl which is unsubstituted or substituted once or twice by methyl, propenyl, methylcarbonyloxy, =O or =N—$R^{10}$, where $R^{10}$ is hydroxyl or methoxy, and G is hydrogen or pivaloyl.

13. Compound according to claim 1, wherein A is optionally substituted phenyl, and either:

(a) the compound of formula (I) is a compound of formula (IB):

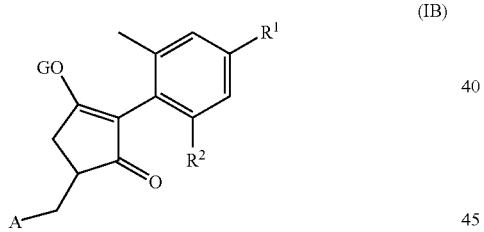

(IB)

wherein:

G is hydrogen;

$R^2$ is $CH_3$ or $CH_3O$;

$R^1$ is $CH_3$, $CH_2CH_3$, F, Cl, Br, $CH_3O$, $CH_3CH_2O$, —CH=$CH_2$, —CCH, phenyl, 2-fluorophenyl, 2-chlorophenyl, 2-trifluoromethylphenyl, 2-nitrophenyl, 2-methylphenyl, 2-methanesulfonylphenyl, 2-cyanophenyl, 3-fluorophenyl, 3-chlorophenyl, 3-trifluoromethylphenyl, 3-nitrophenyl, 3-methylphenyl, 3-methanesulfonylphenyl, 3-cyanophenyl, 4-fluorophenyl, 4-chlorophenyl, 4-bromophenyl, 4-difluoromethoxyphenyl, 2-fluoro-4-chlorophenyl, 3-fluoro-4-chlorophenyl, 2-chloro-4-chlorophenyl, 2-chloro-4-fluorophenyl, 3-chloro-4-chlorophenyl, 3-chloro-4-fluorophenyl, 2-methyl-4-chlorophenyl, 4-trifluoromethylphenyl, 4-nitrophenyl, 4-methylphenyl, 4-methanesulfonylphenyl, or 4-cyanophenyl; and A is of sub-formula (xv), (xvi), (xvii), (xviii), (xix), (xx) or (xxi):

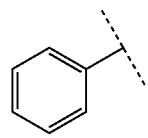
(xv)

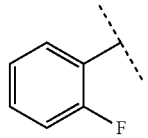
(xvi)

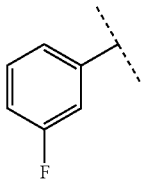
(xvii)

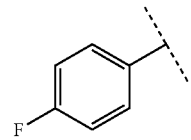
(xviii)

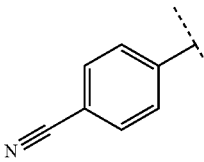
(xix)

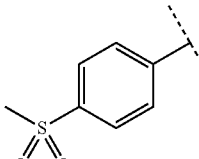
(xx)

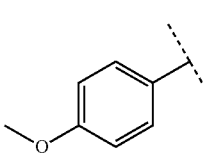
(xxi)

(b) the compound is one of the following compounds A13, A15, A16, A18, A20, A21, A22, B7, B8, B9, B10, B11, B12, B13, B14, B15, B16, B17, B18 or B19:

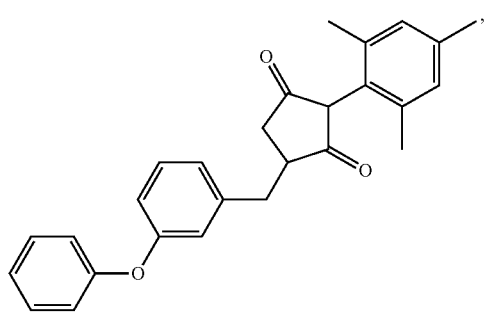
(A13)

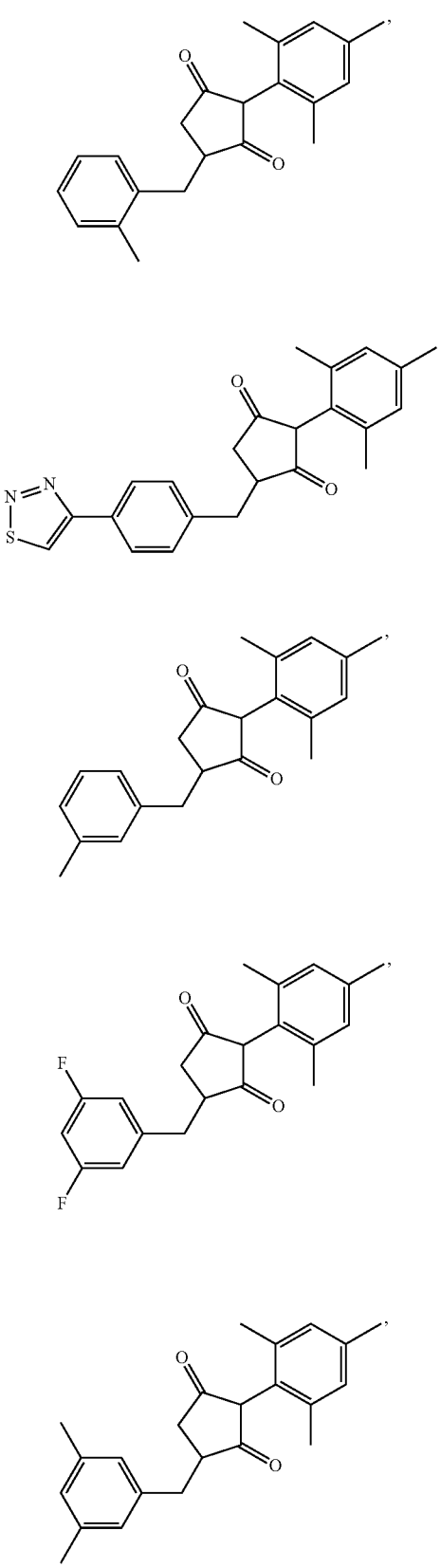
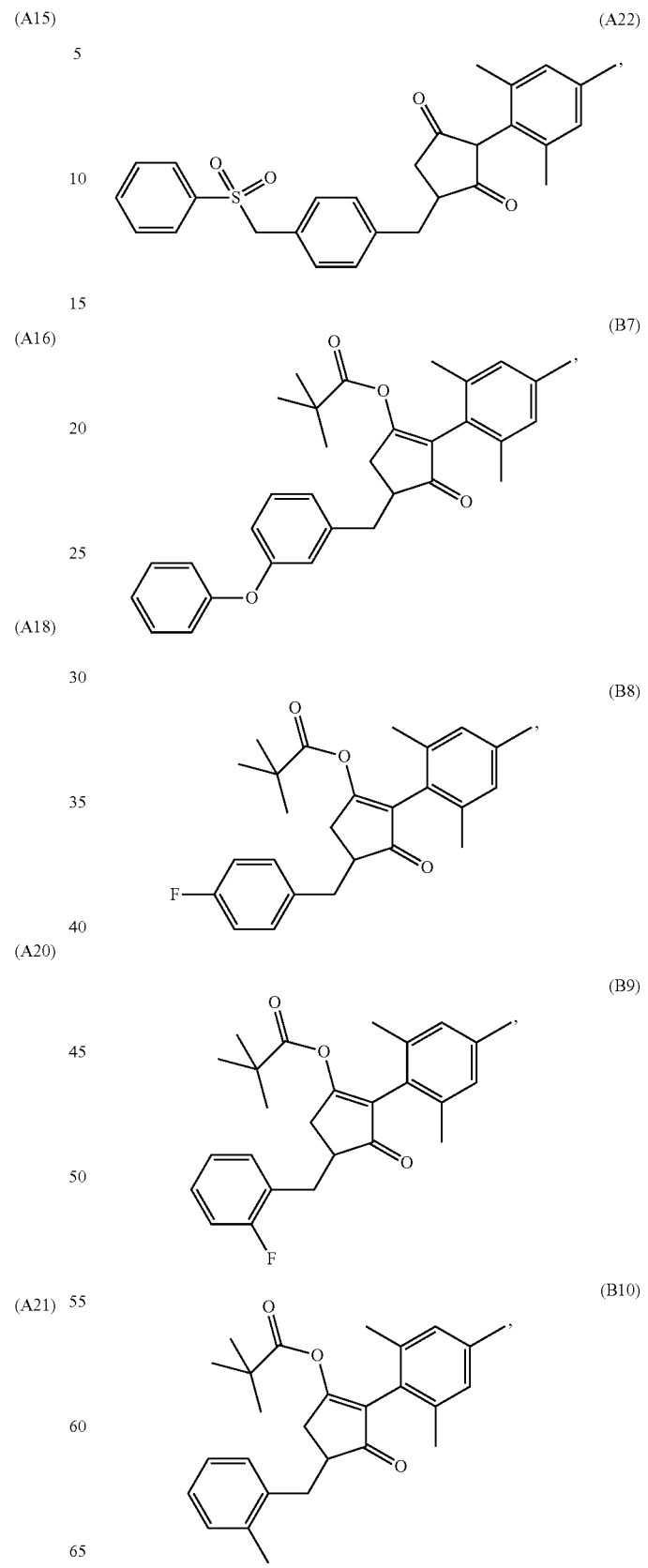

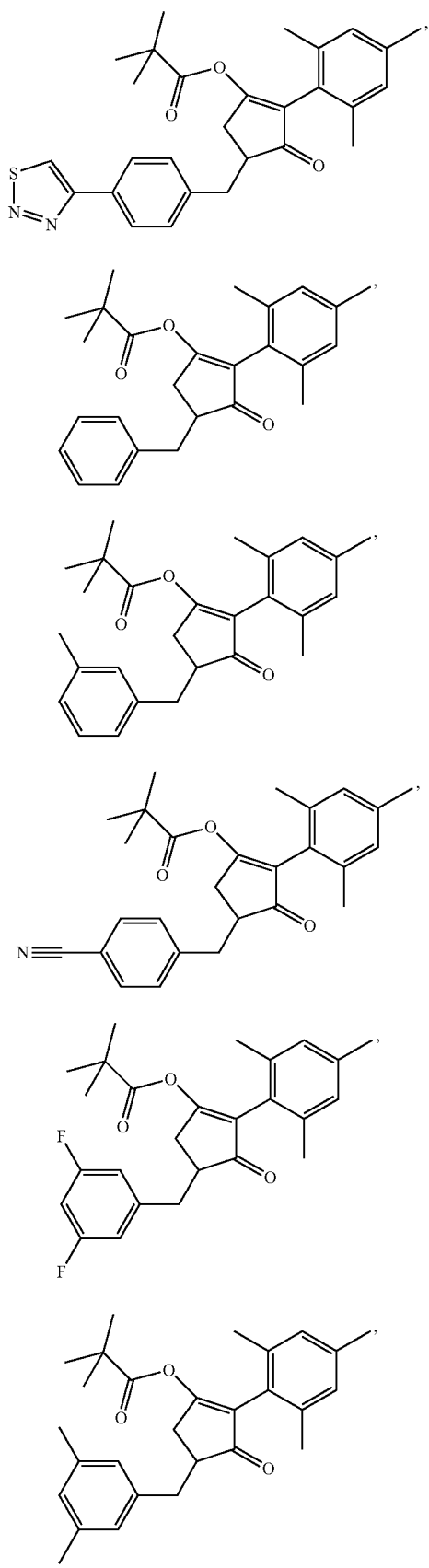
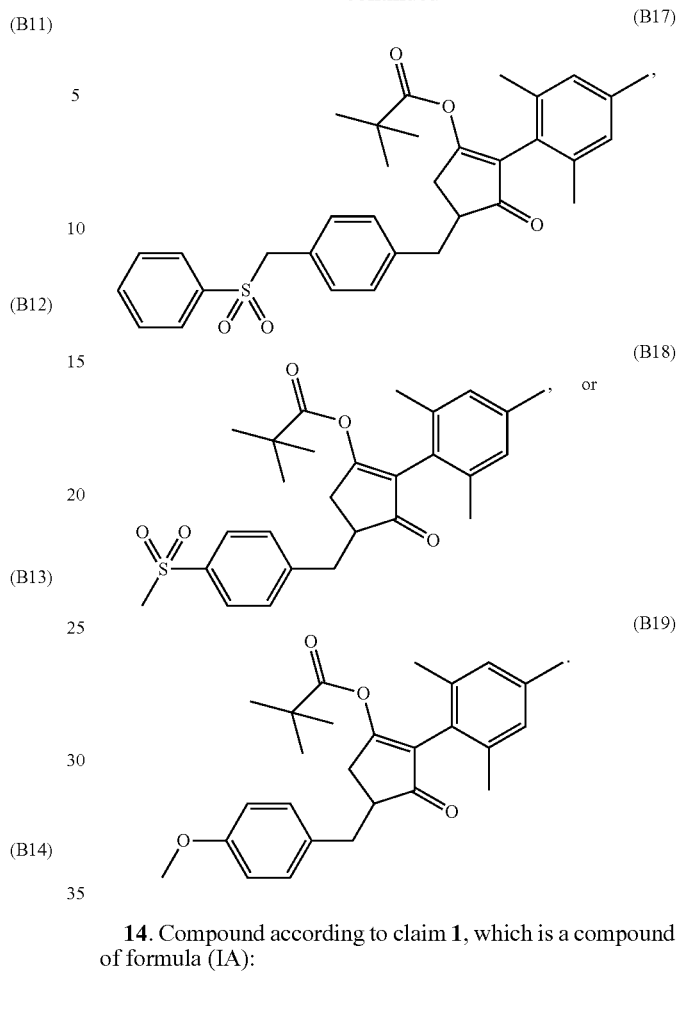

14. Compound according to claim 1, which is a compound of formula (IA):

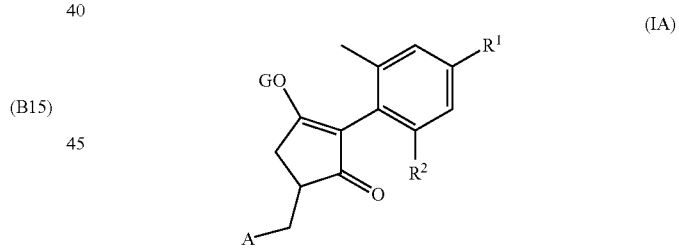

wherein G is hydrogen;
R² is CH₃ or CH₃O;
R¹ is CH₃, CH₂CH₃, F, Cl, Br, CH₃O, CH₃CH₂O, —CH=CH₂, —CCH, phenyl, 2-fluorophenyl, 2-chlorophenyl, 2-trifluoromethylphenyl, 2-nitrophenyl, 2-methylphenyl, 2-methanesulfonylphenyl, 2-cyanophenyl, 3-fluorophenyl, 3-chlorophenyl, 3-trifluoromethylphenyl, 3-nitrophenyl, 3-methylphenyl, 3-methanesulfonylphenyl, 3-cyanophenyl, 4-fluorophenyl, 4-chlorophenyl, 4-bromophenyl, 4-difluoromethoxyphenyl, 2-fluoro-4-chlorophenyl, 3-fluoro-4-chlorophenyl, 2-chloro-4-chlorophenyl, 2-chloro-4-fluorophenyl, 3-chloro-4-chlorophenyl, 3-chloro-4-fluorophenyl, 2-methyl-4-chlorophenyl, 4-trifluoromethylphenyl, 4-nitrophenyl, 4-methylphenyl, 4-methanesulfonylphenyl, or 4-cyanophenyl; and
A is of sub-formula (i), (ii), (iii), (iv), (v), (vi), (vii), (viii), (ix), (x), (xi), (xii), (xiii) or (xiv):

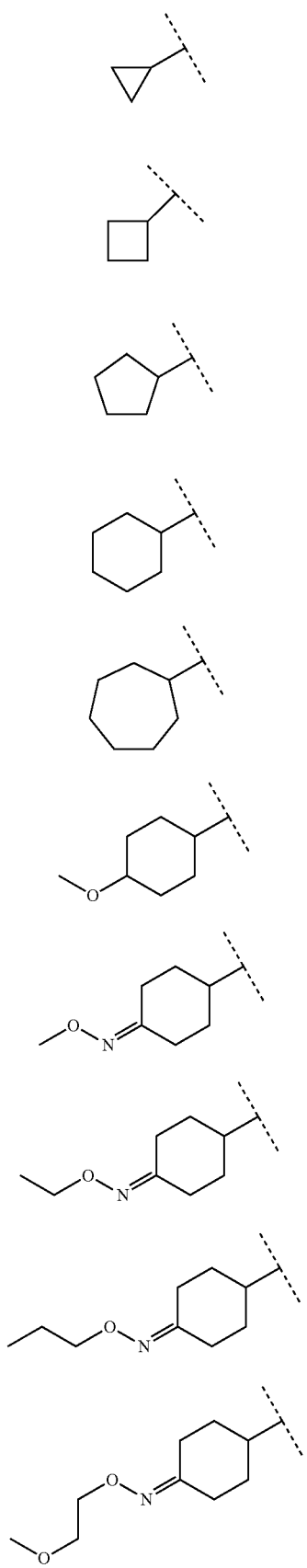

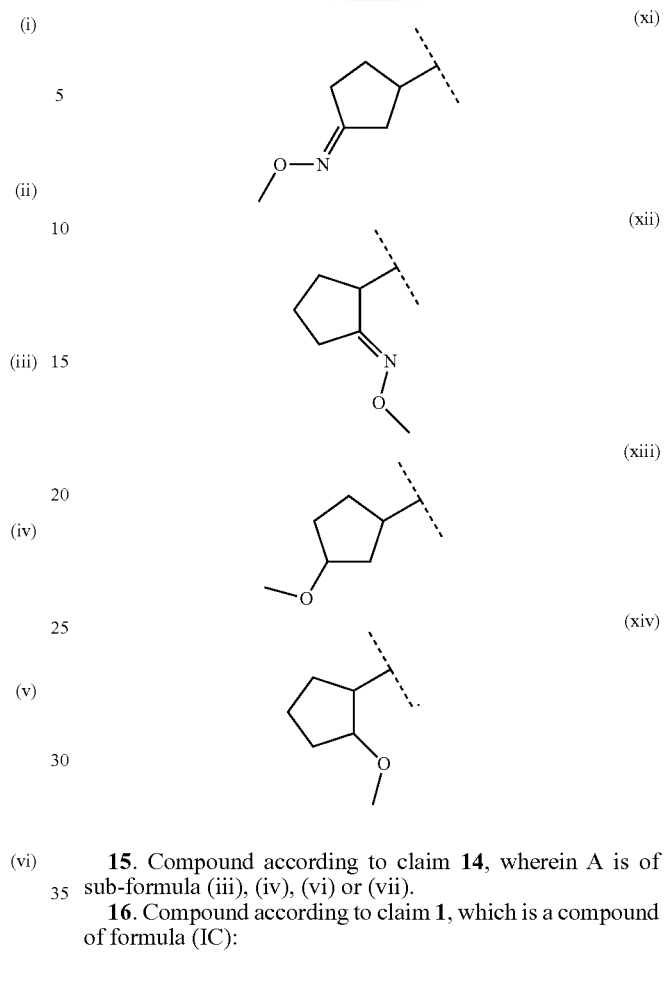

15. Compound according to claim 14, wherein A is of sub-formula (iii), (iv), (vi) or (vii).

16. Compound according to claim 1, which is a compound of formula (IC):

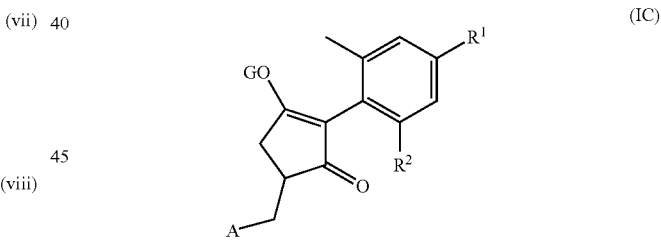

wherein G is hydrogen;
$R^2$ is $CH_3$ or $CH_3O$;
$R^1$ is $CH_3$, $CH_2CH_3$, F, Cl, Br, $CH_3O$, $CH_3CH_2O$, —CH=$CH_2$, —CCH, phenyl, 2-fluorophenyl, 2-chlorophenyl, 2-trifluoromethylphenyl, 2-nitrophenyl, 2-methylphenyl, 2-methanesulfonylphenyl, 2-cyanophenyl, 3-fluorophenyl, 3-chlorophenyl, 3-trifluoromethylphenyl, 3-nitrophenyl, 3-methylphenyl, 3-methanesulfonylphenyl, 3-cyanophenyl, 4-fluorophenyl, 4-chlorophenyl, 4-bromophenyl, 4-difluoromethoxyphenyl, 2-fluoro-4-chlorophenyl, 3-fluoro-4-chlorophenyl, 2-chloro-4-chlorophenyl, 2-chloro-4-fluorophenyl, 3-chloro-4-chlorophenyl, 3-chloro-4-fluorophenyl, 2-methyl-4-chlorophenyl, 4-trifluoromethylphenyl, 4-nitrophenyl, 4-methylphenyl, 4-methanesulfonylphenyl, or 4-cyanophenyl; and
A is of sub-formula (6b), (6c), (6d), (6e), (6f), (6g), (6h), or (6i):

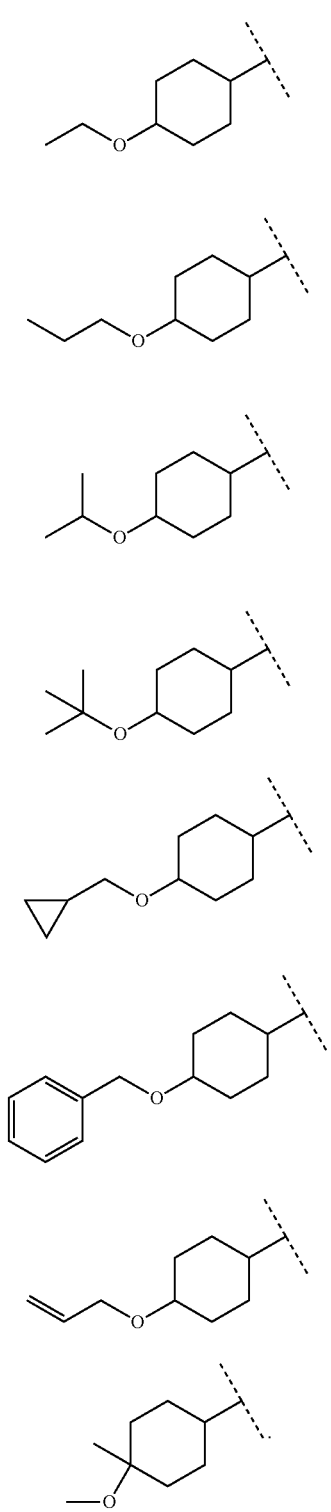
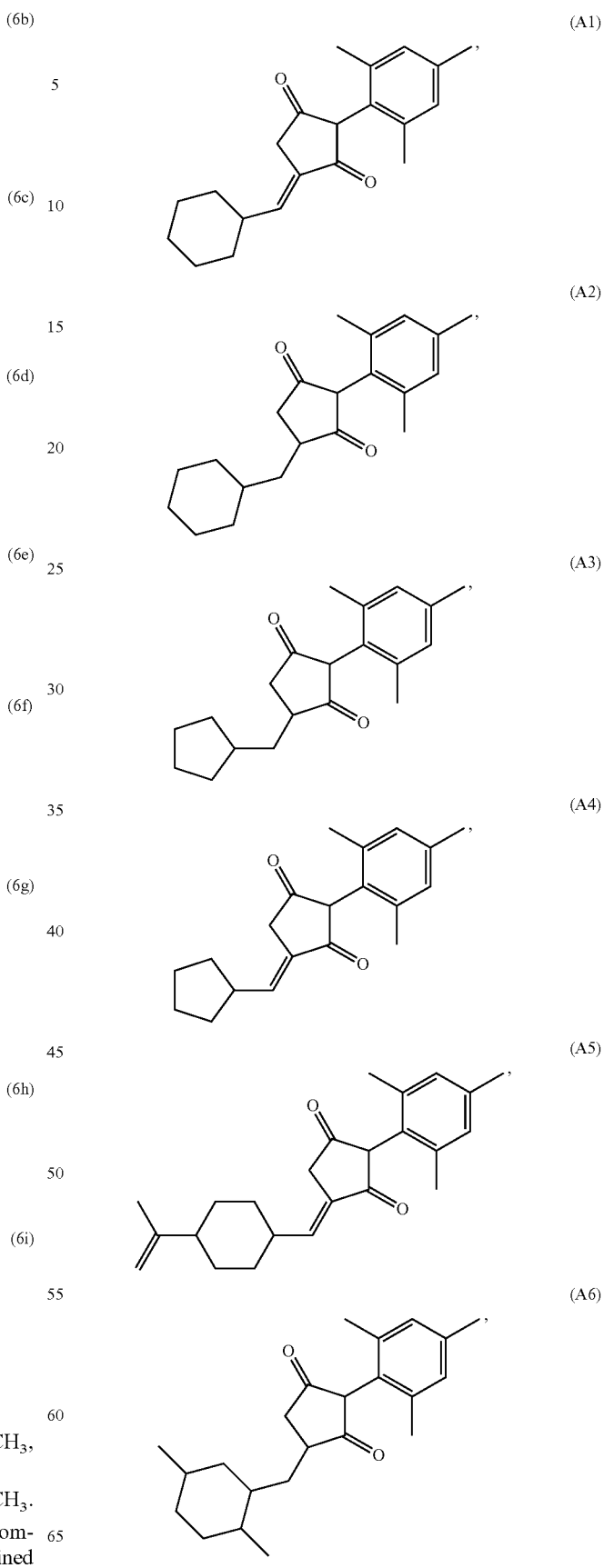
17. Compound according to claim 14, wherein $R^1$ is $CH_3$, $CH_2CH_3$, F, Cl, or Br.
18. Compound according to claim 14, wherein $R^2$ is $CH_3$.
19. Compound according to claim 1, which is one of Compounds A1 to A9, A11 to A24, A38, or B1 to B19, as defined by the structures shown below:

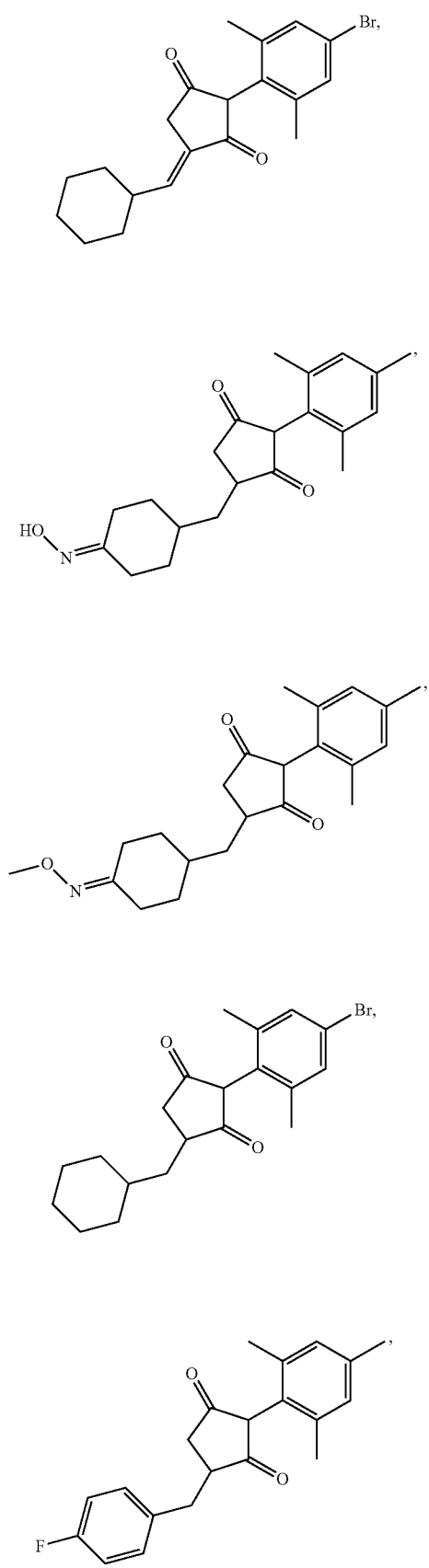

(A18) 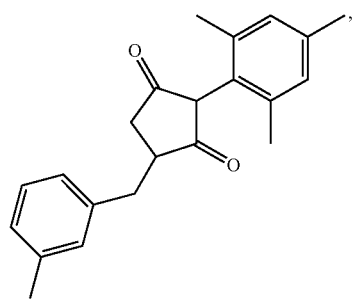
(A23) 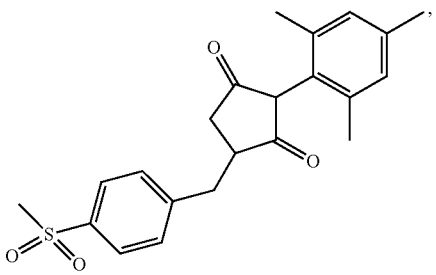
(A19) 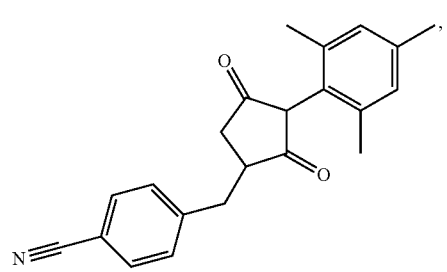
(A24) 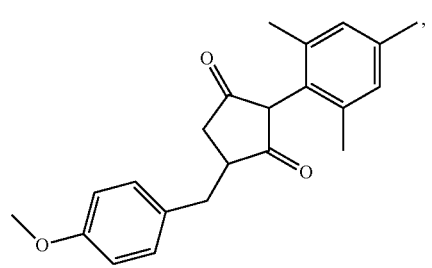
(A20) 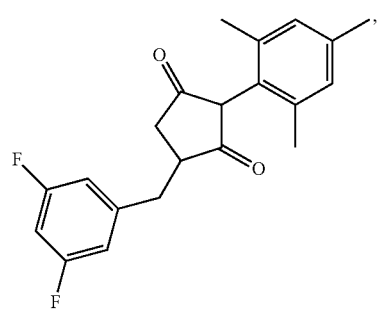
(A38) 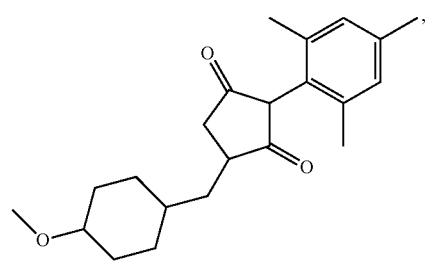
(A21) 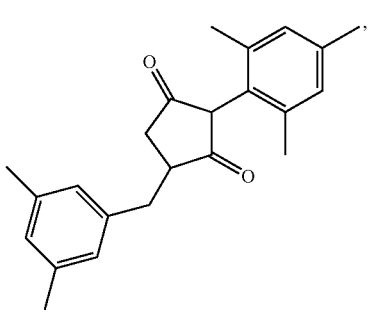
(B1) 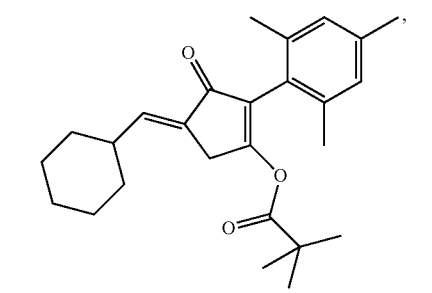
(A22) 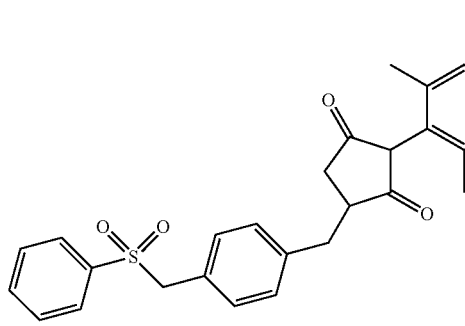
(B2) 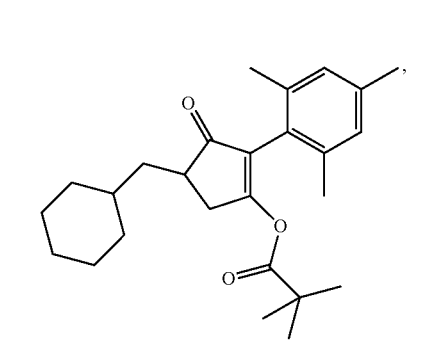

-continued
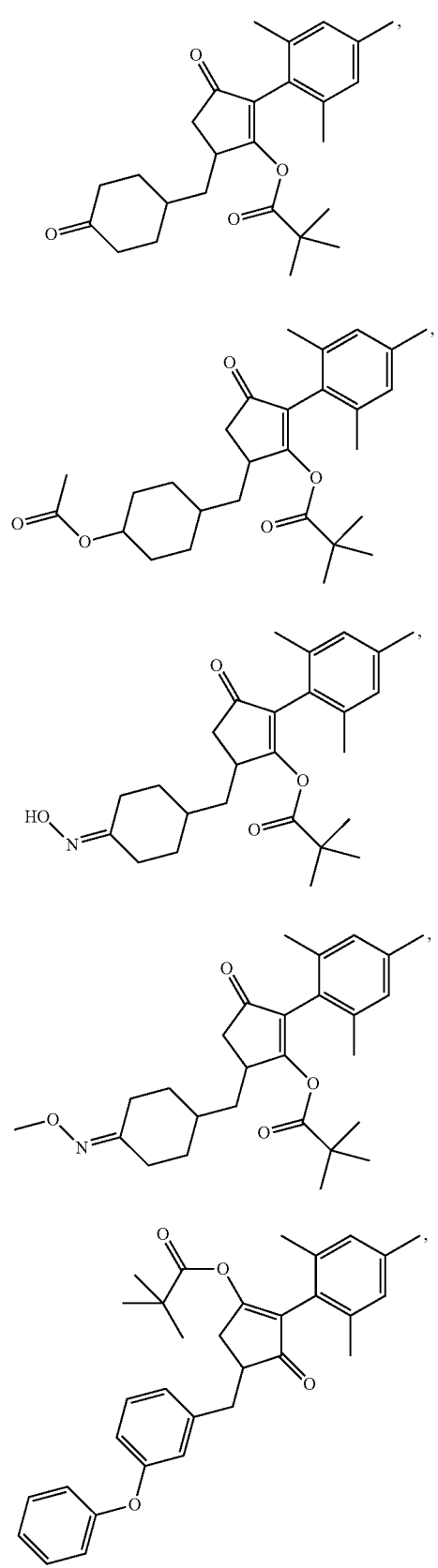
(B3)
(B4)
(B5)
(B6)
(B7)
-continued
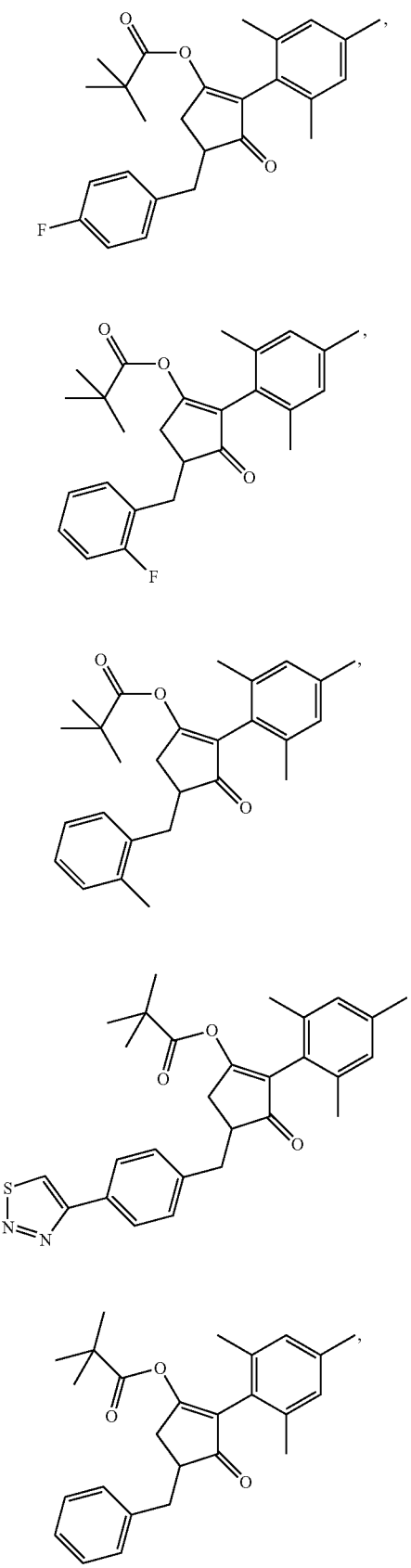
(B8)
(B9)
(B10)
(B11)
(B12)

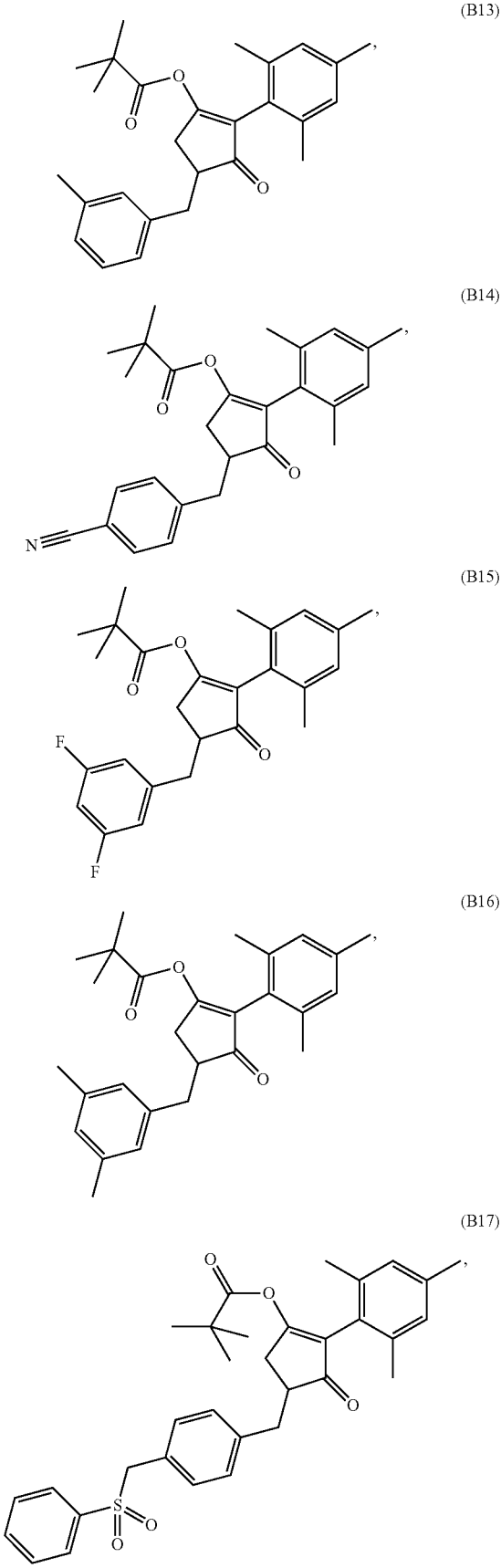
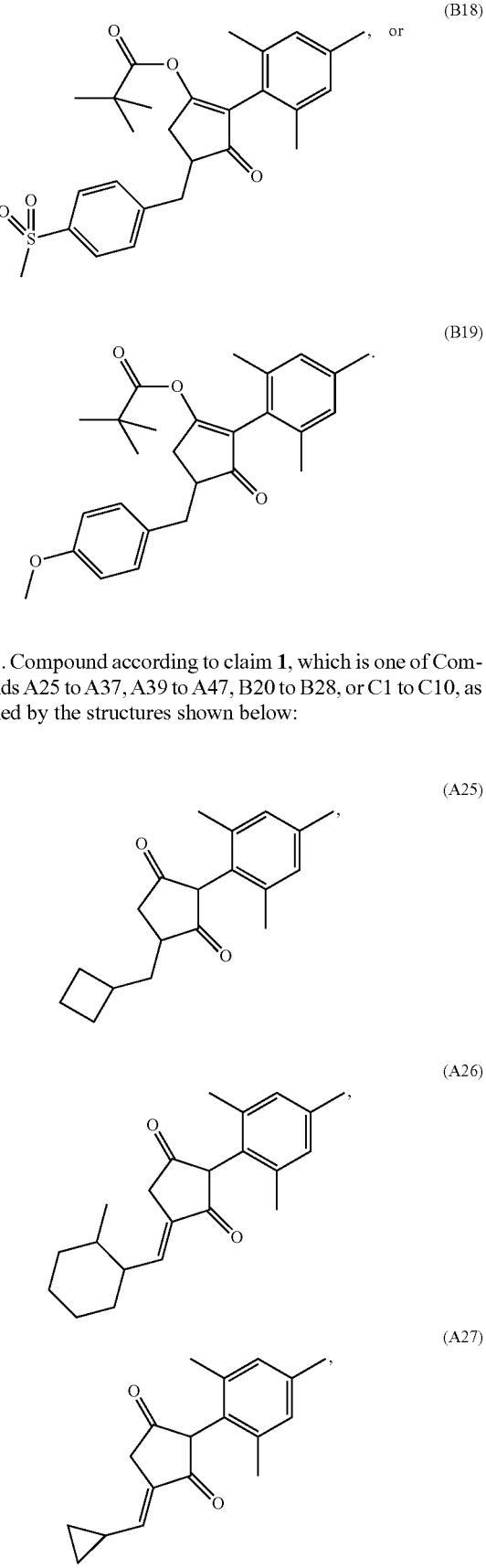
20. Compound according to claim 1, which is one of Compounds A25 to A37, A39 to A47, B20 to B28, or C1 to C10, as defined by the structures shown below:

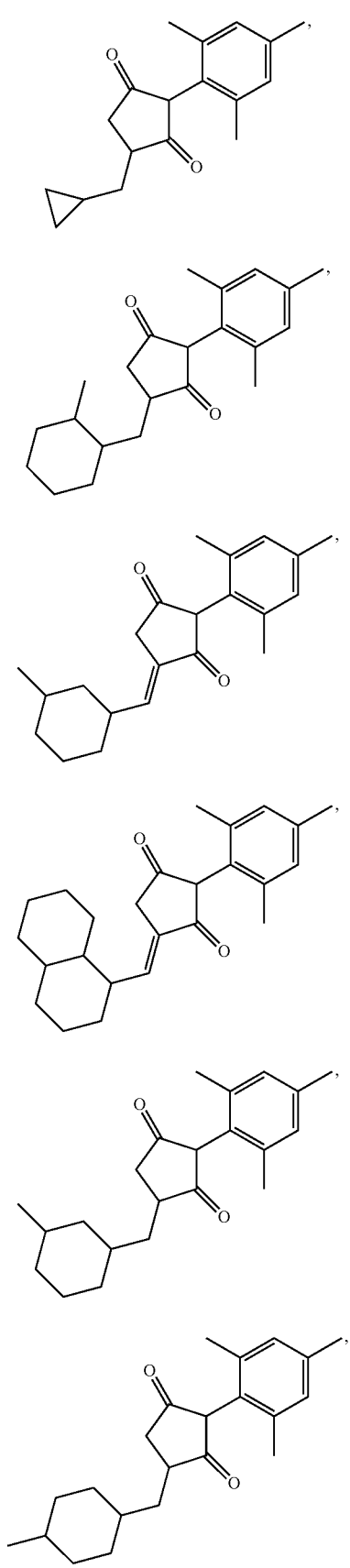
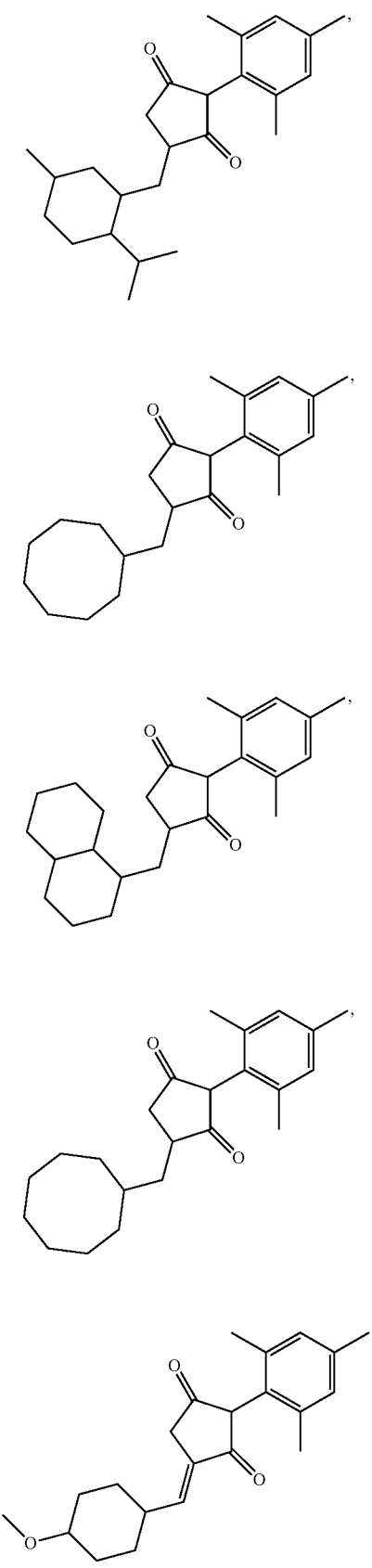

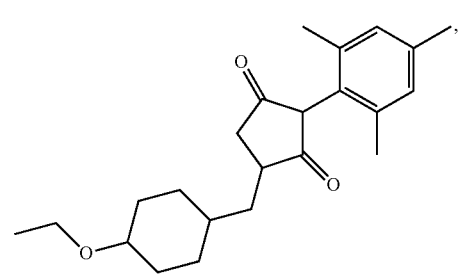 (A40)
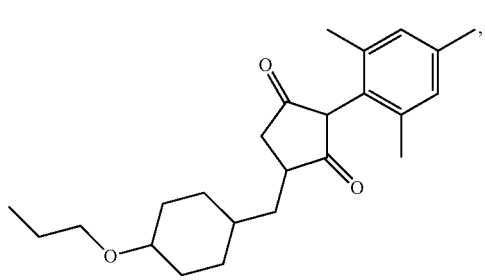 (A41)
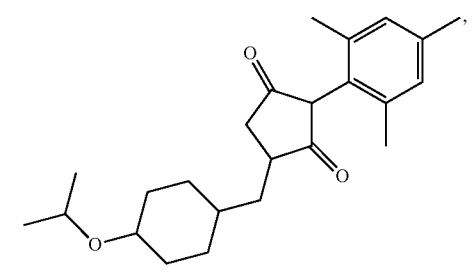 (A42)
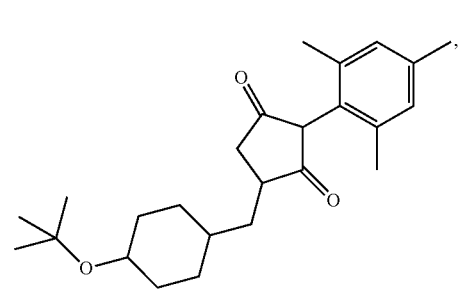 (A43)
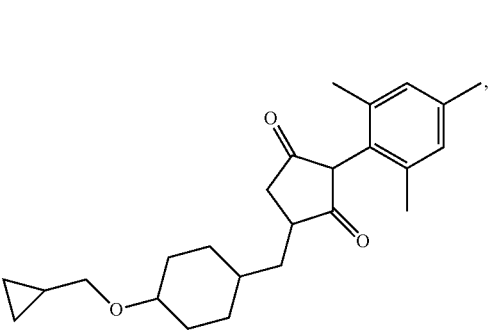 (A44)
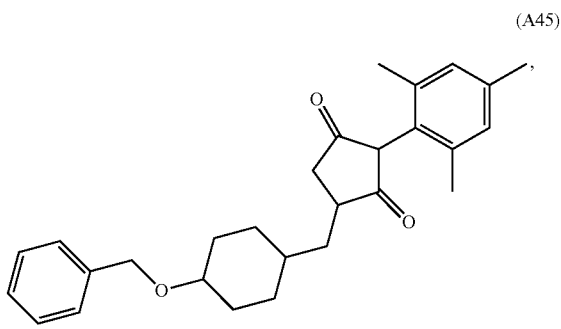 (A45)
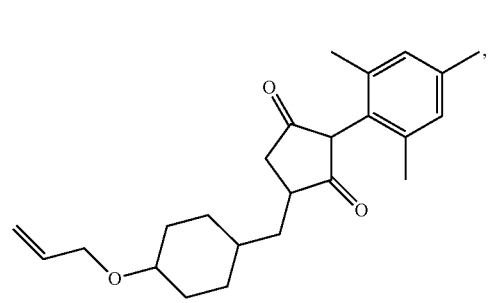 (A46)
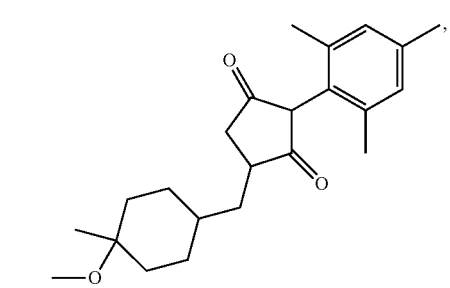 (A47)
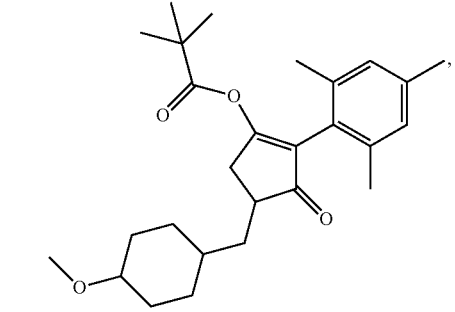 (B20)
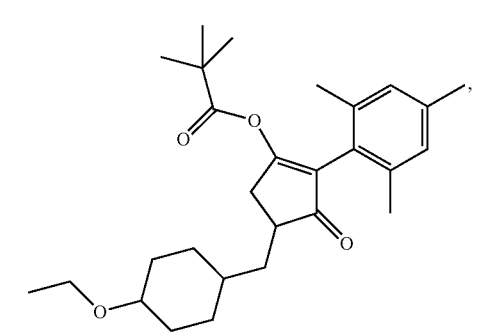 (B21)

(B22)
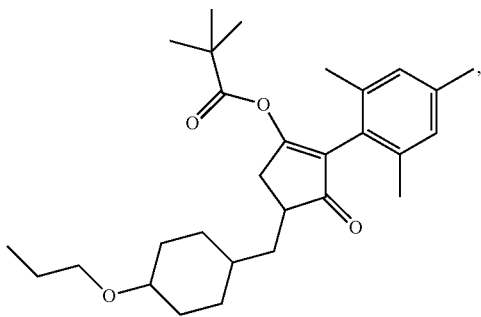
(B23)
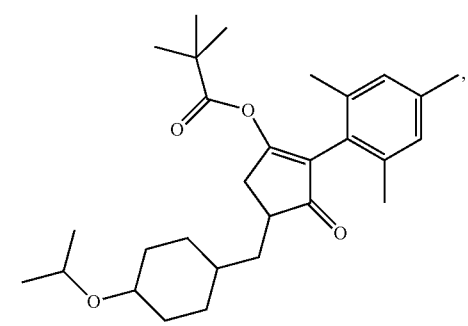
(B24)
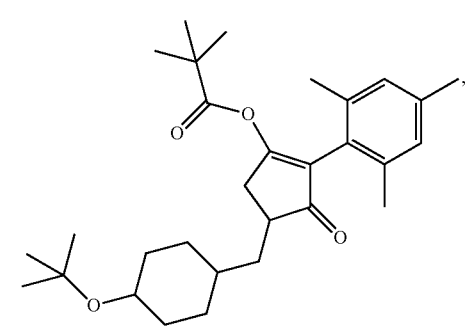
(B25)
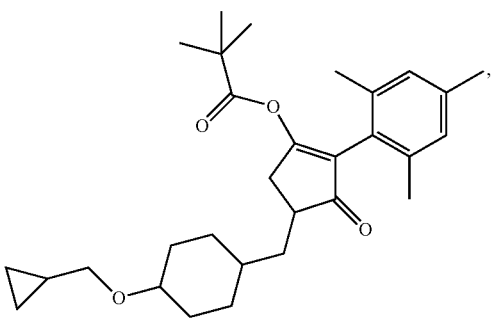
(B26)
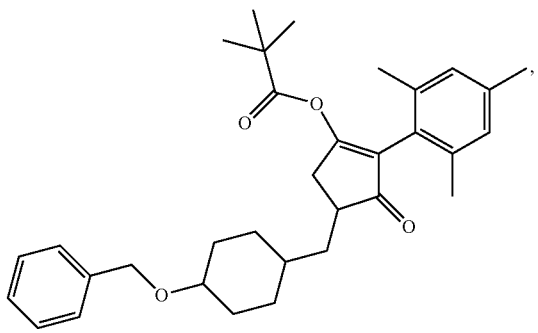
(B27)
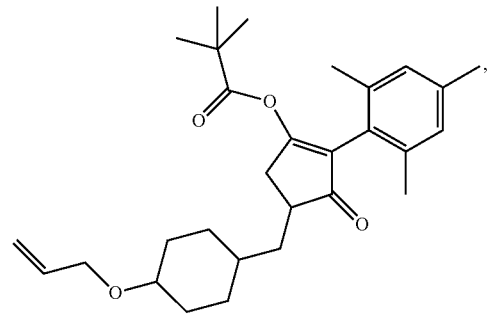
(B28)
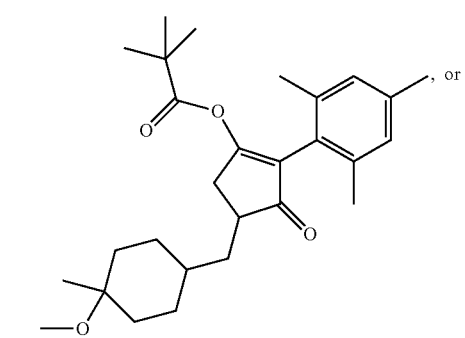
(C1)
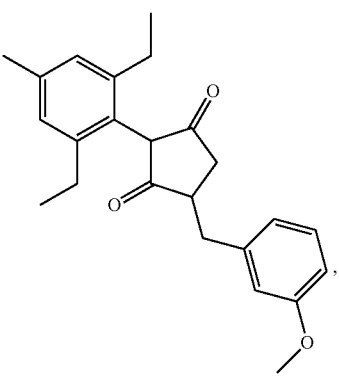

(C2)
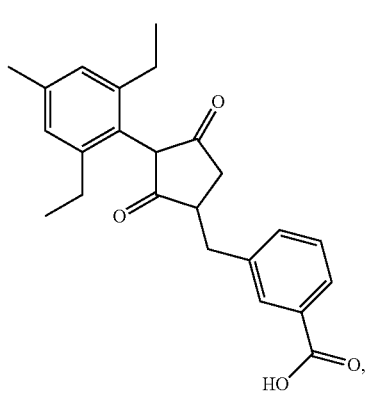
(C3)
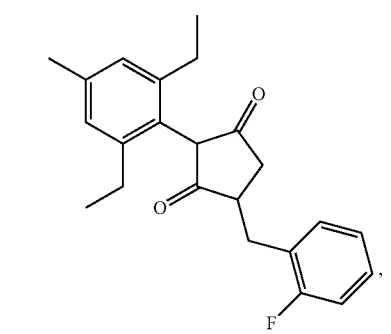
(C4)
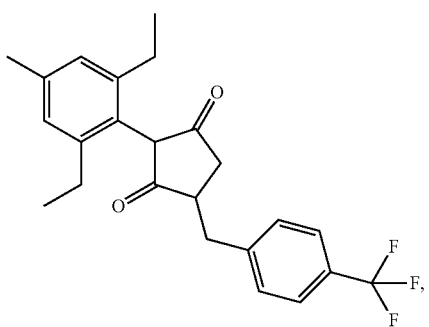
(C5)
(C6)
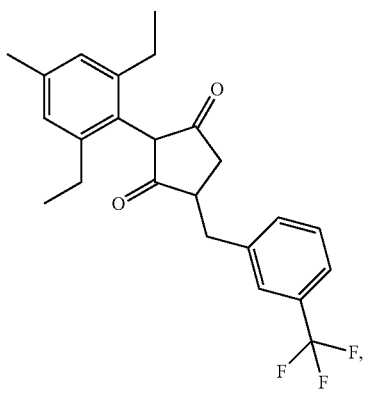
(C7)
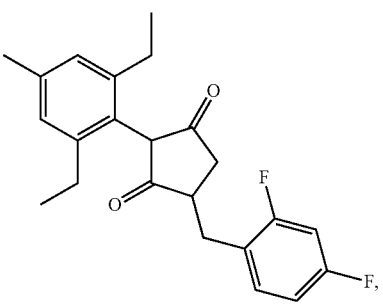
(C8)
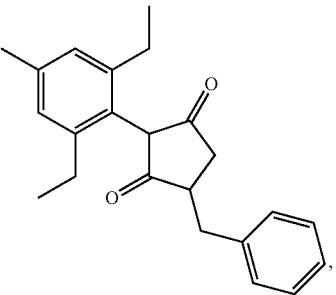
(C9)
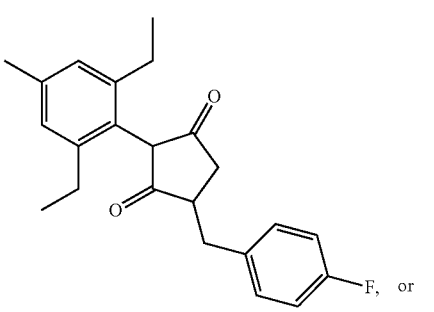
or -continued

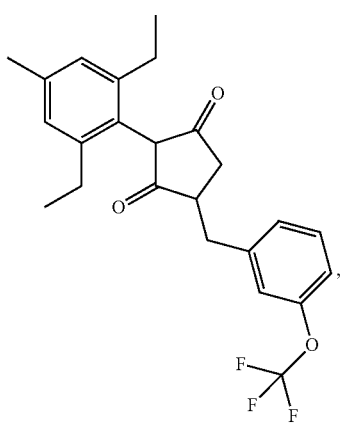
(C10)

21. A herbicidal composition, which comprises a herbicidally effective amount of a compound of formula I as defined in claim 1.

22. A herbicidal composition according to claim 21, which comprises a herbicidally effective amount of a compound of formula I as defined in claim 1, and optionally a further herbicide as mixture partner for the compound of formula I, or optionally a safener, or both.

23. A herbicidal composition according to claim 22, which comprises a herbicidally effective amount of a compound of formula I as defined in any claim 1, a safener, and optionally a further herbicide as mixture partner for the compound of formula I,
wherein the safener is benoxacor, cloquintocet-mexyl, cyprosulfamide, mefenpyr-diethyl or N-(2-methoxybenzoyl)-4-[(methylaminocarbonyl)amino]benzenesulfonamide.

24. A method of controlling grasses and weeds in crops of useful plants, which comprises applying a herbicidally effective amount of a compound of formula I as defined in claim 1, to the plants or to the locus thereof.

25. A method according to claim 24, wherein the crops of useful plants are wheat, barley, corn or soybean.

* * * * *